US008748012B2

(12) United States Patent
Zeng et al.

(10) Patent No.: US 8,748,012 B2
(45) Date of Patent: Jun. 10, 2014

(54) HOST MATERIALS FOR OLED

(75) Inventors: Lichang Zeng, Lawrenceville, NJ (US);
Alexey B. Dyatkin, Ambler, PA (US);
Gregg Kottas, Ewing, NJ (US)

(73) Assignee: Universal Display Corporation, Ewing, NJ (US)

( * ) Notice: Subject to any disclaimer, the term of this patent is extended or adjusted under 35 U.S.C. 154(b) by 220 days.

(21) Appl. No.: 13/067,345

(22) Filed: May 25, 2011

(65) Prior Publication Data
US 2012/0298966 A1 Nov. 29, 2012

(51) Int. Cl.
*H01L 51/54* (2006.01)

(52) U.S. Cl.
USPC ........... 428/690; 428/917; 313/504; 313/505; 313/506; 257/40; 257/E51.05; 257/E51.026; 257/E51.032; 548/304.1; 548/418; 548/440; 546/18; 546/24; 546/79; 546/81; 546/101

(58) Field of Classification Search
USPC .................. 428/690, 917; 313/504, 505, 506; 257/40, E51.05, E51.026, E51.032; 546/18, 79, 81, 101, 24; 548/440, 548/304.1, 418
See application file for complete search history.

(56) References Cited

U.S. PATENT DOCUMENTS

| 4,769,292 | A | 9/1988 | Tang et al. |
|---|---|---|---|
| 5,061,569 | A | 10/1991 | VanSlyke et al. |
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,468,819 | B1 | 10/2002 | Kim et al. |
| 6,528,187 | B1 | 3/2003 | Okada |
| 6,687,266 | B1 | 2/2004 | Ma et al. |
| 6,835,469 | B2 | 12/2004 | Kwong et al. |
| 6,921,915 | B2 | 7/2005 | Takiguchi et al. |
| 7,087,321 | B2 | 8/2006 | Kwong et al. |
| 7,090,928 | B2 | 8/2006 | Thompson et al. |
| 7,154,114 | B2 | 12/2006 | Brooks et al. |
| 7,250,226 | B2 | 7/2007 | Tokito et al. |
| 7,279,704 | B2 | 10/2007 | Walters et al. |
| 7,332,232 | B2 | 2/2008 | Ma et al. |

(Continued)

FOREIGN PATENT DOCUMENTS

| EP | 0650955 | 5/1995 |
|---|---|---|
| EP | 2034538 | 3/2009 |

(Continued)

OTHER PUBLICATIONS

International Search Report in PCT/US2012/039015.

(Continued)

*Primary Examiner* — Gregory Clark
(74) *Attorney, Agent, or Firm* — Duane Morris LLP

(57) ABSTRACT

Novel aryl silicon and aryl germanium host materials are described. These compounds improve OLED device performance when used as hosts in the emissive layer of the OLED.

19 Claims, 4 Drawing Sheets

(56) References Cited

U.S. PATENT DOCUMENTS

| | | |
|---|---|---|
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2010/0051914 A1 | 3/2010 | Hwang et al. |
| 2011/0278552 A1* | 11/2011 | Numata et al. .............. 257/40 |

FOREIGN PATENT DOCUMENTS

| | | |
|---|---|---|
| JP | 200511610 | 1/2005 |
| JP | 1725079 | 11/2006 |
| JP | 2007123392 | 5/2007 |
| JP | 2007254297 | 10/2007 |
| JP | 2008074939 | 10/2009 |
| WO | WO 0139234 | 5/2001 |
| WO | WO 0202714 | 1/2002 |
| WO | WO 0215645 | 2/2002 |
| WO | WO 03040257 | 5/2003 |
| WO | WO 03060956 | 7/2003 |
| WO | WO 2004093207 | 10/2004 |
| WO | WO 2004107822 | 12/2004 |
| WO | WO 2005014551 | 2/2005 |
| WO | WO 2005019373 | 3/2005 |
| WO | WO 2005030900 | 4/2005 |
| WO | WO 2005089025 | 9/2005 |
| WO | WO 2005123873 | 12/2005 |
| WO | WO 2006009024 | 1/2006 |
| WO | WO 2006056418 | 6/2006 |
| WO | WO 2006072002 | 7/2006 |
| WO | WO 2006082742 | 8/2006 |
| WO | WO 2006098120 | 9/2006 |
| WO | WO 2006100298 | 9/2006 |
| WO | WO 2006103874 | 10/2006 |
| WO | WO 2006114966 | 11/2006 |
| WO | WO 2006132173 | 12/2006 |
| WO | WO 2007002683 | 1/2007 |
| WO | WO 2007004380 | 1/2007 |
| WO | WO 2007063754 | 6/2007 |
| WO | WO 2007063796 | 6/2007 |
| WO | WO 2008056746 | 5/2008 |
| WO | WO 2008101842 | 8/2008 |
| WO | WO 2008132085 | 11/2008 |
| WO | WO 2009000673 | 12/2008 |
| WO | WO 2009003898 | 1/2009 |
| WO | WO 2009008311 | 1/2009 |
| WO | WO 2009018009 | 2/2009 |
| WO | WO 2009050290 | 4/2009 |
| WO | WO 2009021126 | 5/2009 |
| WO | WO 2009062578 | 5/2009 |
| WO | WO 2009063833 | 5/2009 |
| WO | WO 2009066778 | 5/2009 |
| WO | WO 2009066779 | 5/2009 |
| WO | WO 2009086028 | 7/2009 |
| WO | WO 2009100991 | 8/2009 |
| WO | WO 2011/125680 | 10/2011 |

OTHER PUBLICATIONS

Baldo et al., "Highly Efficient Phosphorescent Emission from Organic Electroluminescent Devices," Nature, vol. 395, 151-154, (1998).

Baldo et al., "Very high-efficiency green organic light-emitting devices based on electrophosphorescence," Appl. Phys. Lett., vol. 75, No. 3, 4-6 (1999).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," Adv. Mater., 6(9):677-679 (1994).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Tung, Yung-Liang et al, "Organic Light-Emitting Diodes Based on Charge-Neutral $Ru^{II}$ PHosphorescent Emitters," Adv. Mater., 17(8):1059-1064 (2005).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).

Wong, Wai-Yeung, "Multifunctional Iridium Complexes Based on Carbazole Modules as Highly Efficient Electrophosphors," Angew. Chem. Int. Ed., 45:7800-7803 (2006).

Tang, C.W. and VanSlyke, S.A., "Organic Electroluminescent Diodes," Appl. Phys. Lett., 51(12):913-915 (1987).

Adachi, Chihaya et al., "Organic Electroluminescent Device Having a Hole Conductor as an Emitting Layer," Appl. Phys. Lett., 55(15):1489-1491 (1989).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Gao, Zhiqiang et al., "Bright-Blue Electroluminescence From a Silyl-Substituted ter-(phenylene-vinylene) derivative," Appl. Phys. Lett, 74(6):865-867 (1999).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Hung, L.S. et al., "Anode Modification in Organic Light-Emitting Diodes by Low-Frequency Plasma Polymerization of $CHF_3$," Appl. Phys. Lett., 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).

(56) References Cited

OTHER PUBLICATIONS

Wang, Y. et al., "Highly Efficient Electroluminescent Materials Based on Fluorinated Organometallic Iridium Compounds," *Appl. Phys. Lett.*, 79(4):449-451 (2001).
Kwong, Raymond C. et al., "High Operational Stability of Electrophosphorescent Devices," *Appl. Phys. Lett.*, 81(1):162-164 (2002).
Holmes, R.J. et al., "Blue Organic Electrophosphorescence Using Exothermic Host-Guest Energy Transfer," *Appl. Phys. Lett.*, 82(15):2422-2424 (2003).
Sotoyama, Wataru et al., "Efficient Organic Light-Emitting Diodes with Phosphorescent Platinum Complexes Containing NCN—Coordinating Tridentate Ligand," *Appl. Phys. Lett*, 86:153505-1-153505-3 (2005).
Okumoto, Kenji et al., "Green Fluorescent Organic Light-Emitting Device with External Quantum Efficiency of Nearly 10%," *Appl. Phys. Lett.*, 89:063504-1-063504-3 (2006).
Kanno, Hiroshi et al., "Highly Efficient and Stable Red Phosphorescent Organic Light-Emitting Device Using bis[2-(2-benzothiazoyl)phenolato]zinc(II) as host material," *Appl. Phys. Lett*, 90:123509-1-123509-3 (2007).
Aonuma, Masaki et al., "Material Design of Hole Transport Materials Capable of Thick-Film Formation in Organic Light Emitting Diodes," *Appl. Phys. Lett*, 90:183503-1-183503-3 (2007).
Sun, Yiru and Forrest, Stephen R., "High-Efficiency White Organic Light Emitting Devices with Three Separate Phosphorescent Emission Layers," *Appl. Phys. Lett.*, 91:263503-1-263503-3 (2007).
Adachi, Chihaya et al., "High-Efficiency Red Electrophosphorescence Devices," *Appl. Phys. Lett*, 78(11):1622-1624 (2001).
Wong, Keith Man-Chung et al., A Novel Class of Phosphorescent Gold(III) Alkynyl-Based Organic Light-Emitting Devices with Tunable Colour, *Chem. Commun.*, 2906-2908 (2005).
Hamada, Yuji et al., "High Luminance in Organic Electroluminescent Devices with Bis(10-hydroxybenzo[h]quinolinato)beryllium as an Emitter," *Chem. Lett.*, 905-906 (1993).
Nishida, Jun-ichi et al, "Preparation, Characterization, and Electroluminescence Characteristics of α-Diimine-type Platinum(II) Complexes with Perfluorinated Phenyl Groups as Ligands," *Chem. Lett.*, 34(4):592-593 (2005).
Mi, Bao-Xiu et al., "Thermally Stable Hole-Transporting Material for Organic Light-Emitting Diode: an Isoindole Derivative," *Chem. Mater.*, 15(16):3148-3151 (2003).
Huang, Wei-Sheng et al., "Highly Phosphorescent Bis-Cyclometalated Iridium Complexes Containing Benzoimidazole-Based Ligands," *Chem. Mater.*, 16(12)2480-2488 (2004).
Niu, Yu-Hua et al., "Highly Efficient Electrophosphorescent Devices with Saturated Red Emission from a Neutral Osmium Complex," *Chem. Mater.*, 17(13):3532-3536 (2005).
Lo, Shih-Chun et al., "Blue Phosphorescence from Iridium(III) Complexes at Room Temperature," *Chem. Mater.*, 18(21):5119-5129 (2006).
Takizawa, Shin-ya et al., "Phosphorescent Iridium Complexes Based on 2-Phenylimidazo[1,2-α]pyridine Ligands: Tuning of Emission Color toward the Blue Region and Application to Polymer Light-Emitting Devices," *Inorg. Chem.*, 46(10):4308-4319 (2007).
Lamansky, Sergey et al., "Synthesis and Characterization of Phosphorescent Cyclometalated Iridium Complexes," *Inorg. Chem.*, 40(7):1704-1711 (2001).
Ranjan, Sudhir et al., "Realizing Green Phosphorescent Light-Emitting Materials from Rhenium(I) Pyrazolato Diimine Complexes," *Inorg. Chem.*, 42(4):1248-1255 (2003).
Noda, Tetsuya and Shirota, Yasuhiko, "5,5'-Bis(dimesitylboryl)-2,2'-bithiopene and 5,5"-Bis(dimesitylboryl)-2,2':5',2"-terthiophene as a Novel Family of Electron-Transporting Amorphous Molecular Materials," *J. Am. Chem. Soc.*, 120 (37):9714-9715 (1998).
Sakamoto, Youichi et al., "Synthesis, Characterization, and Electron-Transport Property of Perfluorinated Phenylene Dendrimers," *J. Am. Chem. Soc.*, 122(8):1832-1833 (2000).
Adachi, Chihaya et al., "Nearly 100% Internal Phosphorescence Efficiency in an Organic Light Emitting Device," *J. Appl. Phys.*, 90(10):5048-5051 (2001).
Shirota, Yasuhiko et al., "Starburst Molecules Based on π-Electron Systems as Materials for Organic Electroluminescent Devices," *Journal of Luminescence*, 72-74:985-991 (1997).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," *J. Mater. Chem.*, 3(3):319-320 (1993).
Kido, Junji et al., 1,2,4-Triazole Derivative as an Electron Transport Layer in Organic Electroluminescent Devices, *Jpn. J. Appl. Phys.*, 32:L917-L920 (1993).
Van Slyke, S. A. et al., "Organic Electroluminescent Devices with Improved Stability," *Appl. Phys. Lett.*, 69(15 ):2160-2162 (1996).
Guo, Tzung-Fang et al., "Highly Efficient Electrophosphorescent Polymer Light-Emitting Devices," *Organic Electronics*, 1:15-20 (2000).
Palilis, Leonidas C., "High Efficiency Molecular Organic Light-Emitting Diodes Based on Silole Derivatives and Their Exciplexes," *Organic Electronics*, 4:113-121 (2003).
Ikeda, Hisao et al., "P-185: Low-Drive-Voltage OLEDs with a Buffer Layer Having Molybdenum Oxide," *SID Symposium Digest*, 37:923-926 (2006).
T. Östergård et al., "Langmuir-Blodgett Light-Emitting Diodes of Poly(3-Hexylthiophene): Electro-Optical Characteristics Related to Structure," *Synthetic Metals*, 87:171-177 (1997).
Hu, Nan-Xing et al., "Novel High $T_g$ Hole-Transport Molecules Based on Indolo[3,2-b]carbazoles for Organic Light-Emitting Devices," *Synthetic Metals*, 111-112:421-424 (2000).
Salbeck, J. et al., "Low Molecular Organic Glasses for Blue Electroluminescence," *Synthetic Metals*, 91:209-215 (1997).

\* cited by examiner

| LiF/Al 1000 A |
|---|
| Alq 400 A |
| BL 50 A |
| Compound/dopant 15% 300 A |
| NPD 300 A |
| HIL4 100 A |
| ITO 800 A |

FIGURE 4

HOST MATERIALS FOR OLED

The claimed invention was made by, on behalf of, and/or in connection with one or more of the following parties to a joint university corporation research agreement: Regents of the University of Michigan, Princeton University, The University of Southern California, and the University Display Corporation. The agreement was in effect on and before the date the claimed invention was made, and the claimed invention was made as a result of activities undertaken within the scope of the agreement.

FIELD OF THE INVENTION

The present invention relates to compounds suitable for use as host materials in OLEDs, specifically compounds comprising arylgermane and arylsilane groups.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine)iridium, denoted Ir(ppy)$_3$, which has the following structure:

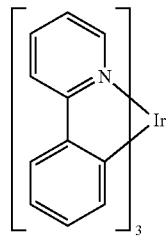

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

A compound of Formula I is provided.

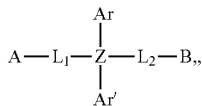

Formula I

In one aspect, Ar and Ar' are independently selected from the group consisting of phenyl, biphenyl, napthyl, dibenzothiolyl, and dibenzofuranyl, which are optionally further substituted. Z is selected from Si and Ge. $L_1$ comprises aryl or heteroaryl groups, and any heteroatoms in the heteroaryl groups are nitrogen. $L_2$ is a single bond or comprises aryl or heteroaryl groups, and any heteroatoms in the heteroaryl groups are nitrogen. $L_1$ and $L_2$ can be optionally further substituted.

Group A contains a group selected from the group consisting of dibenzofuran, dibenzothiophene, azadibenzofuran, azadibenzothiophene, dibenzoselenophene and azadibenzoselenophene, which are optionally further substituted, and wherein the substitution is optionally fused to at least one benzo ring. Group B contains a group selected from the group consisting of carbazole and azacarbazole, which are optionally further substituted, and wherein the substitution is optionally fused to the carbazole or azacarbazole group.

In one aspect, A is selected from the group consisting of:

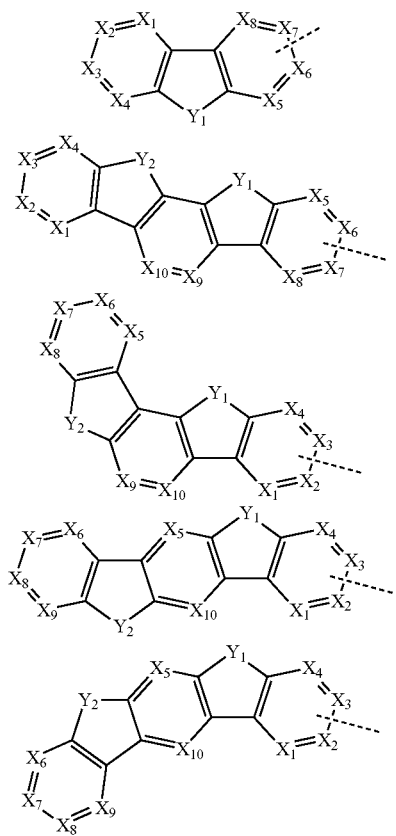

In another aspect, B is selected from the group consisting of:

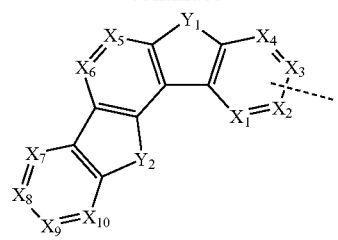

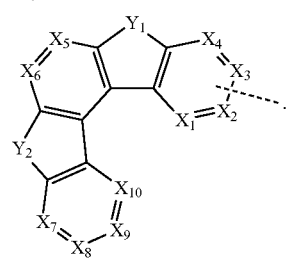

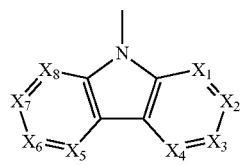

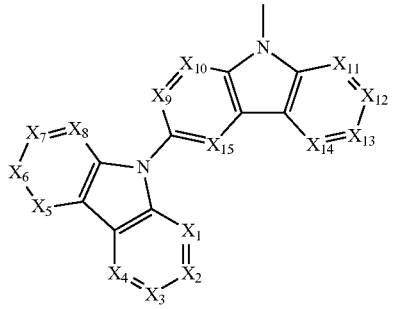

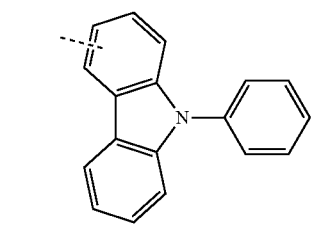

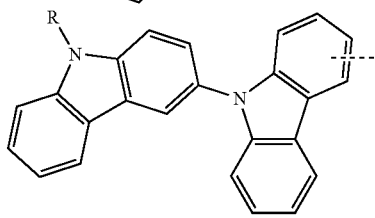

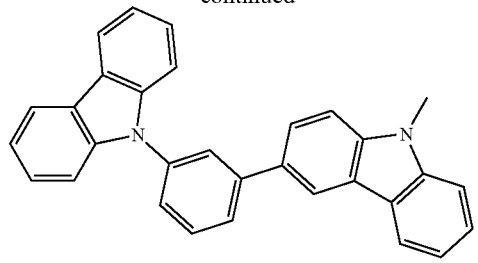
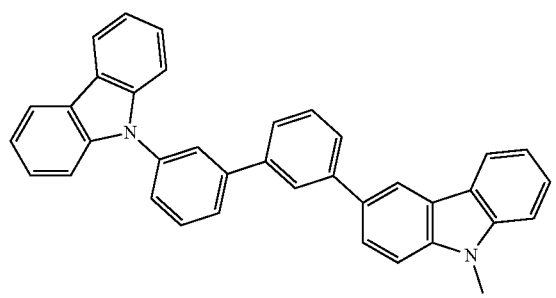
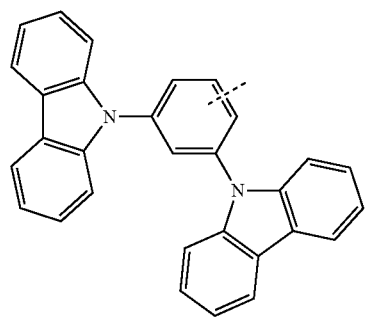
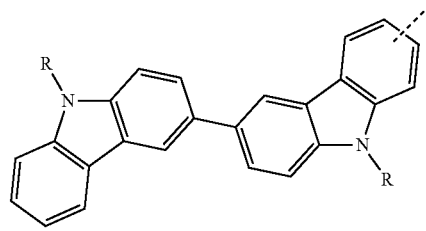
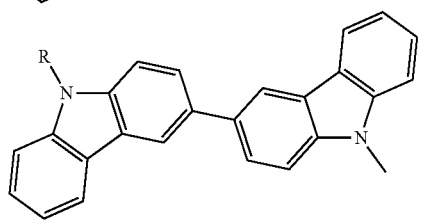
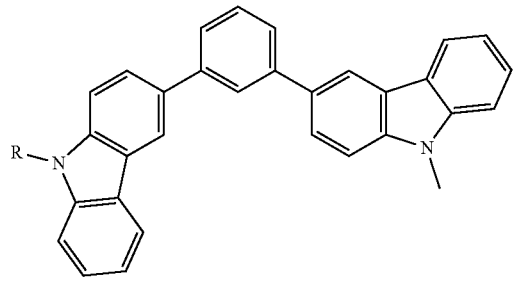
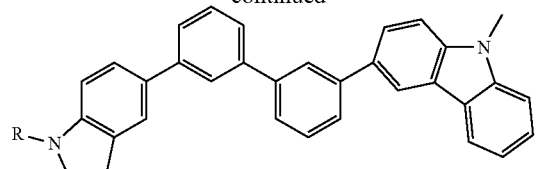
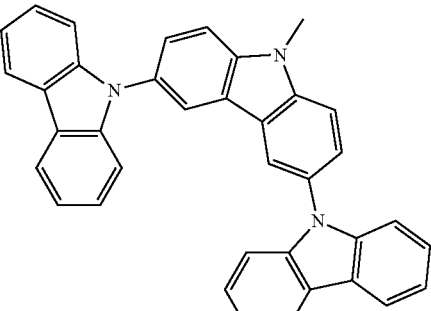
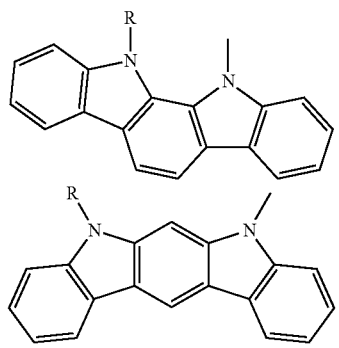
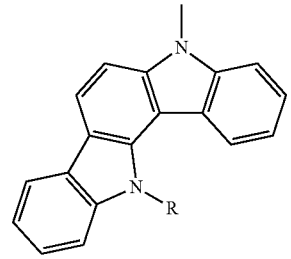
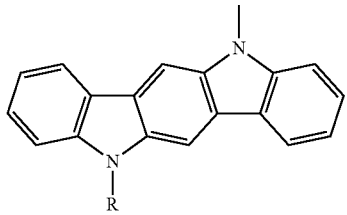
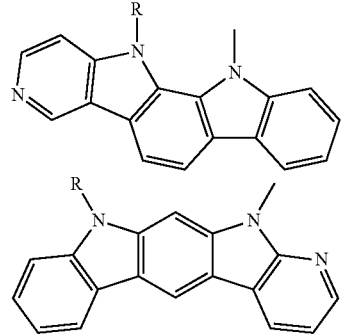

-continued

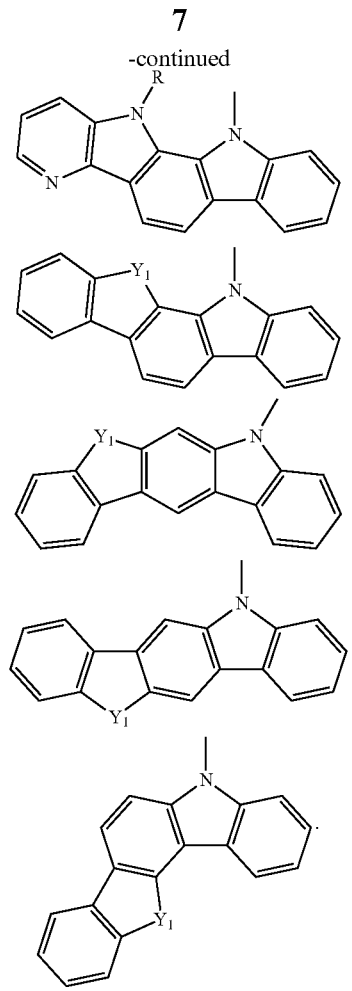

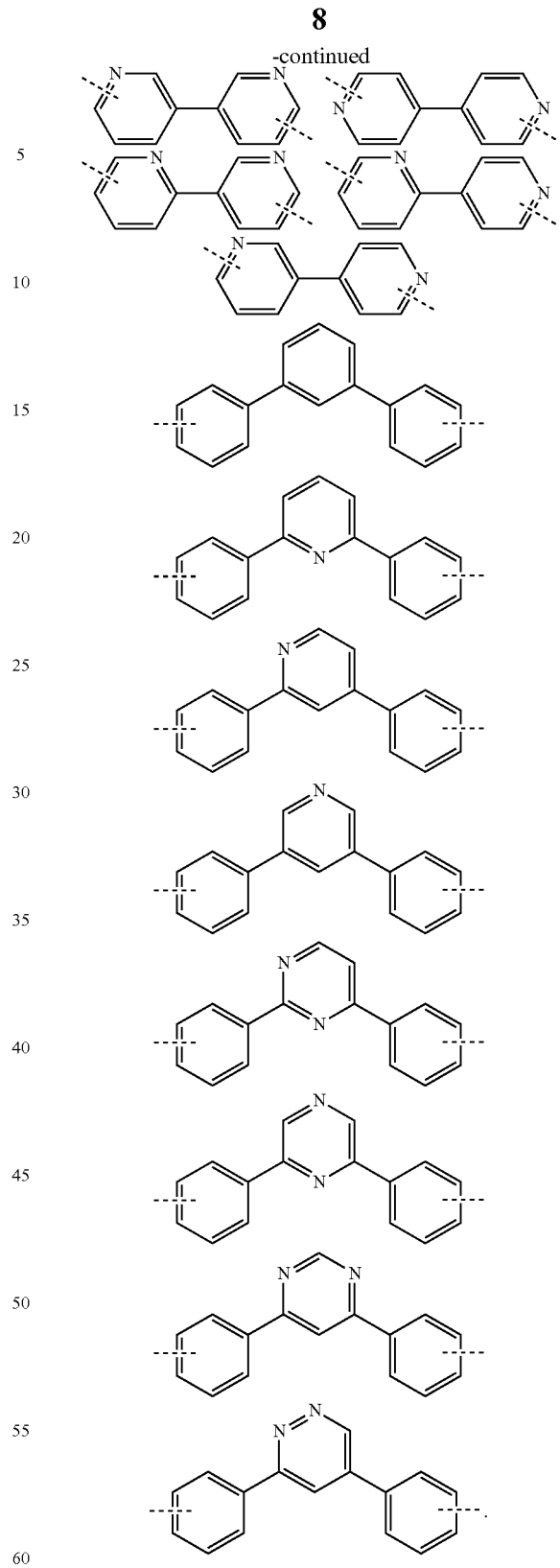

$Y_1$ and $Y_2$ are independently selected from the group consisting of O, S, and Se. $X_1$ to $X_{10}$ are independently selected from the group consisting of CR and N, and wherein each benzo ring contains at most one N. R is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $L_1$ and $L_2$ are independently selected from the group consisting of:

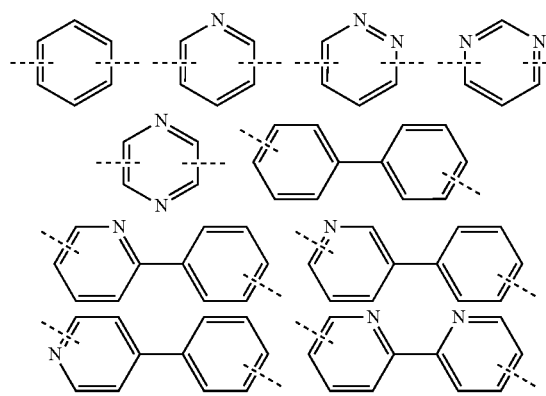

In one aspect, $L_2$ is a single bond. In another aspect, $L_1$ and $L_2$ contain at least one phenyl bonded directly to Z.

In one aspect, Ar and Ar' are phenyl. In another aspect, Ar, Ar', A and B are independently substituted with at least one group selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, "aryl" comprises phenyl, biphenyl, triphenyl, terphenyl, naphthalene, phenalene, phenanthrene, fluorene or chrysene, and in another aspect, "heteroaryl" comprises dibenzothiophene, dibenzofuran, benzofuran, benzothiophene, pyrazole, imidazole, triazole, oxazole, thiazole, oxadiazole, oxatriazole, dioxazole, thiadiazole, pyridine, pyridazine, pyrimidine, pyrazine, triazine, indole, azaindole, benzimidazole, indazole, benzoxazole, benzisoxazole, benzothiazole, quinoline, isoquinoline, cinnoline, quinazoline, quinoxaline, naphthyridine, phthalazine, pteridine, xanthene, phenothiazine, phenoxazine, benzofuropyridine, furodipyridine, benzothienopyridine and thienodipyridine.

Non-limiting compounds are provided. In one aspect, the compound of Formula I is selected from Compound 1-Compound 22. In Compound 1-Compound 22, $Y_1$ and $Y_2$ are independently selected from the group consisting of O, S and Se, and Z is selected from the group consisting of Si and Ge. In another aspect, the compound of Formula I is selected from Compound 23-Compound 38.

A first device is also provided. The first device comprises an organic light emitting device, and further comprises an anode, a cathode, and an organic layer, disposed between the anode and the cathode, comprising a compound having the Formula I:

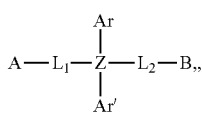

Formula I

Ar and Ar' are independently selected from the group consisting of phenyl, biphenyl, napthyl, dibenzothiolyl, and dibenzofuranyl, which are optionally further substituted. Z is selected from Si and Ge. $L_1$ comprises aryl or heteroaryl groups, and any heteroatoms in the heteroaryl groups are nitrogen. $L_2$ is a single bond or comprises aryl or heteroaryl groups, and any heteroatoms in the heteroaryl groups are nitrogen. $L_1$ and $L_2$ can be optionally further substituted.

Group A contains a group selected from the group consisting of dibenzofuran, dibenzothiophene, azadibenzofuran, azadibenzothiophene, dibenzoselenophene and azadibenzoselenophene, which are optionally further substituted, and wherein the substitution is optionally fused to at least one benzo ring. Group B contains a group selected from the group consisting of carbazole and azacarbazole, which are optionally further substituted, and wherein the substitution is optionally fused to the carbazole or azacarbazole group.

In one aspect, the organic layer is an emissive layer and the compound of formula I is a host. In another aspect, the organic layer further comprises an emissive dopant. In one aspect, the organic layer is deposited using a solution process. In one aspect, the emissive dopant is a transition metal complex having at least one ligand selected from the group consisting of:

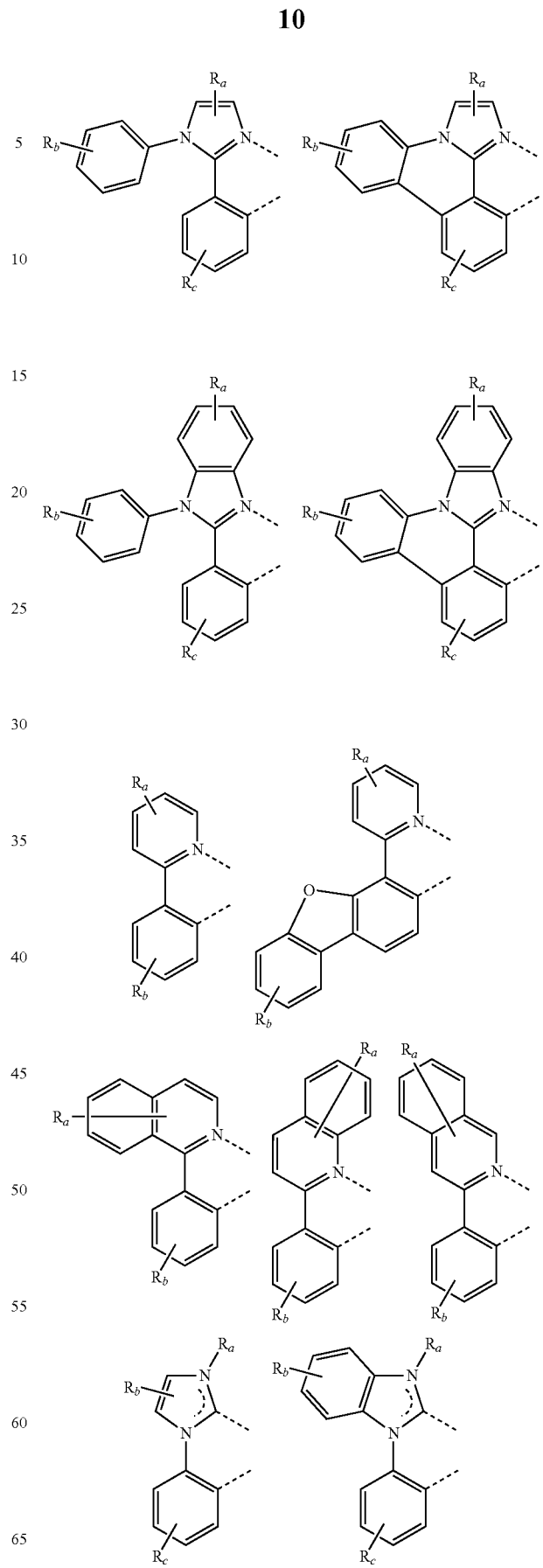

-continued

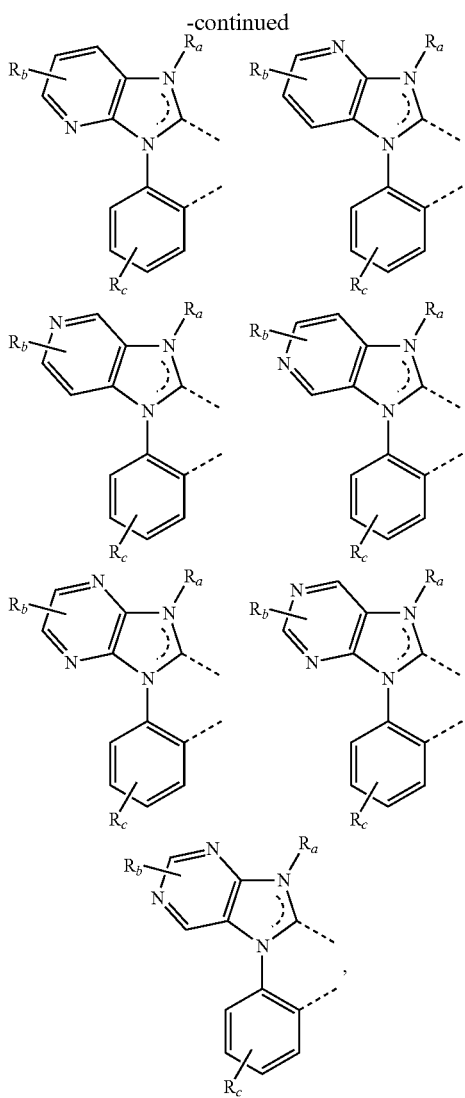

wherein $R_a$, $R_b$, and $R_c$ may represent mono, di, tri or tetra substitutions. $R_a$, $R_b$, and $R_c$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein two adjacent substituents of $R_a$, $R_b$, and $R_c$ are optionally joined to form a fused ring.

In one aspect, the device further comprises a second organic layer that is a non-emissive layer and the compound having Formula I is a material in the second organic layer. In another aspect, the second organic layer is a blocking layer and the compound having Formula I is a blocking material in the second organic layer.

In one aspect, the first device is a consumer product. In another aspect, the first device is an organic light-emitting device.

BRIEF DESCRIPTION OF THE DRAWINGS

FIG. 4 shows the layout of an OLED device.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
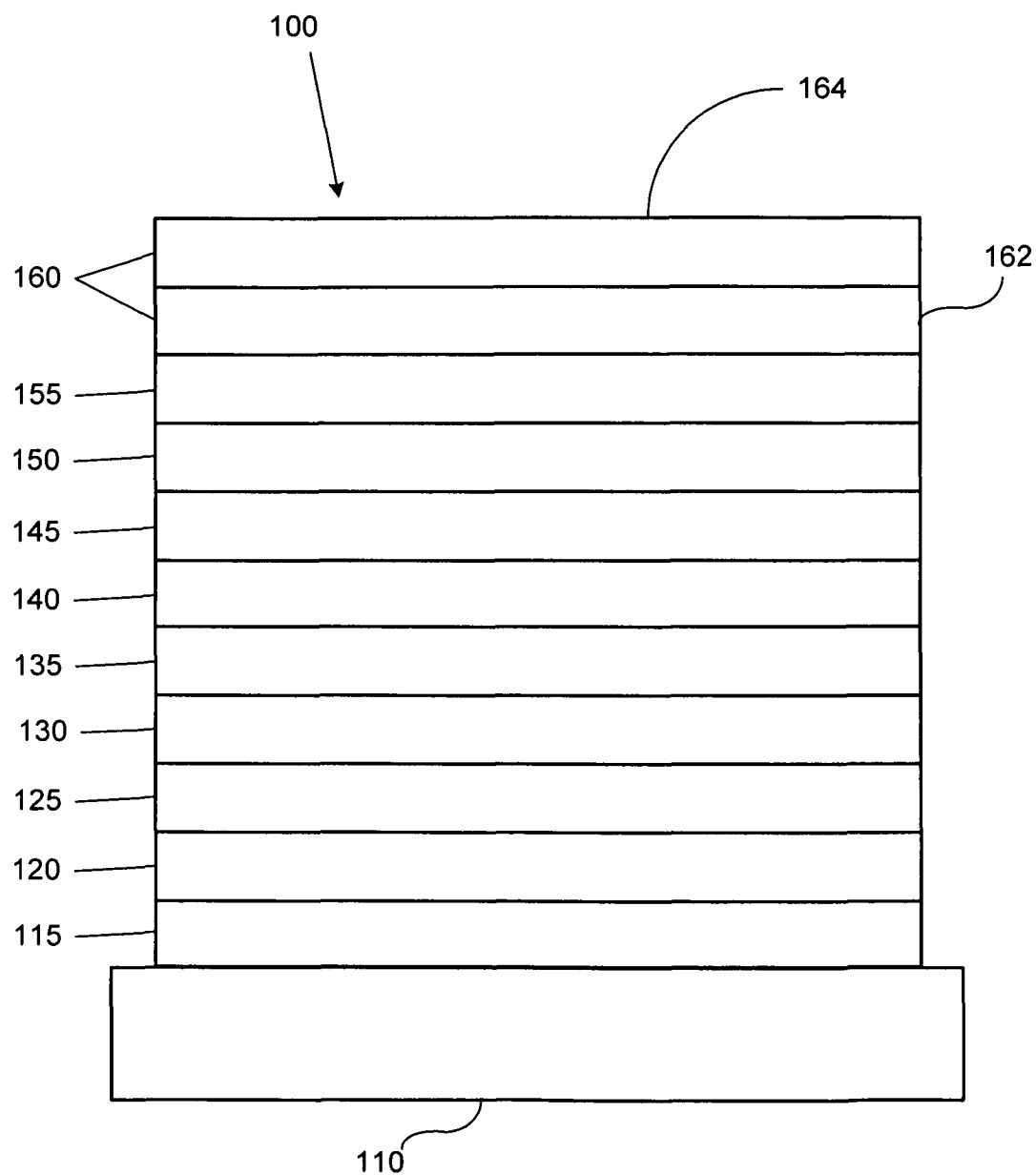
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No.

6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
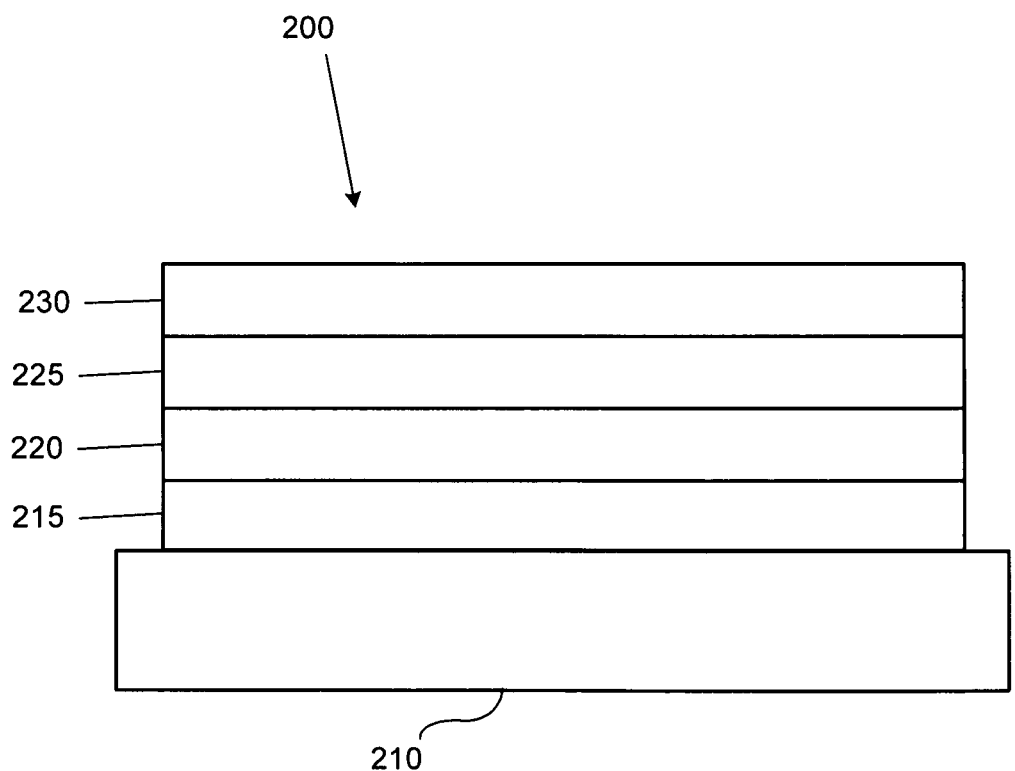
FIG. 2 shows an inverted organic light emitting device that does not have a separate electron transport layer.
Figure 3:
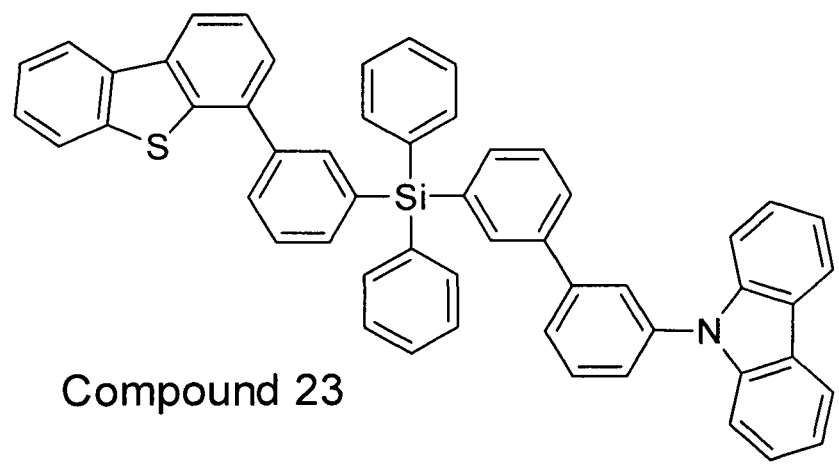
FIG. 3 shows a compound of Formula I.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

A compound of Formula I is provided.

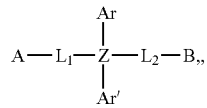

Formula I

In one embodiment, Ar and Ar' are independently selected from the group consisting of phenyl, biphenyl, napthyl, dibenzothiolyl, and dibenzofuranyl, which are optionally further substituted. Z is selected from Si and Ge. $L_1$ comprises aryl or heteroaryl groups, and any heteroatoms in the heteroaryl groups are nitrogen. $L_2$ is a single bond or comprises aryl or heteroaryl groups, and any heteroatoms in the heteroaryl groups are nitrogen. $L_1$ and $L_2$ can be optionally further substituted. In one embodiment, the substituents on $L_1$, $L_2$, Ar, and Ar' can be hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

An "aryl" group is an aromatic all carbon group, which can contain one or more fused rings within it. Merely by way of example, and without any limitation, exemplary aryl groups can be phenyl, naphthalene, phenanthrene, corannulene, etc. A "heteroaryl" group is an "aryl" group containing at least one heteroatom. Merely by way of example, and without any limitation, exemplary heteroaryl groups can be pyridine, quinoline, phenanthroline, azacorannulene, etc. Both "aryl" and "heteroaryl" groups in $L_1$ and $L_2$ can have multiple attachment points connecting them to other fragments. $L_1$ and $L_2$ can contain any desired number of aryl or heteroaryl groups.

Group A contains a group selected from the group consisting of dibenzofuran, dibenzothiophene, azadibenzofuran, azadibenzothiophene, dibenzoselenophene and azadibenzoselenophene, which are optionally further substituted, and wherein the substitution is optionally fused to at least one benzo ring. Group B contains a group selected from the group consisting of carbazole and azacarbazole, which are optionally further substituted, and wherein the substitution is optionally fused to the carbazole or azacarbazole group.

In one embodiment, A is selected from the group consisting of:

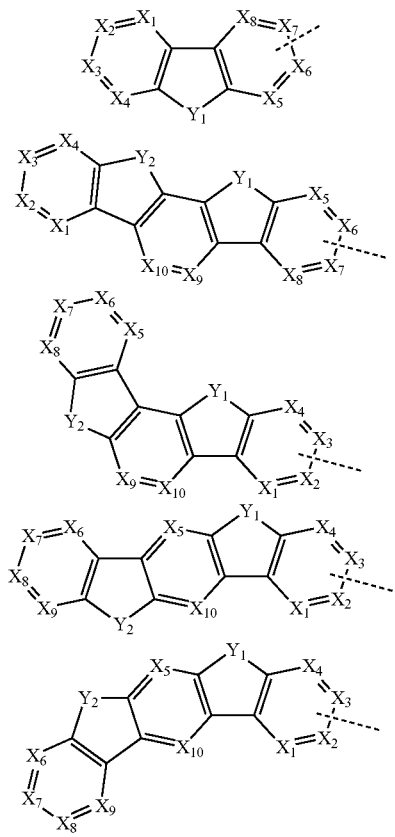

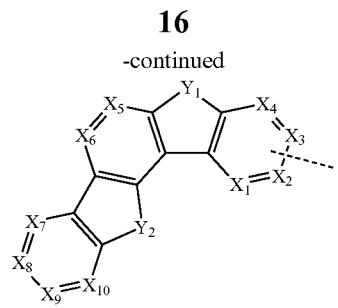

In another embodiment, B is selected from the group consisting of:

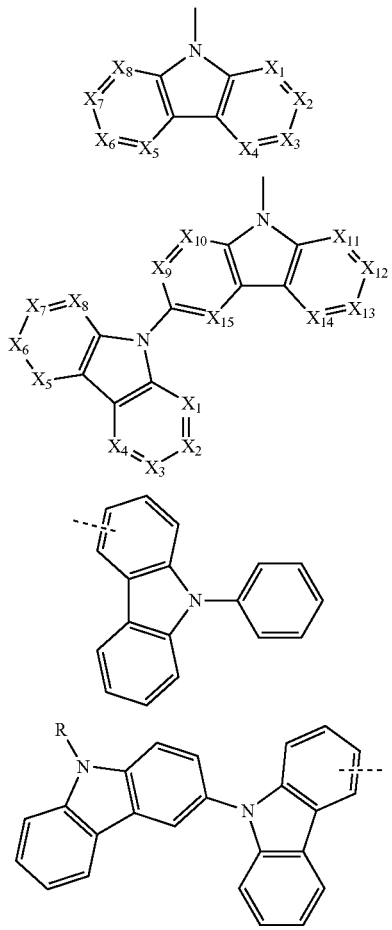

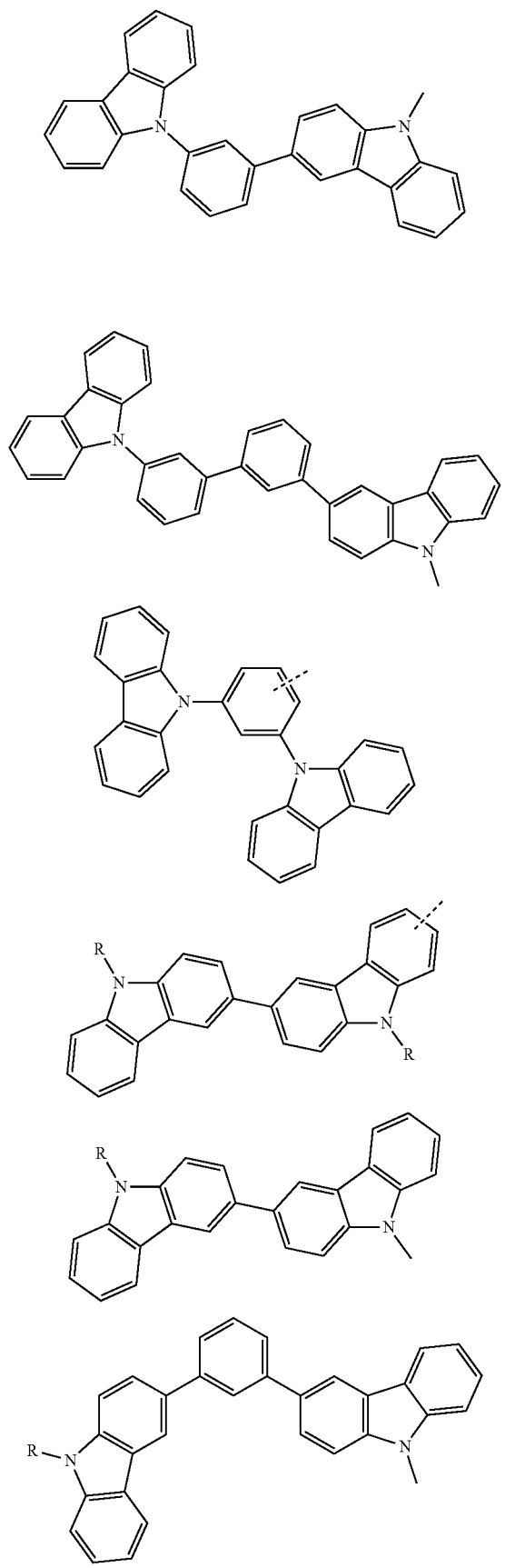
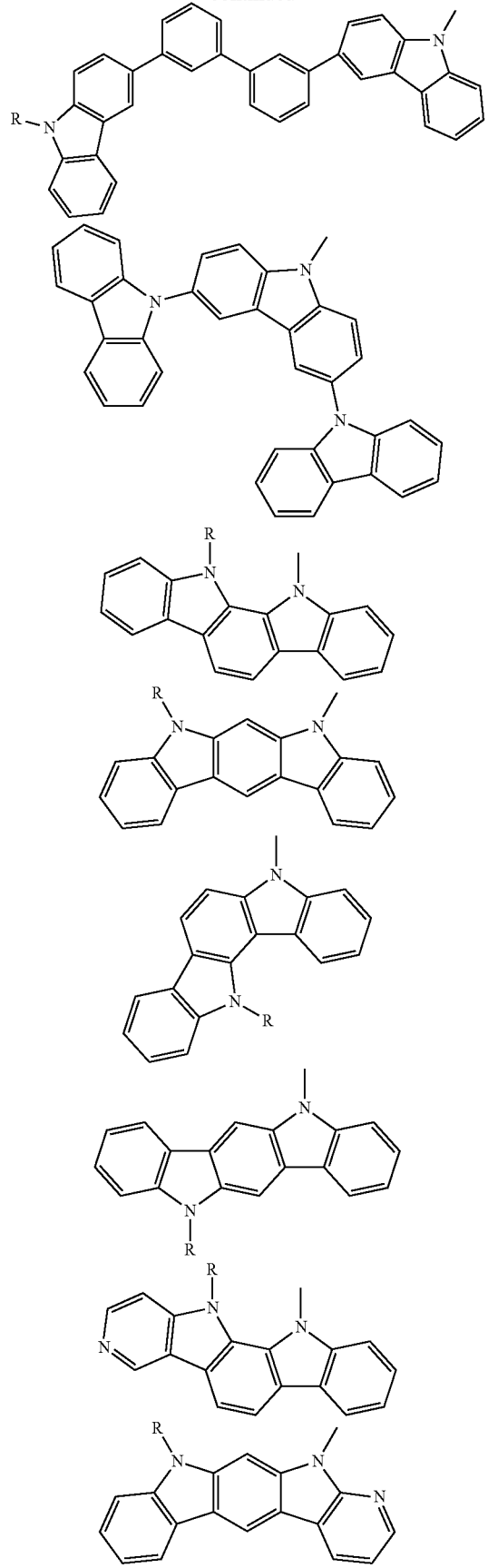

-continued

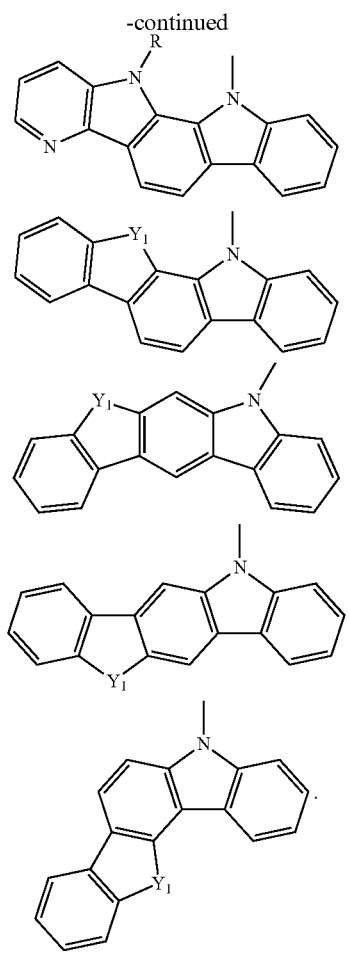

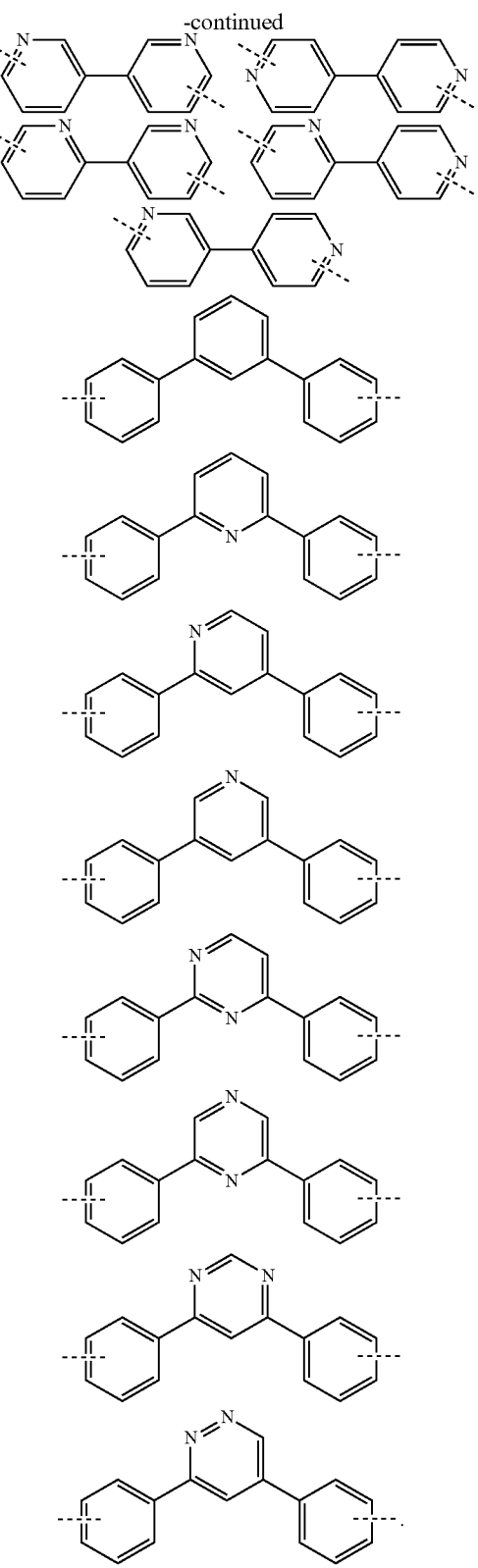

Y₁ and Y₂ are independently selected from the group consisting of O, S, and Se. $X_1$ to $X_{10}$ are independently selected from the group consisting of CR and N, and wherein each benzo ring contains at most one N. R is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one embodiment, $L_1$ and $L_2$ are independently selected from the group consisting of:

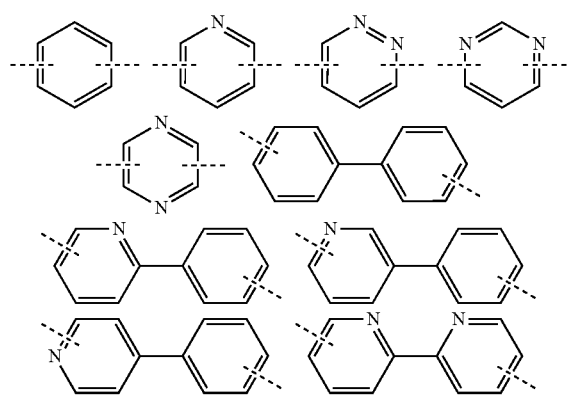

In one embodiment, $L_2$ is a single bond. In another embodiment, $L_1$ and $L_2$ contain at least one phenyl bonded directly to Z. The dashed lines in the chemical structures disclosed herein represent a bond through any position on that group capable of forming a single bond with another atom.

In one embodiment, Ar and Ar' are phenyl. In another embodiment, Ar, Ar', A and B are independently substituted with at least one group selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one embodiment, "aryl" comprises phenyl, biphenyl, triphenyl, terphenyl, naphthalene, phenalene, phenanthrene, fluorene or chrysene, and in another embodiment, "heteroaryl" comprises dibenzothiophene, dibenzofuran, benzofuran, benzothiophene, pyrazole, imidazole, triazole, oxazole, thiazole, oxadiazole, oxatriazole, dioxazole, thiadiazole, pyridine, pyridazine, pyrimidine, pyrazine, triazine, indole, azaindole, benzimidazole, indazole, benzoxazole, benzisoxazole, benzothiazole, quinoline, isoquinoline, cinnoline, quinazoline, quinoxaline, naphthyridine, phthalazine, pteridine, xanthene, phenothiazine, phenoxazine, benzofuropyridine, furodipyridine, benzothienopyridine and thienodipyridine.

The novel compounds of Formula I disclosed herein contain of two different moieties, groups A and B, connected with an arylsilane or arylgermane spacer, resulting in an asymmetric structure. By "asymmetric" it is meant that groups A and B, as described above, have different structures. The compounds of Formula I have a number of advantageous properties when used in OLED devices. Firstly, inclusion of two distinct moieties allows fine-tuning the energy levels of the resultant compound, which may facilitate charge injection from adjacent layers and modulate charge trapping by the emitter dopants. Secondly, the two different moieties can be independently selected to have as electron and/or hole transport properties, yielding compounds with bipolar charge transport characteristics. These characteristics may not only suppresses operation voltage but also balance electron and hole fluxes to achieve an extended charge recombination zone. Thirdly, the arylsilane and arylgermane spacers break the conjugation between groups A and B, retaining high triplet energy for the entire molecule, and thus effectively reducing quenching.

The compounds of Formula I have additional advantages over known symmetric analogs because compounds of Formula I are less prone to crystallization. As a result, compounds of Formula I possess improved film uniformity, which, without being bound by theory, is believed to be a result of reduction in phase separation between the emitters and host materials. The novel compounds of Formula I can be used to improve OLED device performance parameters, such as emission spectrum line shape, efficiency and lifetime. Furthermore, compounds of Formula I also tend to be soluble in organic solvents such as toluene, xylene, and 3-phenoxytoluene, and are amenable to solution processing which is highly desirable for low-cost lighting applications.

In one embodiment, the compound of Formula I is selected from the group consisting of:

Compound 1

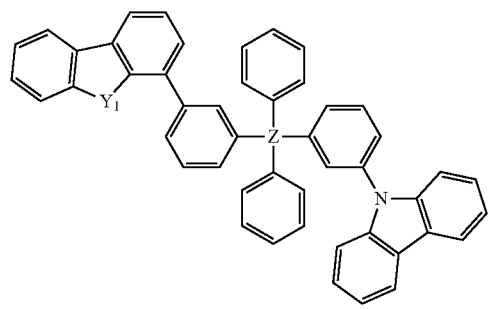

Compound 2

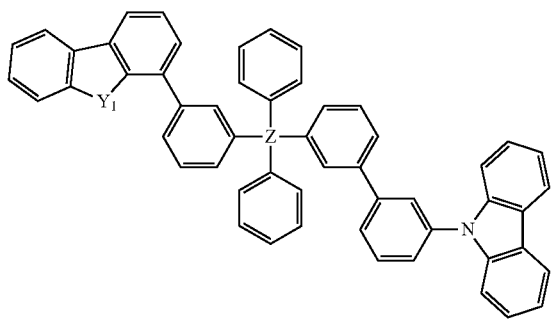

Compound 3

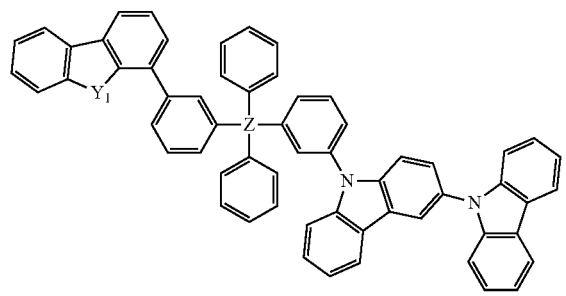

Compound 4

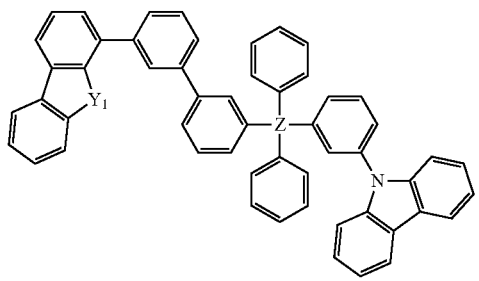

Compound 5
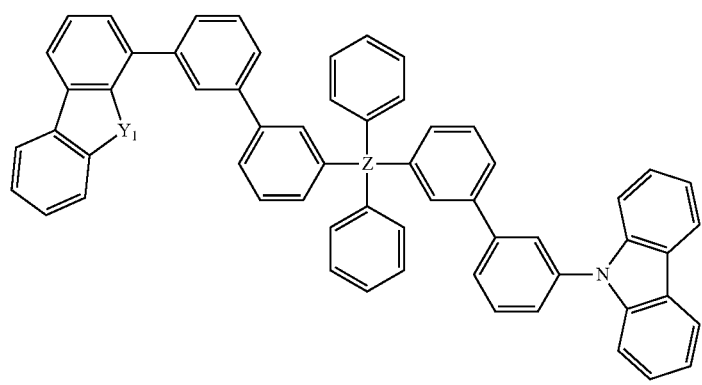
Compound 6
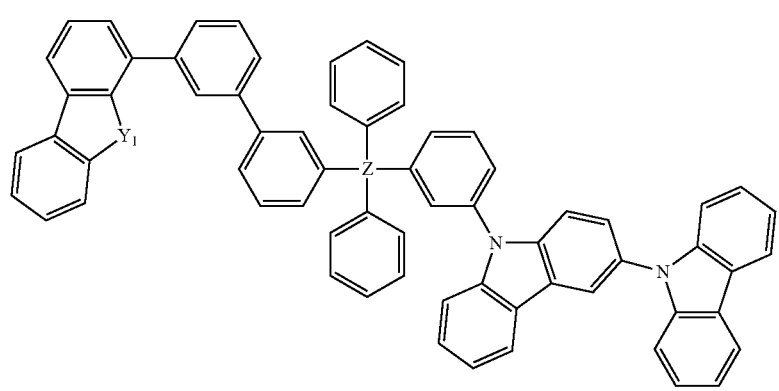
Compound 7
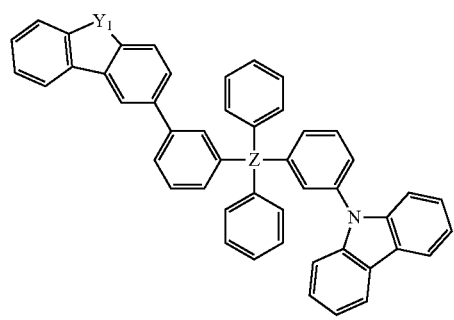
Compound 8
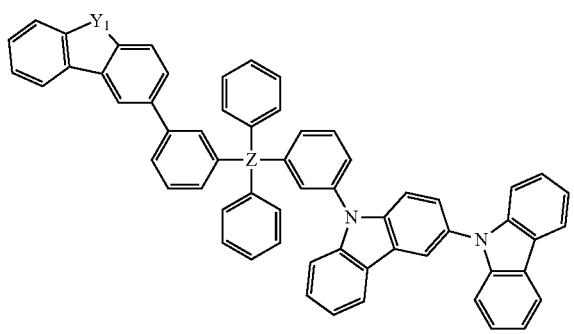
Compound 9
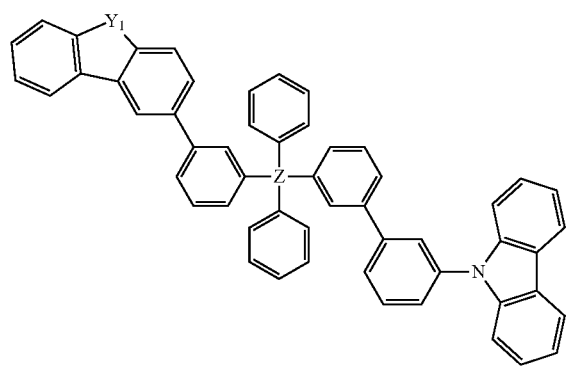
Compound 10
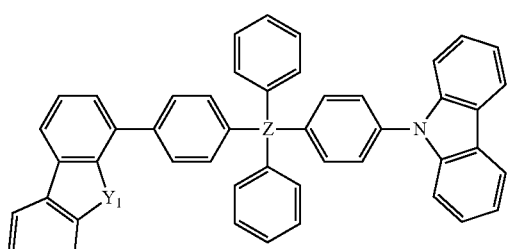

-continued
Compound 11
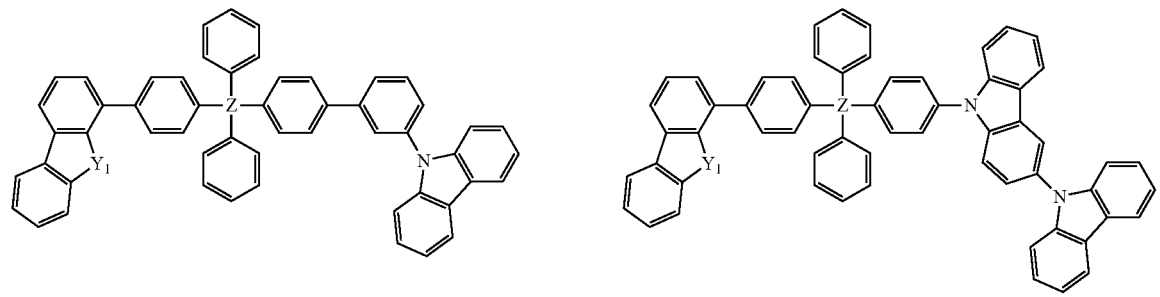
Compound 12
Compound 13
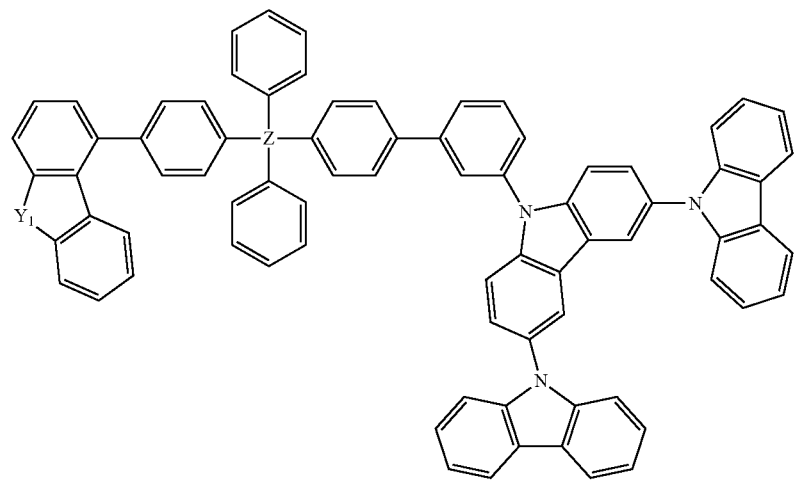
Compound 14
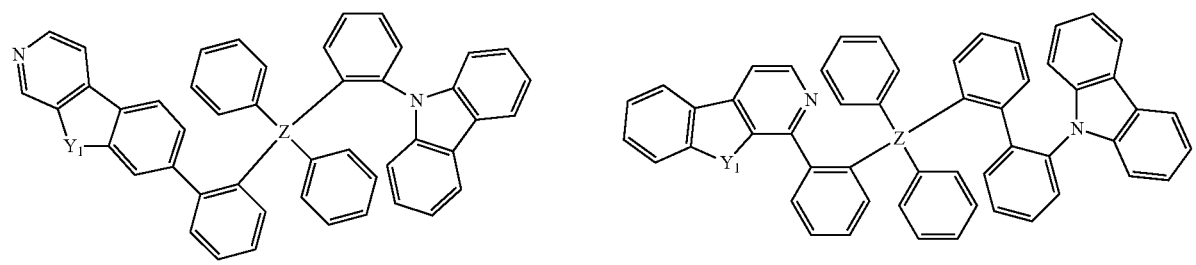
Compound 15
Compound 16
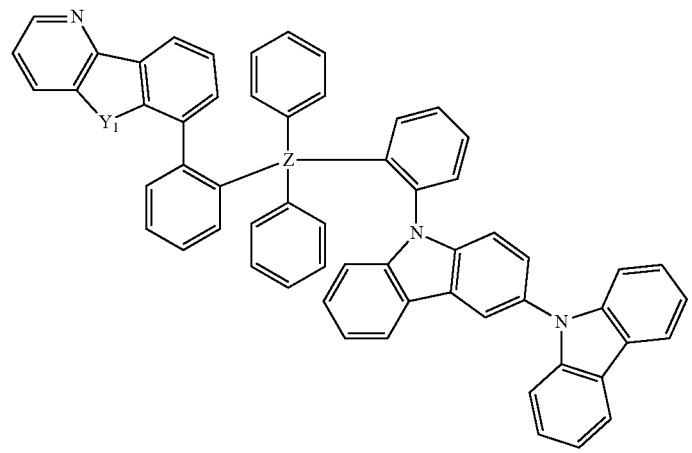

Compound 17
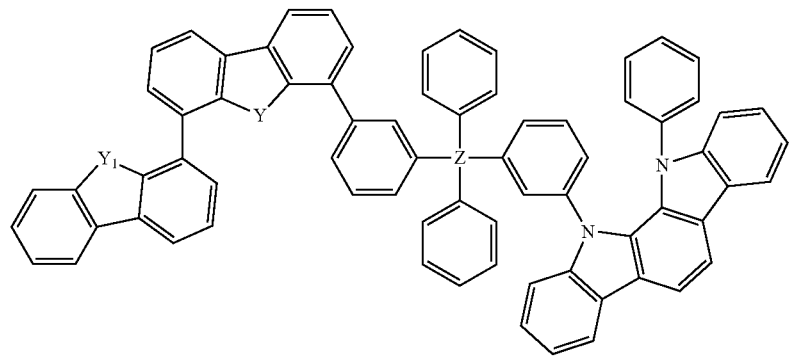
Compound 18
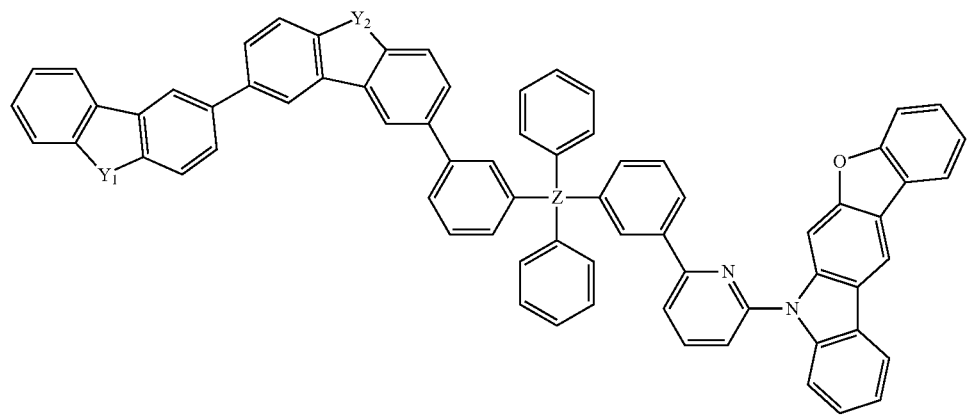
Compound 19
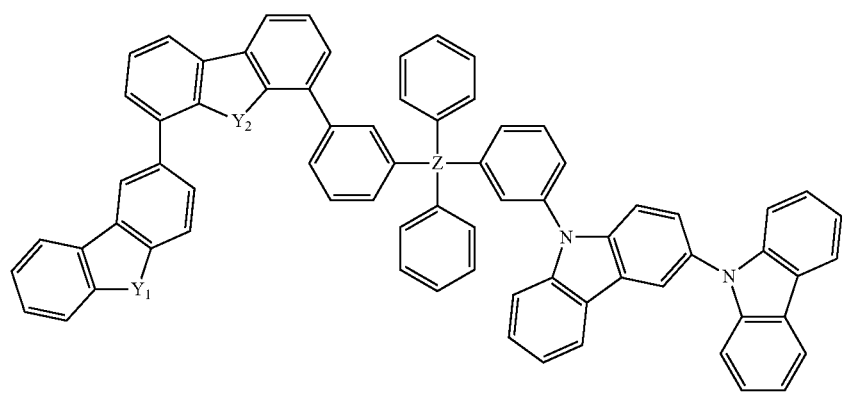
Compound 20
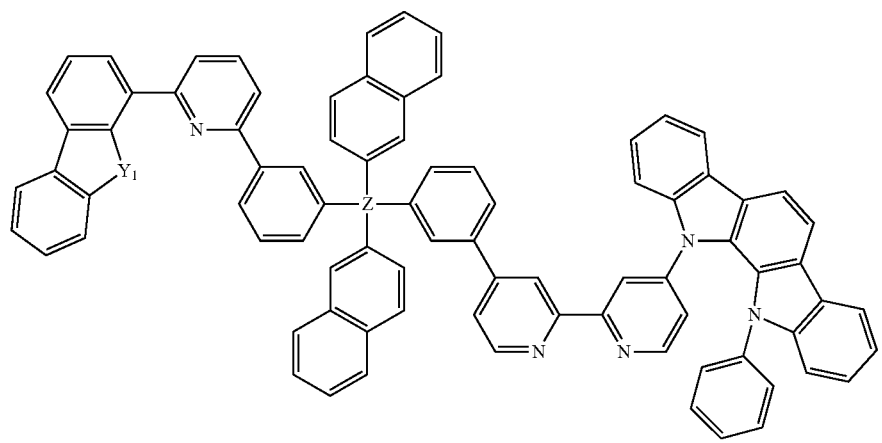

-continued
Compound 21
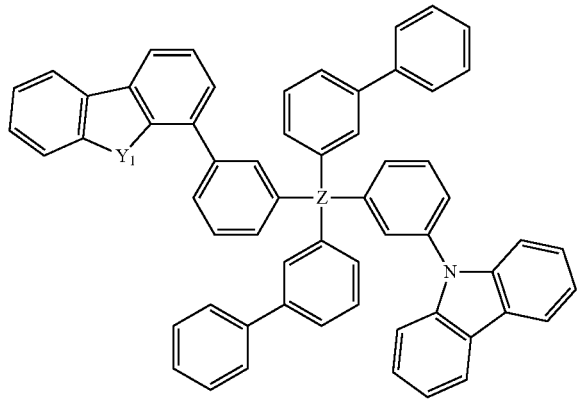
Compound 22
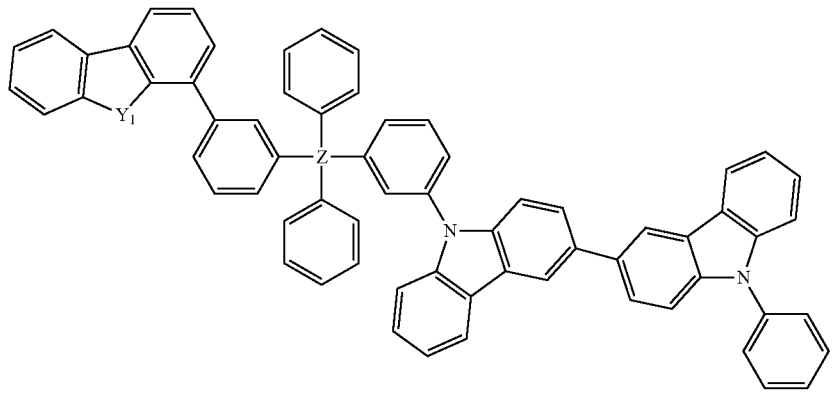
$Y_1$ and $Y_2$ are independently selected from the group consisting of O, S and Se. Z is selected from the group consisting of Si and Ge.
In another embodiment, the compound of Formula I is selected from the group consisting of:
Compound 23
Compound 24
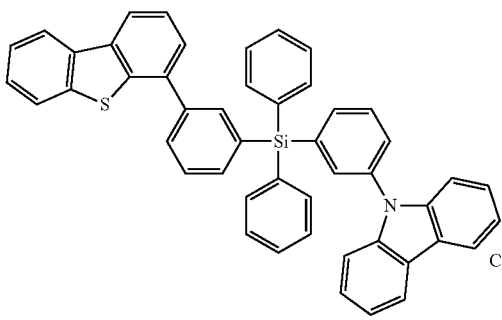
Compound 25
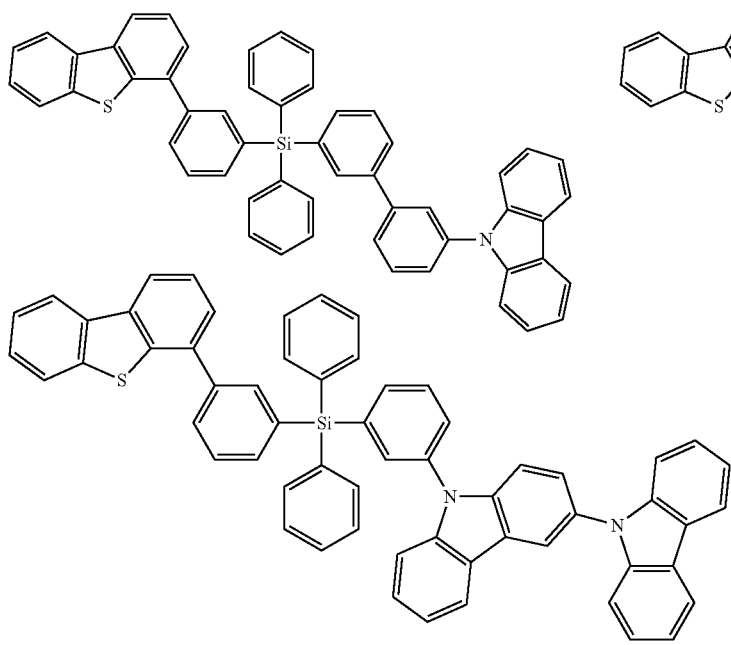

-continued
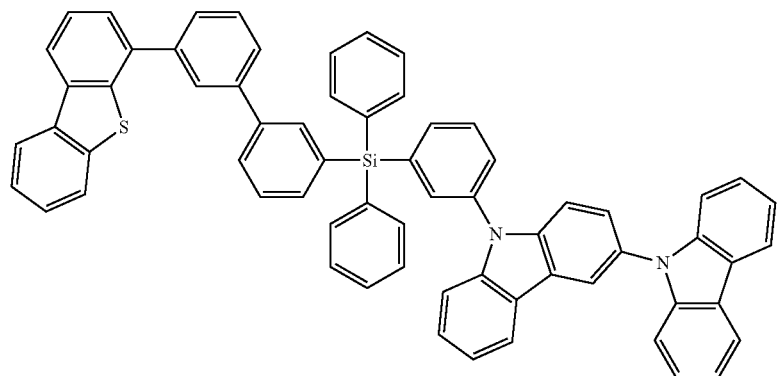
Compound 26
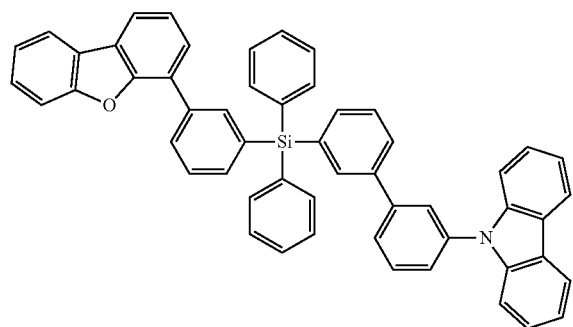
Compound 27
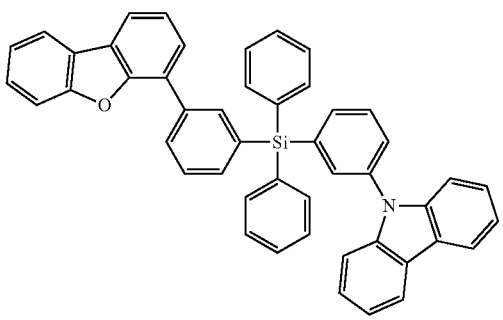
Compound 28
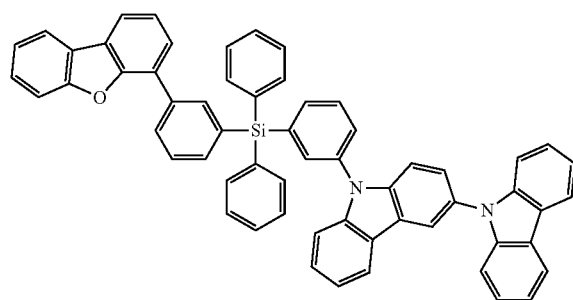
Compound 29
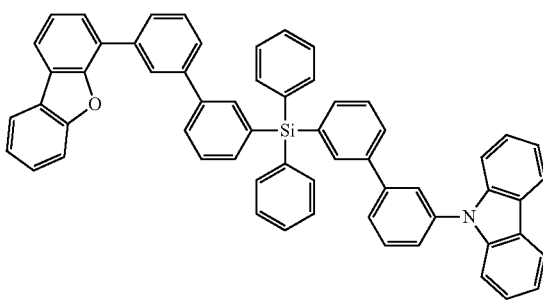
Compound 30
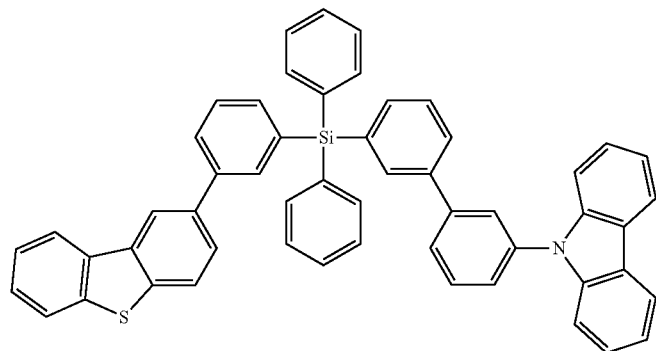
Compound 31

Compound 32
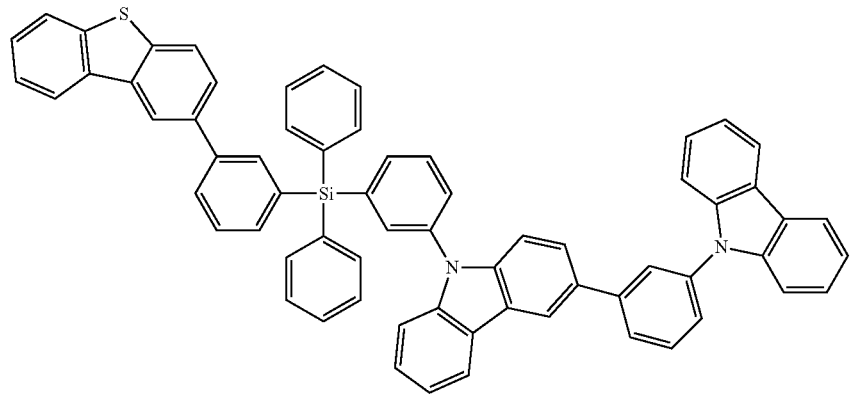
Compound 33
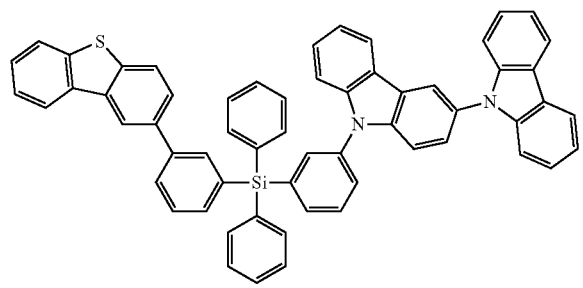
Compound 34
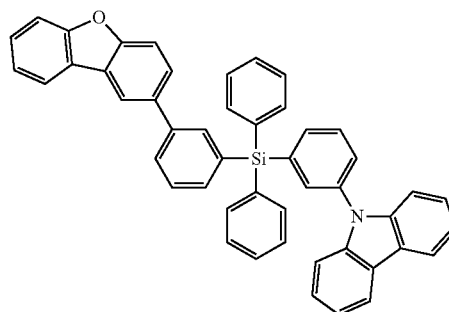
Compound 35
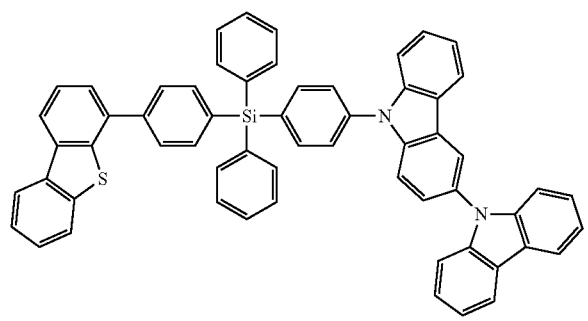
Compound 36
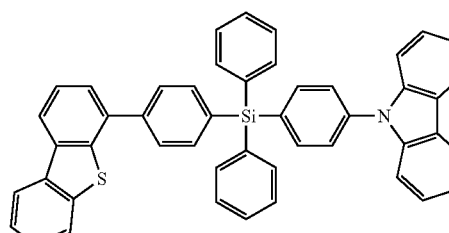
Compound 37
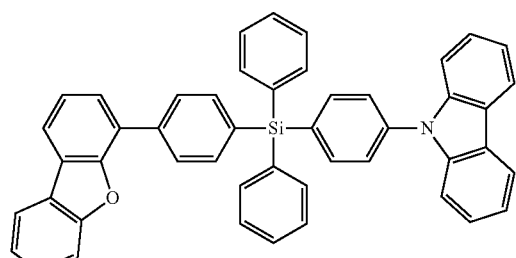
Compound 38
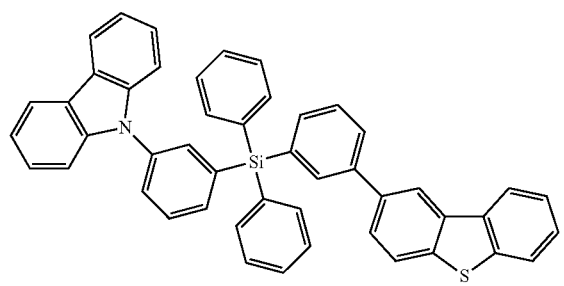

A first device is also provided. The first device comprises an organic light emitting device, and further comprises an anode, a cathode, and an organic layer, disposed between the anode and the cathode, comprising a compound having the Formula I:

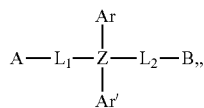

Formula I

Ar and Ar' are independently selected from the group consisting of phenyl, biphenyl, napthyl, dibenzothiolyl, and dibenzofuranyl, which are optionally further substituted. Z is selected from Si and Ge. $L_1$ comprises aryl or heteroaryl groups, and any heteroatoms in the heteroaryl groups are nitrogen. $L_2$ is a single bond or comprises aryl or heteroaryl groups, and any heteroatoms in the heteroaryl groups are nitrogen. $L_1$ and $L_2$ can be optionally further substituted. In one embodiment, the substituents on $L_1$, $L_2$, Ar, and Ar' can be hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

Group A contains a group selected from the group consisting of dibenzofuran, dibenzothiophene, azadibenzofuran, azadibenzothiophene, dibenzoselenophene and azadibenzoselenophene, which are optionally further substituted, and wherein the substitution is optionally fused to at least one benzo ring. Group B contains a group selected from the group consisting of carbazole and azacarbazole, which are optionally further substituted, and wherein the substitution is optionally fused to the carbazole or azacarbazole group.

In one embodiment, the organic layer is an emissive layer and the compound of Formula I is a host. In another embodiment, the organic layer further comprises an emissive dopant. In one embodiment, the emissive dopant is a transition metal complex having at least one ligand selected from the group consisting of:

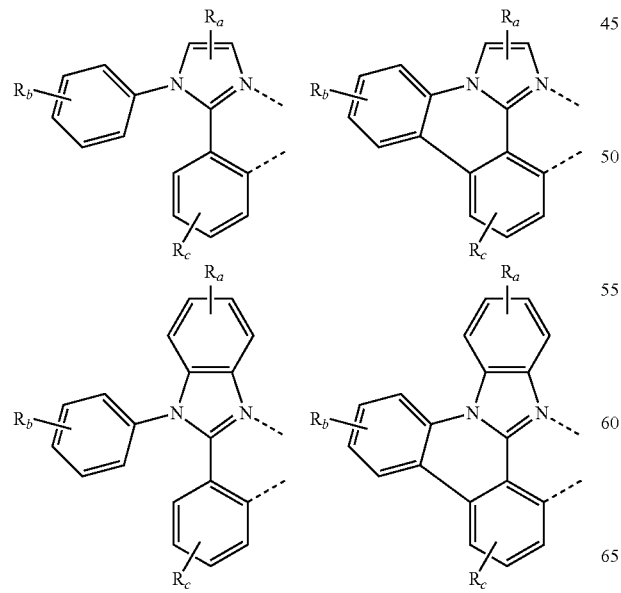

-continued

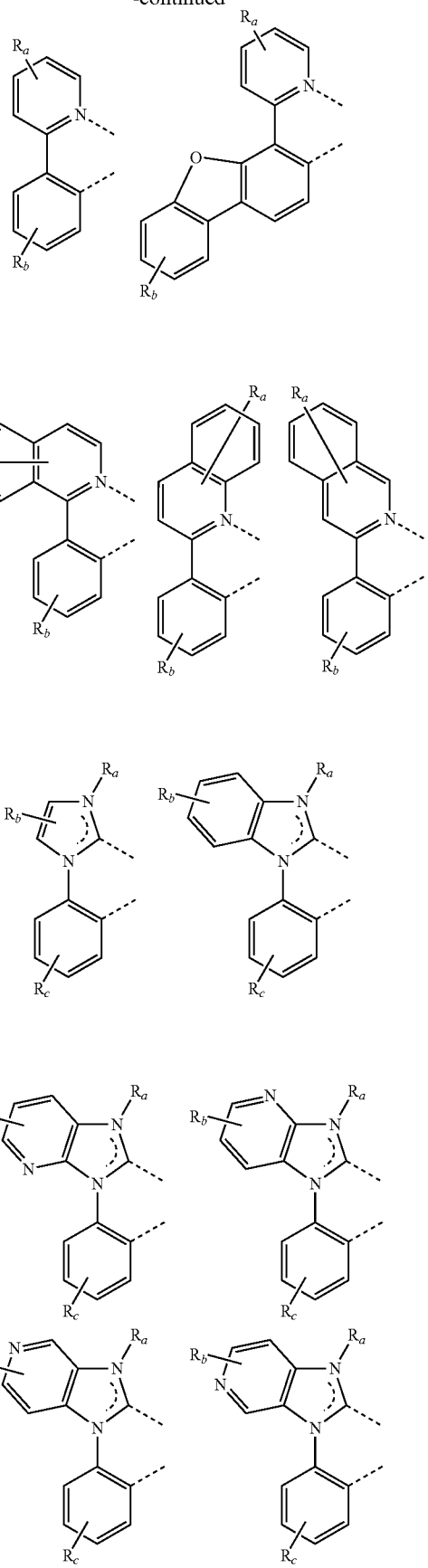

-continued

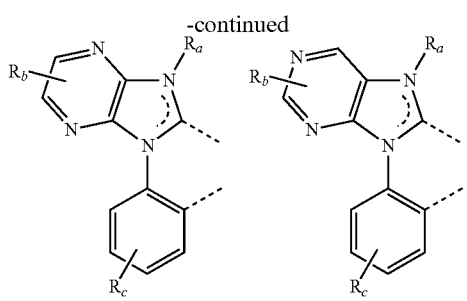

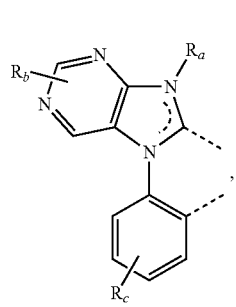

wherein $R_a$, $R_b$, and $R_c$ may represent mono, di, tri or tetra substitutions. $R_a$, $R_b$, and $R_c$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein two adjacent substituents of $R_a$, $R_b$, and $R_c$ are optionally joined to form a fused ring.

In one embodiment, the device further comprises a second organic layer that is a non-emissive layer and the compound having Formula I is a material in the second organic layer. In another embodiment, the second organic layer is a blocking layer and the compound having Formula I is a blocking material in the second organic layer. In one embodiment, the organic layer is deposited using a solution process.

In one embodiment, the first device is a consumer product. In another embodiment, the first device is an organic light-emitting device.

Device Examples

The structures of the materials used in the device examples is show in Table 1 below.

TABLE 1

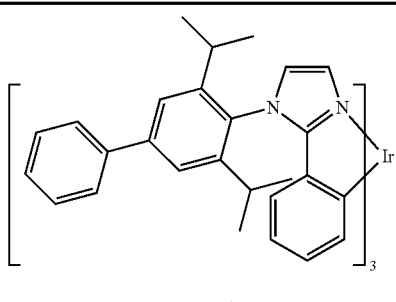

Compound D

TABLE 1-continued

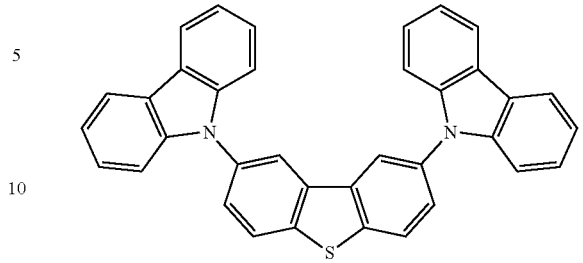

Compound BL

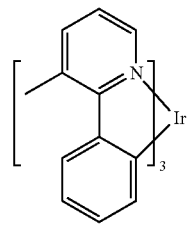

Compound HIL

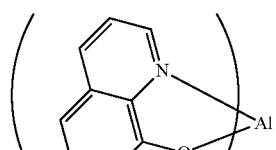

Alq

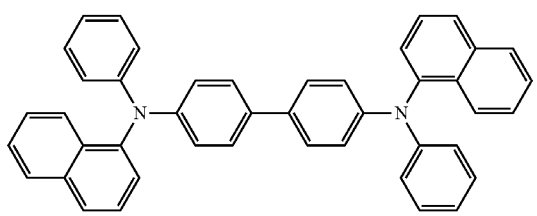 [SMILES: c1ccc(N(c2ccc(-c3ccc(N(c4ccccc4)c4cccc5ccccc45)cc3)cc2)c2cccc3ccccc23)cc1]

Compound NPD

The organic stack of the OLED device used in the Examples and Comparative Device Examples has the following structure: from the ITO surface, 100 Å of Compound HIL as the hole injection layer, 300 Å of NPD as the hole transporting layer (HTL), 300 Å of a compound of Formula I, CC-1 or CC-2 doped with 15 wt % of Compound D as the emissive layer (EML), 50 Å of Compound BL as the Blocking Layer (BL) and 400 Å of Alq as the ETL1. The device structure is shown in FIG. 4.

Comparative Compounds CC-1 and CC-2 have the following structures:

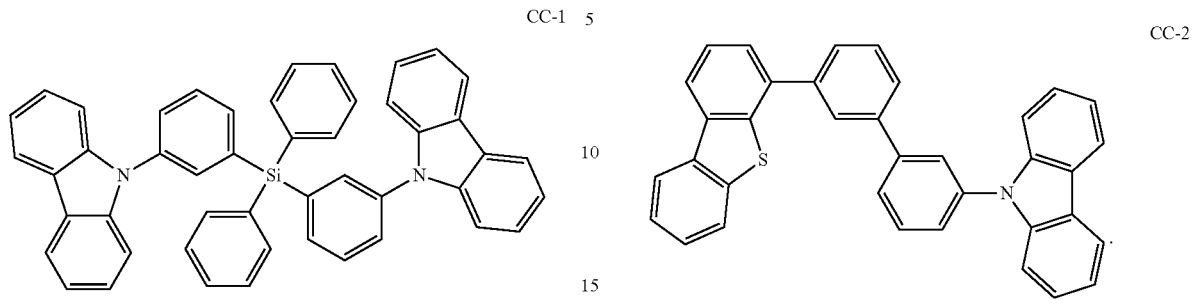

TABLE 2

| Example | Host | BL | 1931 CIE x | 1931 CIE y | λ$_{max}$ [nm] | At 1000 nits V [V] | At 1000 nits LE [cd/A] | At 1000 nits EQE [%] | At 1000 nits PE [lm/W] | At 20 mA/cm$^2$ LT$_{80\%}$ [h] |
|---|---|---|---|---|---|---|---|---|---|---|
| Device Example 1 | Compound 23 | Compound BL | 0.179 | 0.391 | 474 | 7.4 | 37.8 | 16.6 | 16.1 | 76 |
| Device Example 2 | Compound 24 | Compound BL | 0.172 | 0.376 | 474 | 6.7 | 43 | 19.6 | 20.2 | 86 |
| Device Example 3 | Compound 25 | Compound BL | 0.179 | 0.395 | 474 | 6.5 | 43.1 | 18.9 | 20.7 | 90 |
| Device Example 4 | Compound 26 | Compound BL | 0.175 | 0.389 | 474 | 6.5 | 44.6 | 19.8 | 21.4 | 81 |
| Device Example 5 | Compound 27 | Compound BL | 0.178 | 0.392 | 474 | 7.2 | 38.5 | 17.0 | 16.8 | 83 |
| Device Example 6 | Compound 28 | Compound BL | 0.176 | 0.385 | 474 | 6.7 | 43.1 | 19.2 | 20.2 | 100 |
| Device Example 7 | Compound 29 | Compound BL | 0.173 | 0.378 | 474 | 7.3 | 40.8 | 18.5 | 17.5 | 70 |
| Device Example 8 | Compound 30 | Compound BL | 0.174 | 0.380 | 474 | 6.7 | 43.7 | 19.8 | 20.5 | 55 |
| Device Example 9 | Compound 31 | Compound BL | 0.176 | 0.389 | 474 | 6.4 | 47.3 | 21.0 | 23.2 | 63 |
| Device Example 10 | Compound 32 | Compound BL | 0.177 | 0.394 | 474 | 6.8 | 43 | 19.0 | 19.8 | 34 |
| Device Example 11 | Compound 33 | Compound BL | 0.183 | 0.408 | 474 | 6.9 | 39.9 | 17.1 | 18.2 | 58 |
| Device Example 12 | Compound 34 | Compound BL | 0.176 | 0.386 | 474 | 6.6 | 42 | 18.7 | 19.9 | 72 |
| Device Example 13 | Compound 35 | Compound BL | 0.182 | 0.410 | 476 | 6.6 | 44.1 | 18.8 | 21.0 | 35 |
| Device Example 14 | Compound 36 | Compound BL | 0.179 | 0.405 | 474 | 6.7 | 46.3 | 20.0 | 21.8 | 37 |
| Device Example 15 | Compound 37 | Compound BL | 0.179 | 0.394 | 474 | 6.7 | 42.5 | 18.7 | 20.0 | 43 |
| Device Example 16 | Compound 38 | Compound BL | 0.176 | 0.387 | 474 | 6.5 | 45.7 | 20.3 | 22.0 | 55 |
| Device Example 17 | Compound 23 | Compound 23 | 0.174 | 0.385 | 472 | 7.1 | 43 | 19.2 | 19.1 | 75 |
| Device Example 18 | Compound 24 | Compound 24 | 0.171 | 0.371 | 474 | 7.5 | 41.3 | 19.0 | 17.2 | 80 |
| Device Example 19 | Compound 25 | Compound 25 | 0.177 | 0.389 | 474 | 7.6 | 40.5 | 17.9 | 16.8 | 78 |
| Device Example 20 | Compound 26 | Compound 26 | 0.186 | 0.426 | 476 | 9.6 | 43.7 | 18.1 | 14.3 | 83 |
| Device Example 21 | Compound 27 | Compound 27 | 0.176 | 0.387 | 474 | 8.2 | 40.1 | 17.8 | 15.4 | 87 |
| Device Example 22 | Compound 28 | Compound 28 | 0.174 | 0.380 | 474 | 7.5 | 43.1 | 19.4 | 18.0 | 86 |
| Device Example 23 | Compound 29 | Compound 29 | 0.173 | 0.378 | 474 | 7.3 | 40.8 | 18.5 | 17.5 | 67 |
| Device Example 24 | Compound 30 | Compound 30 | 0.172 | 0.376 | 474 | 7.6 | 43.3 | 19.7 | 17.9 | 47 |
| Device Example 25 | Compound 31 | Compound 31 | 0.174 | 0.383 | 474 | 7.4 | 42.2 | 19.0 | 17.9 | 60 |
| Device Example 26 | Compound 32 | Compound 32 | 0.175 | 0.390 | 474 | 8.2 | 40.1 | 17.9 | 15.4 | 30 |

TABLE 2-continued

| | | | 1931 CIE | | $\lambda_{max}$ | At 1000 nits | | | | At 20 mA/cm² |
|---|---|---|---|---|---|---|---|---|---|---|
| | | | | | | V | LE | EQE | PE | |
| Example | Host | BL | x | y | [nm] | [V] | [cd/A] | [%] | [lm/W] | $LT_{80\%}$ [h] |
| Device Example 27 | Compound 33 | Compound 33 | 0.180 | 0.402 | 474 | 8.6 | 37.5 | 16.3 | 13.7 | 125 |
| Device Example 28 | Compound 34 | Compound 34 | 0.173 | 0.380 | 474 | 8.3 | 39.7 | 17.9 | 15.1 | 88 |
| Device Example 29 | Compound 35 | Compound 35 | 0.181 | 0.408 | 476 | 7.1 | 43.6 | 18.8 | 19.3 | 33 |
| Device Example 30 | Compound 36 | Compound 36 | 0.177 | 0.402 | 474 | 7.2 | 46.3 | 20.1 | 20.2 | 39 |
| Device Example 31 | Compound 37 | Compound 37 | 0.177 | 0.390 | 474 | 7.1 | 43 | 19.1 | 19.0 | 40 |
| Device Example 32 | Compound 38 | Compound 38 | 0.173 | 0.381 | 474 | 7.8 | 42.4 | 19.1 | 17.0 | 54 |
| Comparative Device Example 1 | CC-1 | Compound BL | 0.177 | 0.387 | 474 | 6.8 | 42.5 | 18.8 | 19.7 | 40 |
| Comparative Device Example 2 | CC-2 | Compound BL | 0.179 | 0.396 | 474 | 7.2 | 35.4 | 15.4 | 15.5 | 176 |

Table 2 is a summary of the device data. The devices with aryl silane hosts show high efficiency and long lifetimes. Compared to the host without aryl silane moiety, CC-2, the aryl silane hosts demonstrates much improved efficiency (Device Examples 1-16 vs. Comparative Device Example 2). Without being bound by theory, these results are attributable in part to the breakage of conjugation by the silane bridge and retention of high triplet energy for individual molecules. Additionally, the steric hindrance introduced by the tetraphenylsilane unit can also prevent unfavorable intermolecular stacking that can decrease the triplet energy in the solid state. A high triplet energy of the host effectively confines the excitons on emitters, leading to high efficiency.

Furthermore, devices with the asymmetric aryl silane hosts have comparable to much improved lifetime than those with the symmetric aryl silane hosts (Device Examples 1-16 vs Comparative Device Example 1). This is attributable to the asymmetric nature of, for example, Compound 23, which not only lowers the operation voltage, but also helps to balance charge fluxes. The balanced electron/hole fluxes spread the charge recombination zone, which preserves a high efficiency at high brightness by suppressing or reducing exciton quenching. An expanded charge recombination zone also extends the device lifetime by allowing a larger population of molecules to have charge transport, exciton formation, and light emission roles. It is also demonstrated that the compounds of Formula I are useful as blocking layer components (Device Examples 17-32), producing OLEDs having high efficiencies and long lifetimes. Since compounds of Formula I can serve both as hosts and hole blocking layers, these materials are expected to reduce device fabrication cost.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and sliane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

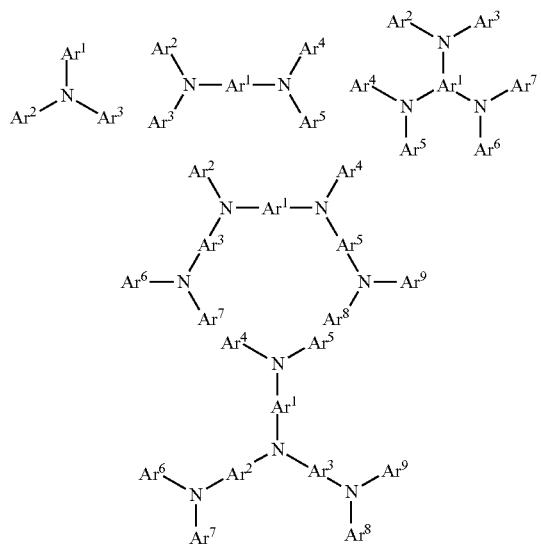

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

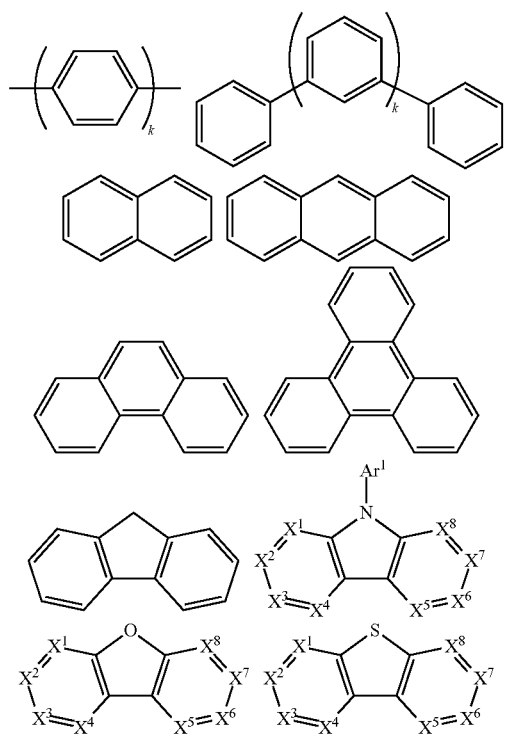

k is an integer from 1 to 20; $X^1$ to $X^8$ is C (including CH) or N; $Ar^1$ has the same group defined above.

Examples of metal complexes used in HIL or HTL include, but not limit to the following general formula:

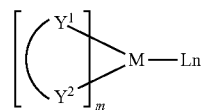

M is a metal, having an atomic weight greater than 40; ($Y^1$-$Y^2$) is a bindentate ligand, Y1 and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, ($Y^1$-$Y^2$) is a 2-phenylpyridine derivative.

In another aspect, ($Y^1$-$Y^2$) is a carbene ligand.

In another aspect, M is selected from Ir, Pt, Os, and Zn.

In a further aspect, the metal complex has a smallest oxidation potential in solution vs. $Fc^+$/Fc couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant.

Examples of metal complexes used as host are preferred to have the following general formula:

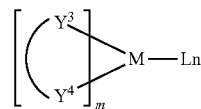

M is a metal; ($Y^3$-$Y^4$) is a bindentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

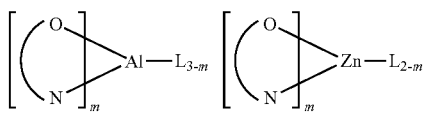

(O—N) is a bidentate ligand, having metal coordinated to atoms O and N.

In another aspect, M is selected from Ir and Pt.

In a further aspect, ($Y^3$-$Y^4$) is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atome, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

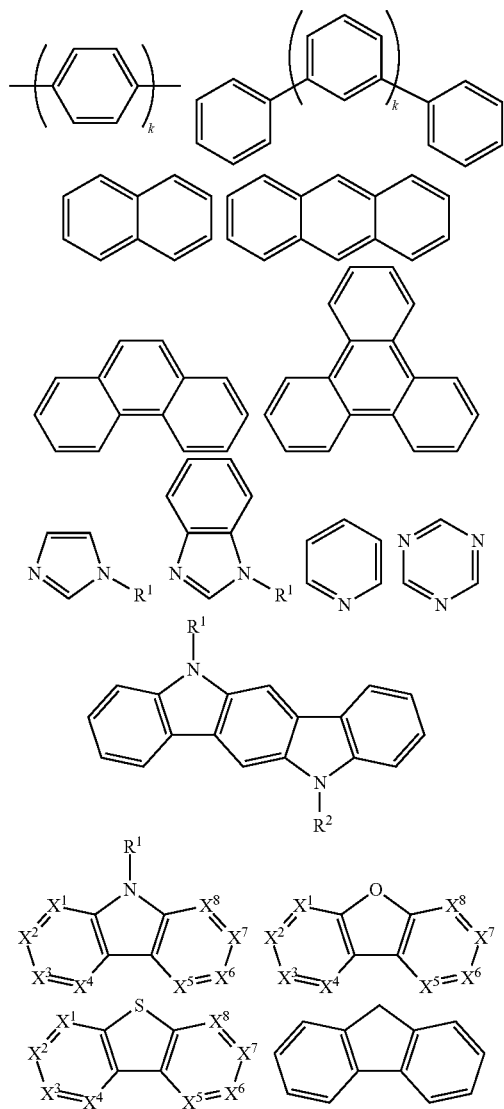
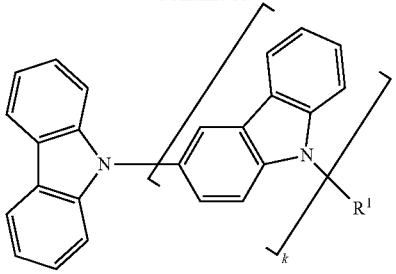
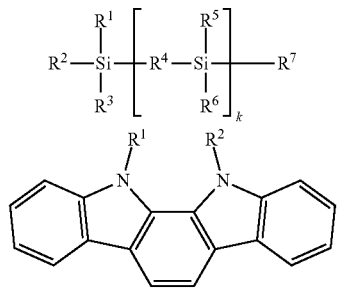

$R^1$ to $R^7$ is independently selected from the group consisting of hydrogen, alkyl, alkoxy, amino, alkenyl, alkynyl, arylalkyl, heteroalkyl, aryl and heteroaryl, when it is aryl or heteroaryl, it has the similar definition as Ar's mentioned above.

k is an integer from 0 to 20.

$X^1$ to $X^8$ is selected from C (including CH) or N.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule used as host described above.

In another aspect, compound used in HBL contains at least one of the following groups in the molecule:

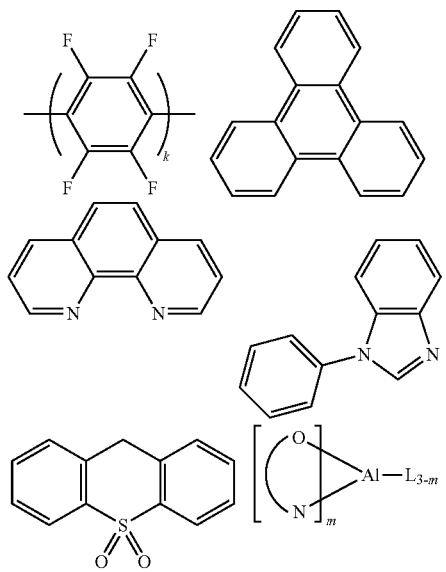

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

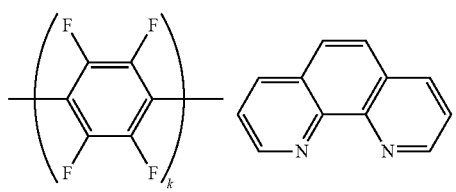

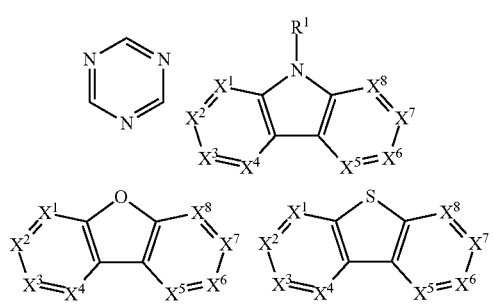

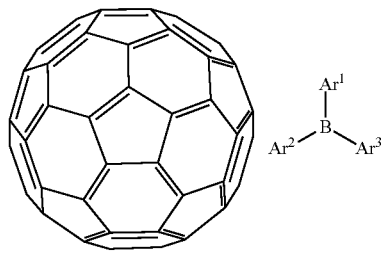

$R^1$ is selected from the group consisting of hydrogen, alkyl, alkoxy, amino, alkenyl, alkynyl, arylalkyl, heteroalkyl, aryl and heteroaryl, when it is aryl or heteroaryl, it has the similar definition as Ar's mentioned above.

$Ar^1$ to $Ar^3$ has the similar definition as Ar's mentioned above.

k is an integer from 0 to 20.

$X^1$ to $X^8$ is selected from C (including CH) or N.

In another aspect, the metal complexes used in ETL contains, but not limit to the following general formula:

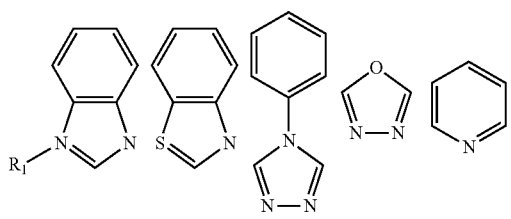

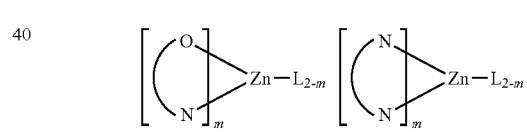

(O—N) or (N—N) is a bidentate ligand, having metal coordinated to atoms O, N or N, N; L is an ancillary ligand; m is an integer value from 1 to the maximum number of ligands that may be attached to the metal.

In any above-mentioned compounds used in each layer of the OLED device, the hydrogen atoms can be partially or fully deuterated.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 3 below. Table 3 lists non-limiting classes of materials, non-limiting examples of compounds for each class, and references that disclose the materials.

TABLE 3

| MATERIAL | EXAMPLES OF MATERIAL | PUBLICATIONS |
| --- | --- | --- |
| Hole injection materials | | |
| Phthalocyanine and porphyrin compounds | | Appl. Phys. Lett. 69, 2160 (1996) |
| Starburst triarylamines | | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polythiophene) | | Synth. Met. 87, 171 (1997) WO2007002683 |
| Phosphonic acid and silane SAMs | | US20030162053 |

TABLE 3-continued
| MATERIAL | EXAMPLES OF MATERIAL | PUBLICATIONS |
| --- | --- | --- |
| Triarylamine or polythiophene polymers with conductivity dopants | 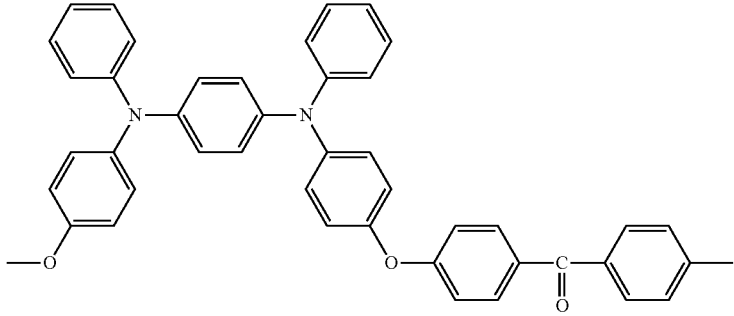 and 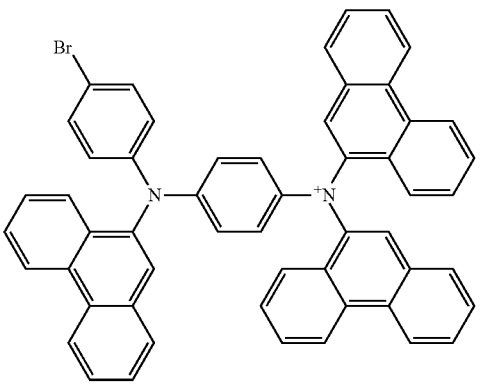 [SMILES: Brc1ccc(N(c2ccc([NH+](c3cc4ccccc4c4ccccc34)c3cc4ccccc4c4ccccc34)cc2)c2cc3ccccc3c3ccccc23)cc1] 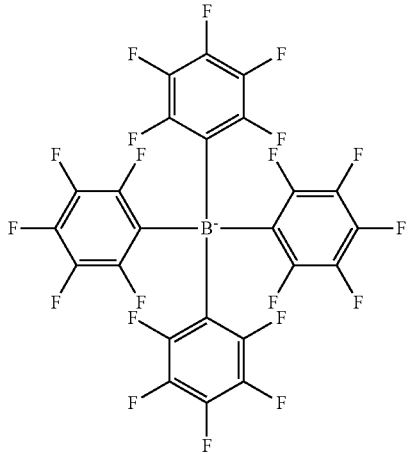 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | EA01725079A1 |
| Arylamines complexed with metal oxides such as molybdenum and tungsten oxides | 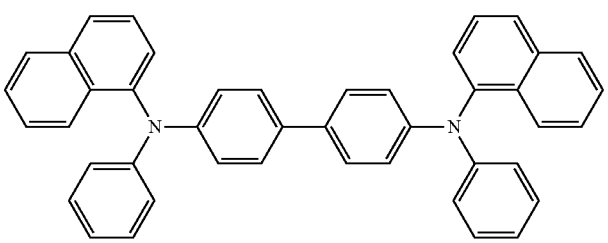 [SMILES: c1ccc(N(c2ccc(-c3ccc(N(c4ccccc4)c4cccc5ccccc45)cc3)cc2)c2cccc3ccccc23)cc1] + MoO$_x$ | SID Symposium Digest, 37, 923 (2006) WO2009018009 |

TABLE 3-continued

| MATERIAL | EXAMPLES OF MATERIAL | PUBLICATIONS |
| --- | --- | --- |
| p-type semiconducting organic complexes | | US20020158242 |
| Metal organometallic complexes | | US20060240279 |
| Cross-linkable compounds | | US20080220265 |
| Hole transporting materials | | |
| Triarylamines (e.g., TPD, α-NPD) | | Appl. Phys. Lett. 51, 913 (1987) |
| | | US5061569 |

TABLE 3-continued
| MATERIAL | EXAMPLES OF MATERIAL | PUBLICATIONS |
| --- | --- | --- |
| | 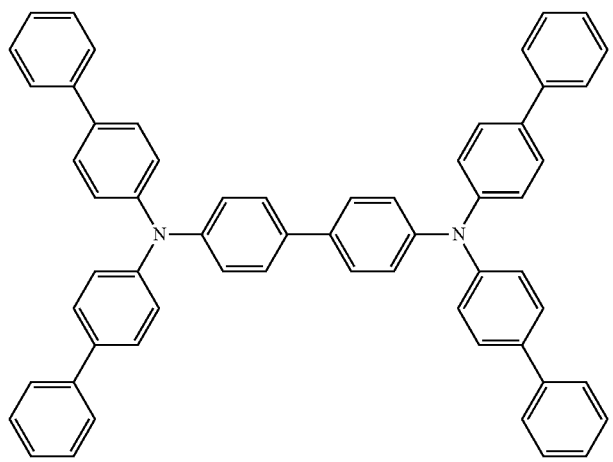 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 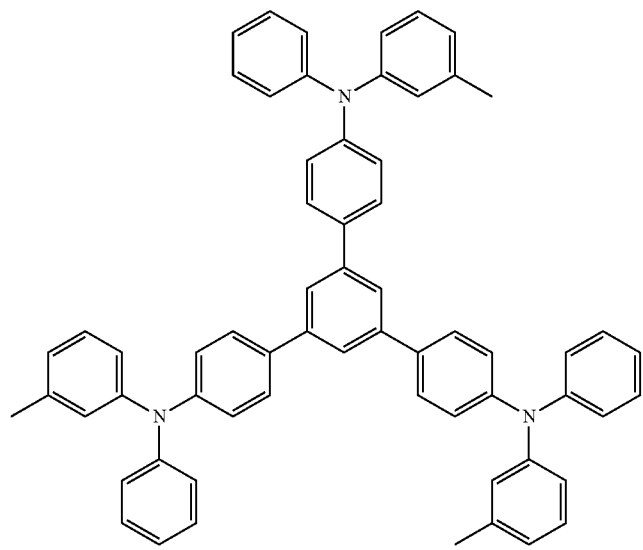 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |
| | 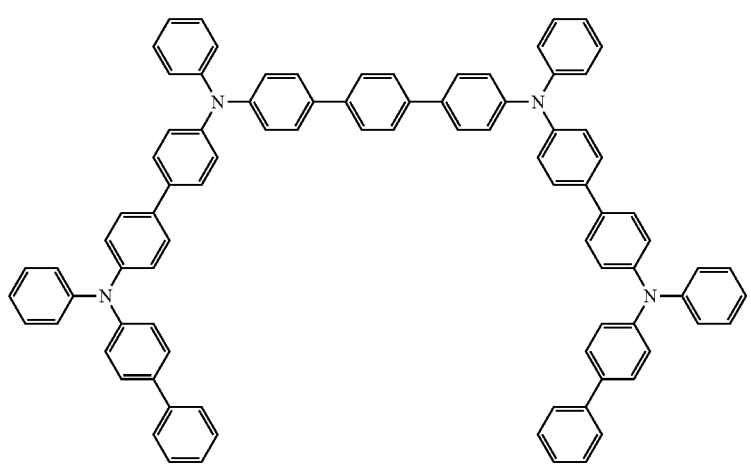 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |

TABLE 3-continued

| MATERIAL | EXAMPLES OF MATERIAL | PUBLICATIONS |
|---|---|---|
| | | Appl. Phys. Lett. 90, 183503 (2007) |
| Triarylamine on spirofluorene core | | Synth. Met. 91, 209 (1997) |
| Arylamine carbazole compounds | | Adv. Mater. 6, 677 (1994), US20080124572 |
| Triarylamine with (di)benzothiophene/(di)benzofuran | | US20070278938, US20080106190 |

TABLE 3-continued

| MATERIAL | EXAMPLES OF MATERIAL | PUBLICATIONS |
|---|---|---|
| Indolocarbazoles | | Synth. Met. 111, 421 (2000) |
| Isoindole compounds | | Chem. Mater. 15, 3148 (2003) |
| Metal carbene complexes | | US20080018221 |

Phosphorescent OLED host materials

Red hosts

| | | |
|---|---|---|
| Arylcarbazoles | | Appl. Phys. Lett. 78, 1622 (2001) |

TABLE 3-continued

| MATERIAL | EXAMPLES OF MATERIAL | PUBLICATIONS |
|---|---|---|
| Metal 8-hydroxy-quinolates (e.g., Alq$_3$, BAlq) | | Nature 395, 151 (1998) |
| | | US20060202194 |
| | | US2005014551 |
| | | WO2006072002 |
| Metal phnoxybenzothiazole compounds | | Appl. Phys. Lett. 90, 123509 (2007) |
| Conjugated oligomers and polymers (e.g., polyfluorene) | | Org. Electron. 1, 15 (2000) |
| Aromatic fused rings | | WO2009066779, WO2009066778, WO2009063833, US20090045731, US20090045730, WO2009008311, US20090008605, US20090009065 |

TABLE 3-continued
| MATERIAL | EXAMPLES OF MATERIAL | PUBLICATIONS |
|---|---|---|
| Zinc complexes | 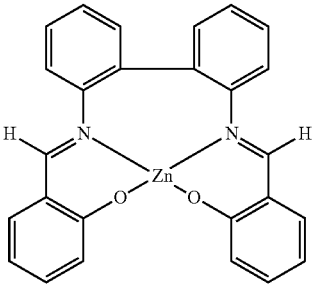 | WO2009062578 |
| Green hosts | | |
| Arylcarbazoles | 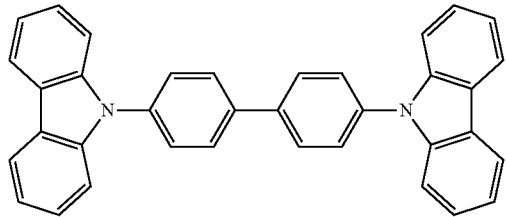 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| | 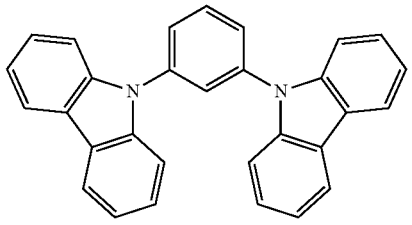 [SMILES: c1cc(-n2c3ccccc3c3ccccc32)cc(-n2c3ccccc3c3ccccc32)c1] | US20030175553 |
| | 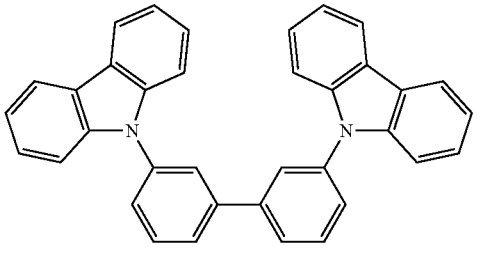 [SMILES: c1cc(-c2cccc(-n3c4ccccc4c4ccccc43)c2)cc(-n2c3ccccc3c3ccccc32)c1] | WO2001039234 |
| Aryltriphenylene compounds | 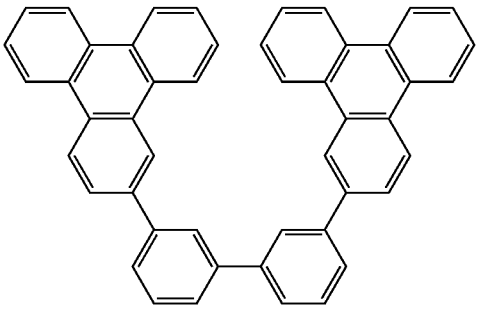 [SMILES: c1cc(-c2cccc(-c3ccc4c5ccccc5c5ccccc5c4c3)c2)cc(-c2ccc3c4ccccc4c4ccccc4c3c2)c1] | US20060280965 |

TABLE 3-continued
| MATERIAL | EXAMPLES OF MATERIAL | PUBLICATIONS |
|---|---|---|
| | 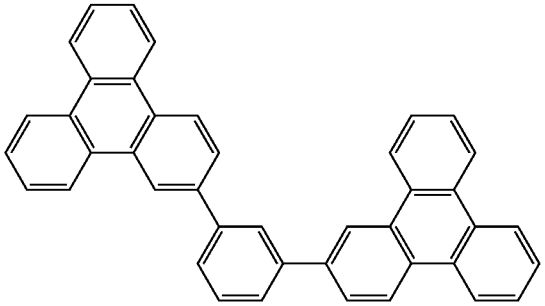 [SMILES: c1cc(-c2ccc3c4ccccc4c4ccccc4c3c2)cc(-c2ccc3c4ccccc4c4ccccc4c3c2)c1] | US20060280965 |
| | 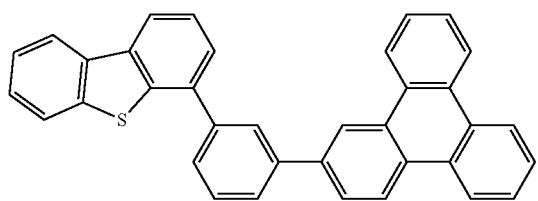 [SMILES: c1cc(-c2ccc3c4ccccc4c4ccccc4c3c2)cc(-c2cccc3c2sc2ccccc23)c1] | WO2009021126 |
| Donor acceptor type molecules | 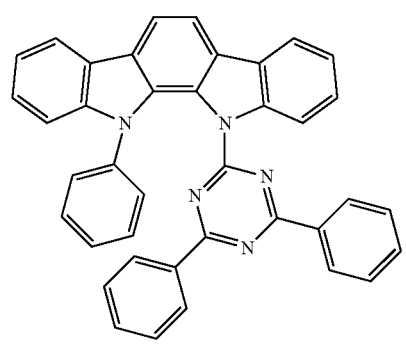 [SMILES: c1ccc(-c2nc(-c3ccccc3)nc(-n3c4ccccc4c4ccc5c6ccccc6n(-c6ccccc6)c5c43)n2)cc1] | WO2008056746 |
| Aza-carbazole/DBT/ DBF | 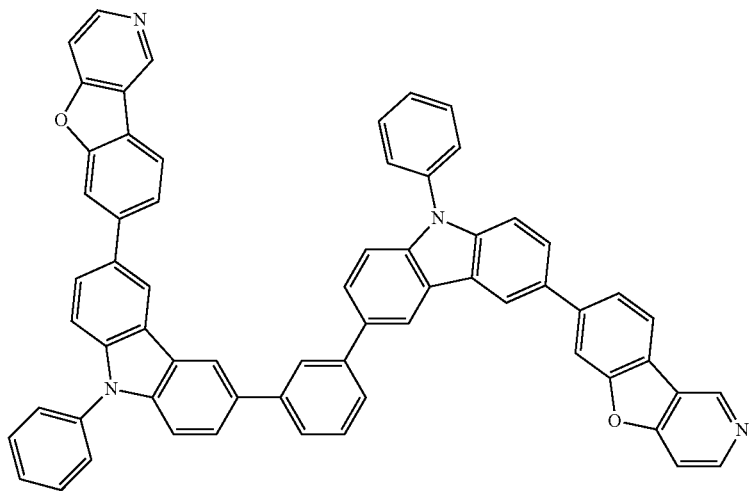 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| Polymers (e.g., PVK) | 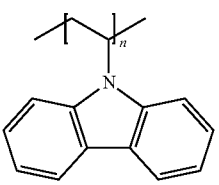 | Appl. Phys. Lett. 77, 2280 (2000) |

TABLE 3-continued
| MATERIAL | EXAMPLES OF MATERIAL | PUBLICATIONS |
|---|---|---|
| Spirofluorene compounds | 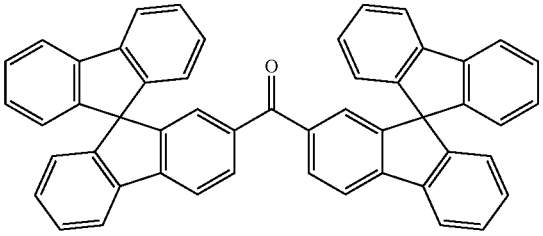 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxybenzooxazole compounds | 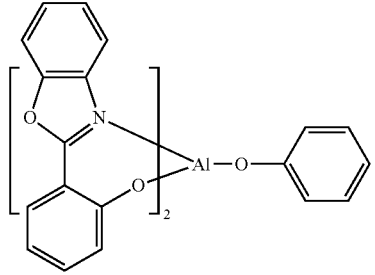 | WO2005089025 |
|  | 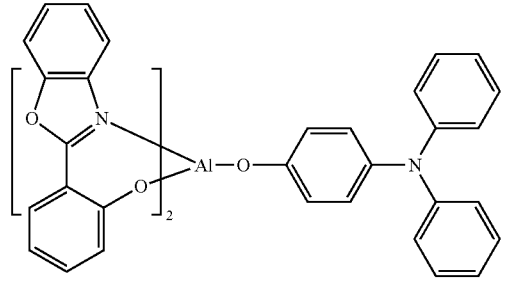 | WO200613273 |
|  | 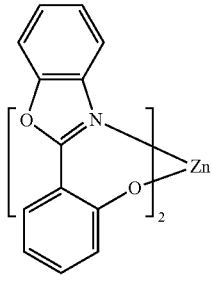 | JP200511610 |
| Spirofluorene-carbazole compounds | 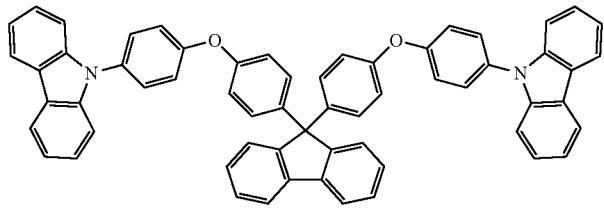 [SMILES: c1ccc2c(c1)-c1ccccc1C2(c1ccc(Oc2ccc(-n3c4ccccc4c4ccccc43)cc2)cc1)c1ccc(Oc2ccc(-n3c4ccccc4c4ccccc43)cc2)cc1] | JP2007254297 |

TABLE 3-continued
| MATERIAL | EXAMPLES OF MATERIAL | PUBLICATIONS |
|---|---|---|
| | 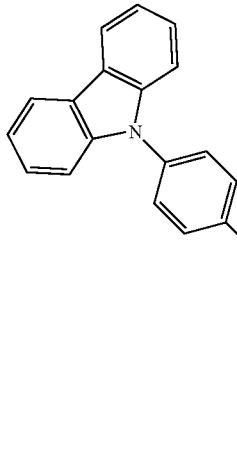 | JP2007254297 |
| Indolocabazoles | 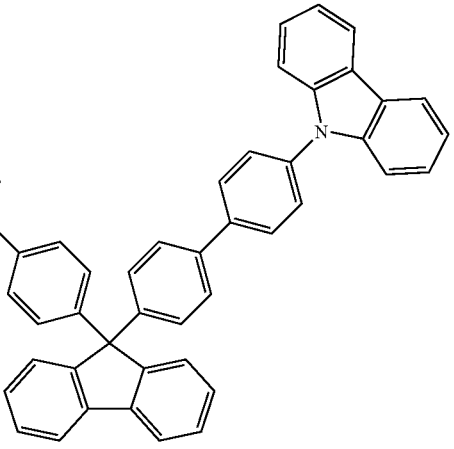 | WO2007063796 |
| | 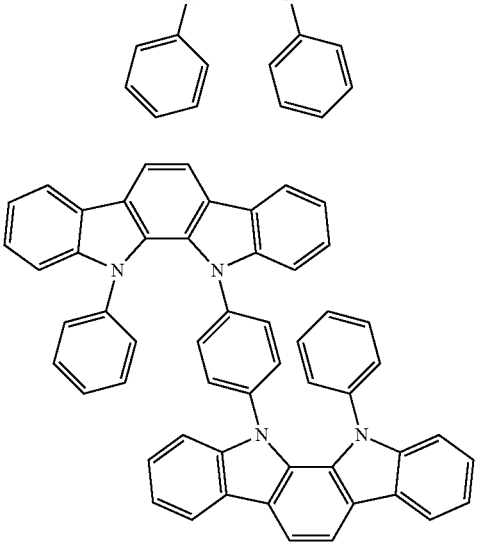 | WO2007063754 |
| 5-member ring electron deficient heterocycles (e.g., triazole, oxadiazole) | 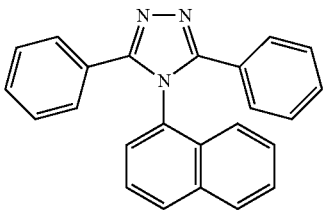 [SMILES: c1ccc(-c2nnc(-c3ccccc3)n2-c2cccc3ccccc23)cc1] | J. Appl. Phys. 90, 5048 (2001) |
| | 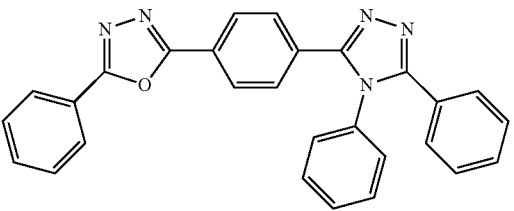 [SMILES: c1ccc(-c2nnc(-c3ccc(-c4nnc(-c5ccccc5)n4-c4ccccc4)cc3)o2)cc1] | WO2004107822 |

TABLE 3-continued
| MATERIAL | EXAMPLES OF MATERIAL | PUBLICATIONS |
|---|---|---|
| Tetraphenylene complexes | 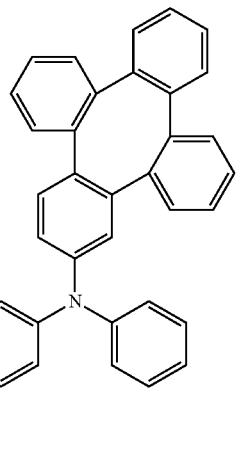 | US20050112407 |
| Metal phenoxypyridine compounds | 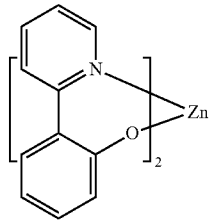 | WO2005030900 |
| Metal coordination complexes (e.g., Zn, Al, with N^N ligands | 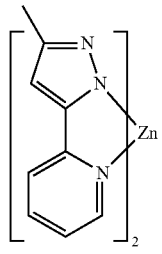 | US20040137268, US20040137267 |
Blue hosts
| | | |
|---|---|---|
| Arylcarbazoles | 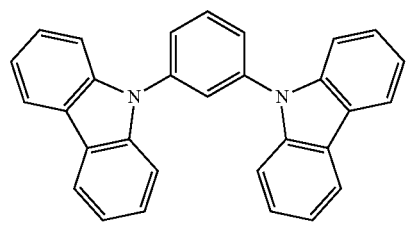 [SMILES: c1cc(-n2c3ccccc3c3ccccc32)cc(-n2c3ccccc3c3ccccc32)c1] | Appl. Phys. Lett, 82, 2422 (2003) |
| | 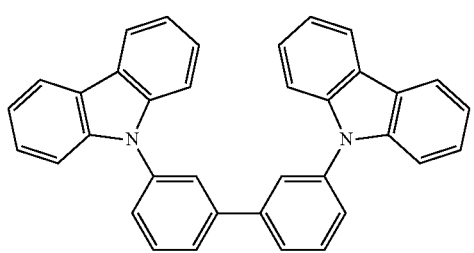 [SMILES: c1cc(-c2cccc(-n3c4ccccc4c4ccccc43)c2)cc(-n2c3ccccc3c3ccccc32)c1] | US20070190359 |

TABLE 3-continued
| MATERIAL | EXAMPLES OF MATERIAL | PUBLICATIONS |
|---|---|---|
| Dibenzothiophene/Di-benzofuran-carbazole compounds | 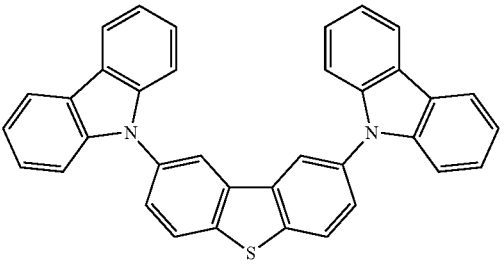 [SMILES: c1ccc2c(c1)c1ccccc1n2-c1ccc2sc3ccc(-n4c5ccccc5c5ccccc54)cc3c2c1] | WO2006114966, US20090167162 |
| | 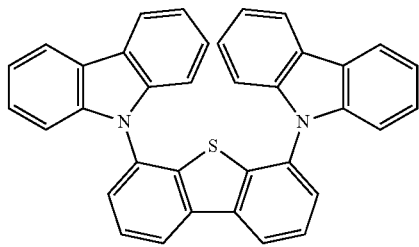 [SMILES: c1cc(-n2c3ccccc3c3ccccc32)c2sc3c(-n4c5ccccc5c5ccccc54)cccc3c2c1] | US20090167162 |
| | 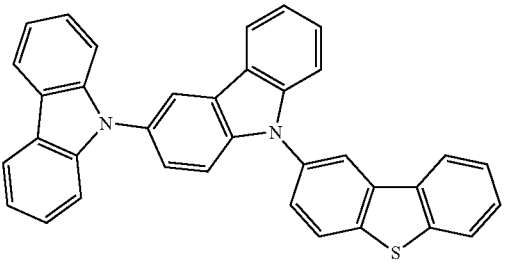 [SMILES: c1ccc2c(c1)sc1ccc(-n3c4ccccc4c4cc(-n5c6ccccc6c6ccccc65)ccc43)cc12] | WO2009086028 |
| | 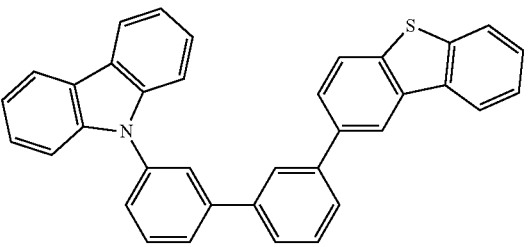 [SMILES: c1cc(-c2cccc(-n3c4ccccc4c4ccccc43)c2)cc(-c2ccc3sc4ccccc4c3c2)c1] | US20090030202, US20090017330 |
| Silicon aryl compounds | 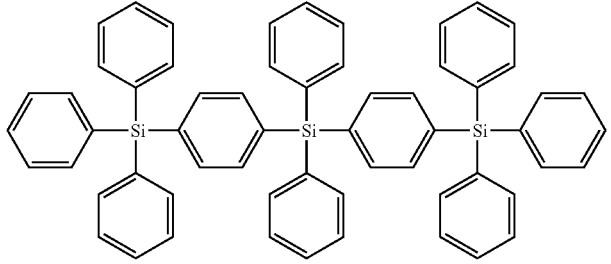 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 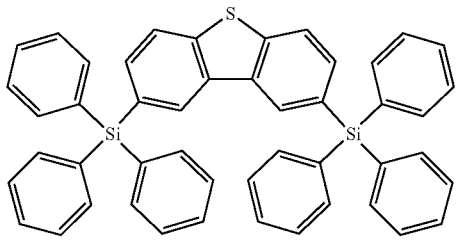 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE 3-continued

| MATERIAL | EXAMPLES OF MATERIAL | PUBLICATIONS |
| --- | --- | --- |
| Silicon/Germanium aryl compounds | | EP2034538A |
| Aryl benzoyl ester | | WO2006100298 |
| High triplet metal organometallic complex | | US7154114 |

Phophorescent dopants
Red dopants

| | | |
| --- | --- | --- |
| Heavy metal porphyrins (e.g., PtOEP) | | Nature 395, 151 (1998) |
| Iridium(III) organometallic complexes | | Appl. Phys. Lett. 78, 1622 (2001) |

TABLE 3-continued

| MATERIAL | EXAMPLES OF MATERIAL | PUBLICATIONS |
| --- | --- | --- |
| | | US2006835469 |
| | | US2006835469 |
| | | US20060202194 |
| | | US20060202194 |
| | | US20070087321 |

TABLE 3-continued

| MATERIAL | EXAMPLES OF MATERIAL | PUBLICATIONS |
|---|---|---|
| | | US20070087321 |
| | | Adv. Mater. 19, 739 (2007) |
| | | WO2009100991 |
| | | WO2008101842 |
| Platinum(II) organometallics complexes | | WO2003040257 |

TABLE 3-continued
| MATERIAL | EXAMPLES OF MATERIAL | PUBLICATIONS |
| --- | --- | --- |
| Osminum(III) complexes | 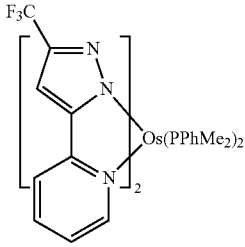 | Chem. Mater. 17, 3532 (2005) |
| Ruthenium(II) complexes | 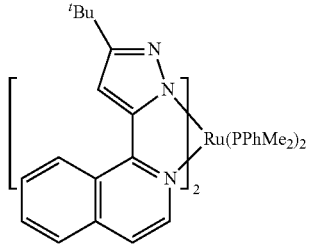 | Adv. Mater. 17, 1059 (2005) |
| Rhenium (I), (II), and (III) complexes | 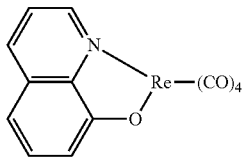 | US20050244673 |
Green dopants
| | | |
| --- | --- | --- |
| Iridium(III) organometallic complexes | 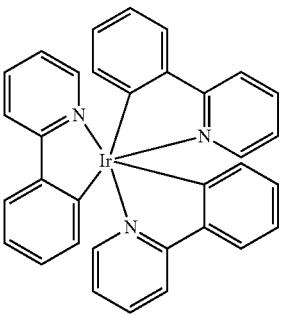
and its derivatives | Inorg. Chem. 40, 1704 (2001) |
| | 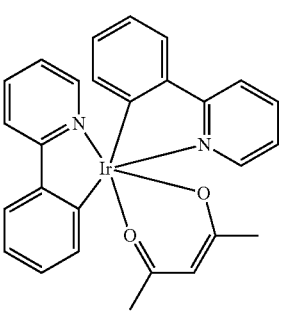 | US20020034656 |

TABLE 3-continued
| MATERIAL | EXAMPLES OF MATERIAL | PUBLICATIONS |
|---|---|---|
| | 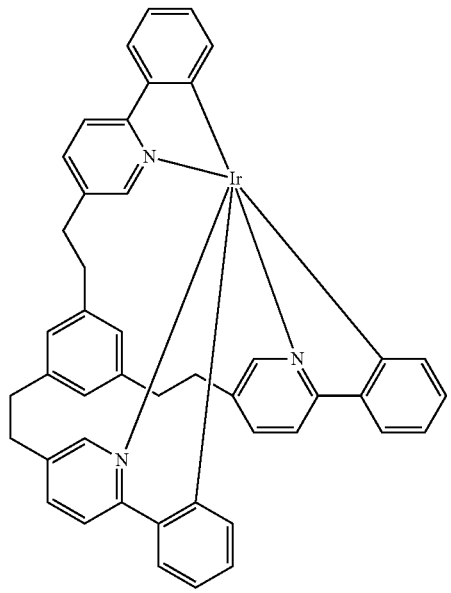 | US7332232 |
| | 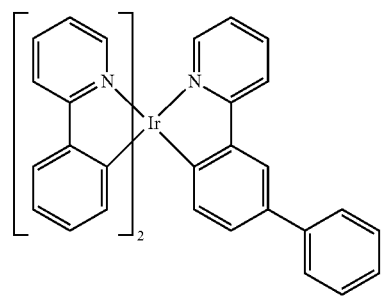 | US20090108737 |
| | 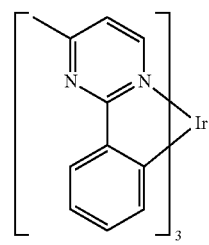 | US20090039776 |
| | 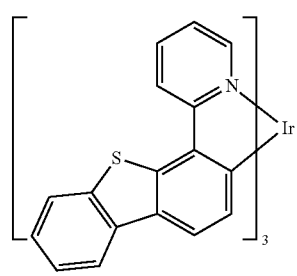 | US6921915 |

TABLE 3-continued
| MATERIAL | EXAMPLES OF MATERIAL | PUBLICATIONS |
|---|---|---|
| | 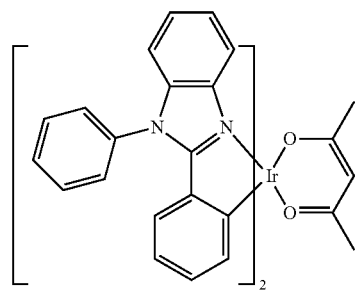 | US6687266 |
| | 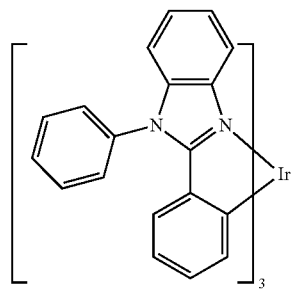 | Chem. Mater. 16, 2480 (2004) |
| | 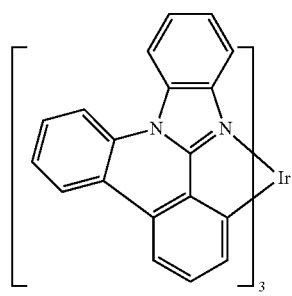 | US20070190359 |
| | 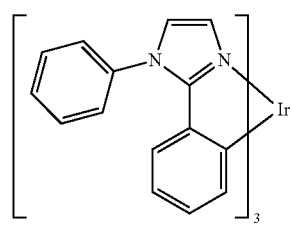 | US 20060008670<br>JP2007123392 |
| | 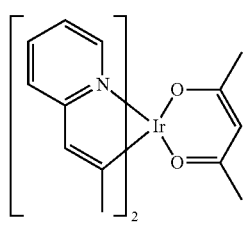 | Adv. Mater. 16, 2003 (2004) |

TABLE 3-continued

| MATERIAL | EXAMPLES OF MATERIAL | PUBLICATIONS |
|---|---|---|
| | | Agnew. Chem. Int. Ed. 2006, 45, 7800 |
| | | WO2009050290 |
| | | US20090165846 |
| | | US20080015355 |
| Monomer for polymeric metal organometallic compounds | | US7250226, US7396598 |

TABLE 3-continued

| MATERIAL | EXAMPLES OF MATERIAL | PUBLICATIONS |
| --- | --- | --- |
| Pt(II) organometallic complexes, including polydentated ligands | | Appl. Phys. Lett. 86, 153505 (2005) |
| | | Appl. Phys. Lett. 86, 153505 (2005) |
| | | Chem. Lett. 34, 592 (2005) |
| | | WO2002015645 |
| | | US20060263635 |

TABLE 3-continued

| MATERIAL | EXAMPLES OF MATERIAL | PUBLICATIONS |
| --- | --- | --- |
| Cu complexes | | WO2009000673 |
| Gold complexes | | Chem. Commun. 2906 (2005) |
| Rhenium(III) complexes | | Inorg. Chem. 42, 1248 (2003) |
| Deuterated organometallic complexes | | US20030138657 |

TABLE 3-continued
| MATERIAL | EXAMPLES OF MATERIAL | PUBLICATIONS |
|---|---|---|
| Organometallic complexes with two or more metal centers | 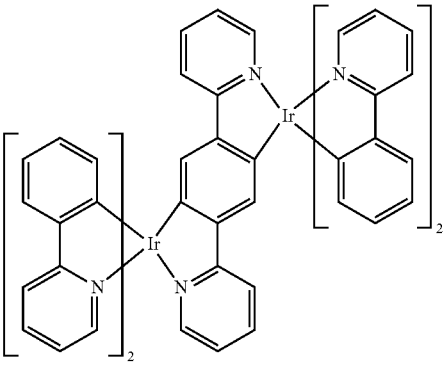 | US20030152802 |
| | 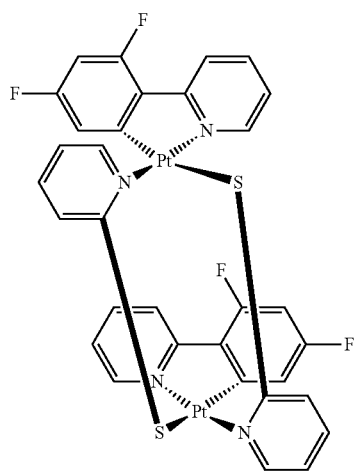 | US7090928 |
| Blue dopants | | |
| Iridium(III) organometallic complexes | 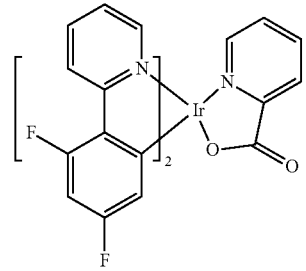 | WO2002002714 |
| | 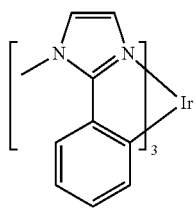 | WO2006009024 |

TABLE 3-continued

| MATERIAL | EXAMPLES OF MATERIAL | PUBLICATIONS |
|---|---|---|
| | | US20060251923 |
| | | US7393599, WO2006056418, US20050260441, WO2005019373 |
| | | US7534505 |
| | | US7445855 |
| | | US20070190359, US20080297033 |
| | | US7338722 |

TABLE 3-continued

| MATERIAL | EXAMPLES OF MATERIAL | PUBLICATIONS |
|---|---|---|
| | | US20020134984 |
| | | Agnew. Chem. Int. Ed. 47, 1 (2008) |
| | | Chem. Mater. 18, 5119 (2006) |
| | | Inorg. Chem. 46, 4308 (2007) |
| | | WO2005123873 |
| | | WO2005123873 |

TABLE 3-continued

| MATERIAL | EXAMPLES OF MATERIAL | PUBLICATIONS |
| --- | --- | --- |
| | | WO2007004380 |
| | | WO2006082742 |
| Osmium(II) complexes | | US7279704 |
| | | Organometallics 23, 3745 (2004) |
| Gold complexes | | Appl. Phys. Lett. 74, 1361 (1999) |
| Platinum(II) complexes | | WO2006098120, WO2006103874 |

TABLE 3-continued
| MATERIAL | EXAMPLES OF MATERIAL | PUBLICATIONS |
|---|---|---|
| Exciton/hole blocking layer materials | | |
| Bathocuprine compounds (e.g., BCP, BPhen) | 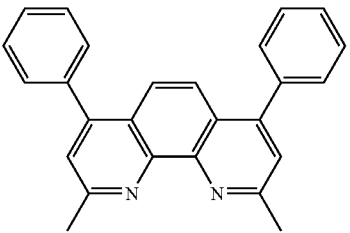 [SMILES: Cc1cc(-c2ccccc2)c2ccc3c(-c4ccccc4)cc(C)nc3c2n1] | Appl. Phys. Lett. 75, 4 (1999) |
| | 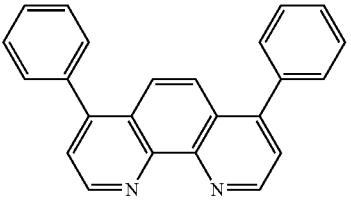 [SMILES: c1ccc(-c2ccnc3c2ccc2c(-c4ccccc4)ccnc23)cc1] | Appl. Phys. Lett. 79, 449 (2001) |
| Metal 8-hydroxy-quinolates (e.g., BAlq) | 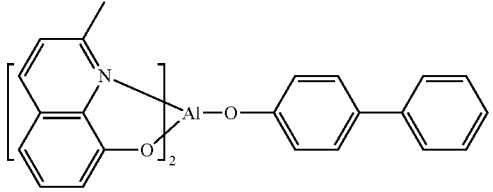 | Appl. Phys. Lett. 81, 162 (2002) |
| 5-member ring electron deficient heterocycles such as triazole, oxadiazole, imidazole, benzoimidazole | 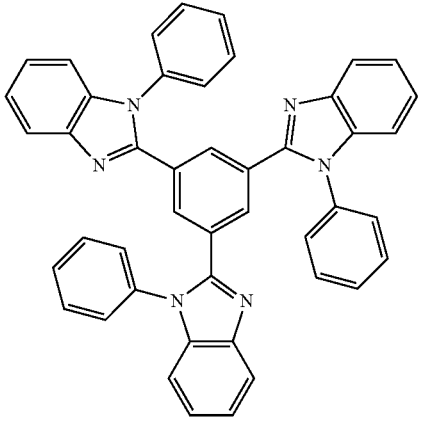 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |

TABLE 3-continued
| MATERIAL | EXAMPLES OF MATERIAL | PUBLICATIONS |
|---|---|---|
| Triphenylene compounds | 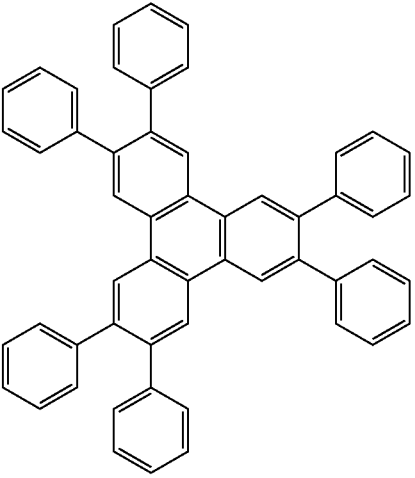 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 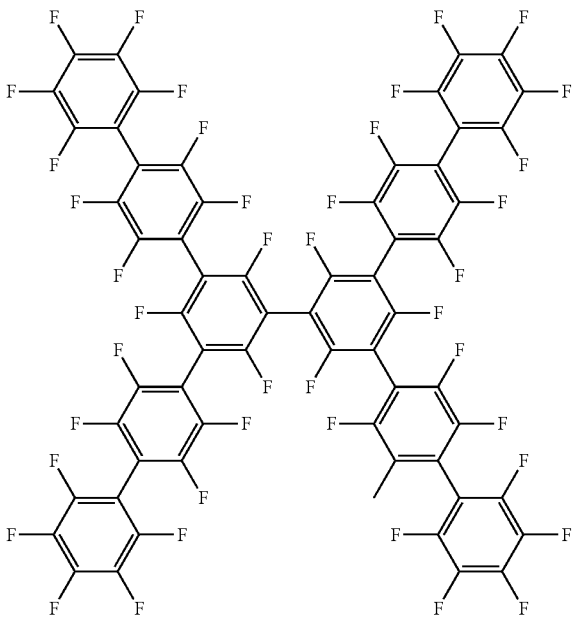 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
| Phenothiazine-S-oxide | 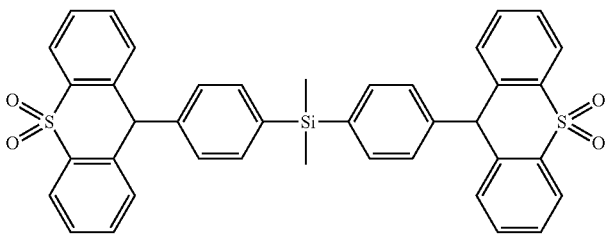 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |

TABLE 3-continued

| MATERIAL | EXAMPLES OF MATERIAL | PUBLICATIONS |
| --- | --- | --- |
| Electron transporting materials | | |
| Anthracene-benzoimidazole compounds | | WO2003060956 |
| | | US20090179554 |
| Aza triphenylene derivatives | | US20090115316 |
| Anthracene-benzothiazole compounds | | Appl. Phys. Lett. 89, 063504 (2006) |
| Metal 8-hydroxy-quinolates (e.g., $Alq_3$, $Zrq_4$) | | Appl. Phys. Lett. 51, 913 (1987) US7230107 |

TABLE 3-continued

| MATERIAL | EXAMPLES OF MATERIAL | PUBLICATIONS |
| --- | --- | --- |
| Metal hydroxybenoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |
| | | Jpn. J. Apply. Phys. 32, L917 (1993) |

TABLE 3-continued

| MATERIAL | EXAMPLES OF MATERIAL | PUBLICATIONS |
| --- | --- | --- |
| Silole compounds | | Org. Electron. 4, 113 (2003) |
| Arylborane compounds | | J. Am. Chem. Soc. 120, 9714 (1998) |
| Fluorinated aromatic compounds | | J. Am. Chem. Soc. 122, 1832 (2000) |
| Fullerene (e.g., C60) | | US20090101870 |
| Triazine complexes | | US20040036077 |

| MATERIAL | EXAMPLES OF MATERIAL | PUBLICATIONS |
| --- | --- | --- |
| Zn (N^N) complexes | 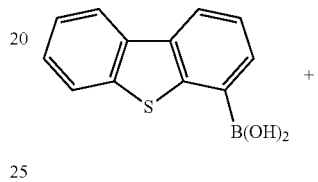 | US6528187 |

EXPERIMENTAL

Chemical abbreviations used throughout this document are as follows: dba is dibenzylideneacetone, EtOAc is ethyl acetate, PPh$_3$ is triphenylphosphine, dppf is 1,1'-bis(diphenylphosphino)ferrocene, DCM is dichloromethane, SPhos is dicyclohexyl(2',6'-dimethoxy-[1,1'-biphenyl]-3-yl)phosphine, THF is tetrahydrofuran.

Example 1

Synthesis of Compound 23

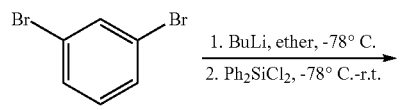

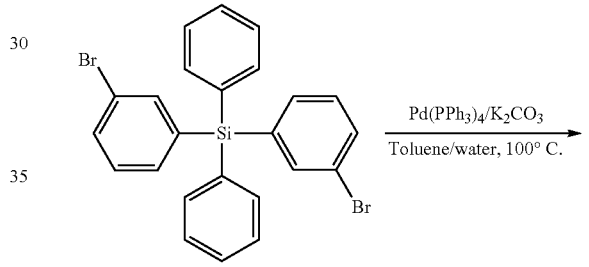

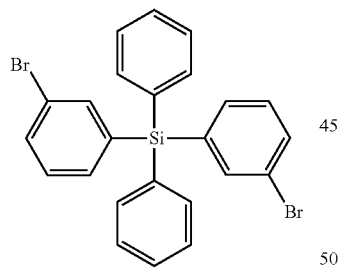

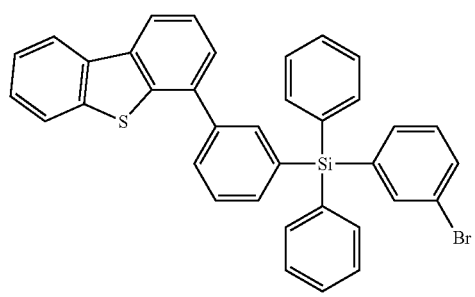

Butyllithium (53.2 mL, 133 mmol, 2.5M in hexane) was added dropwise into a solution of 1,3-dibromobenzene (15.38 mL, 127 mmol) in ether (300 mL) at −78° C. The reaction mixture was stirred at this temperature before dichlorodiphenylsilane (11.90 mL, 57.8 mmol) in ether (20 mL) was added dropwise to yield a clear yellow solution. The solution was allowed to warm up to room temperature overnight and quenched with water. The organic phase was washed with brine and water, dried over Na$_2$SO$_4$. Upon evaporation of the solvent, the residue was purified by column chromatography on silica gel with hexane/DCM (9.8/0.2, v/v) as eluent, and recrystallized from methanol to yield bis(3-bromophenyl)diphenylsilane (25 g, 87%) as white crystals.

A mixture solution of dibenzo[b,d]thiophen-4-boronic acid (1.84 g, 8.04 mmol), bis(3-bromophenyl)diphenylsilane (9.97 g, 20.17 mmol), Pd(PPh$_3$)$_4$ (0.19 g, 0.16 mmol) and potassium carbonate (6.69 g, 48.4 mmol,) in toluene (60 mL) and water (20 mL) was heated at 100° C. under nitrogen overnight. After cooling to room temperature, the reaction mixture was quenched with water, extracted with DCM, washed with brine and water, and dried over Na$_2$SO$_4$. Upon evaporation of the solvent, the residue was purified by column chromatography on silica gel with hexane:DCM (9.5:0.5 to 9:1, v/v) as eluent. The crude product was dissolved in DCM, precipitated with methanol, and filtered to yield (3-bromophenyl)(3-(dibenzo[b,d]thiophen-4-yl)phenyl)diphenylsilane (3.0 g, 62%) as a white solid.

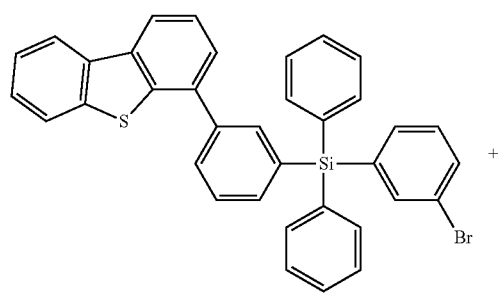

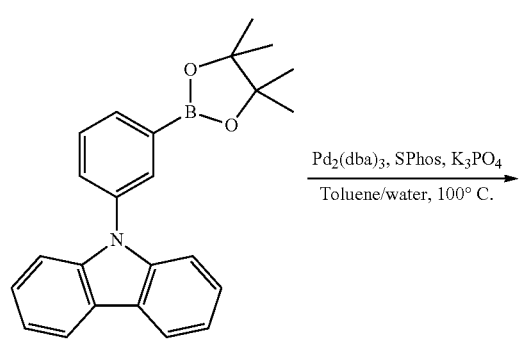

Compound 23

DCM, precipitated with methanol, and filtered to yield Compound 23 (2.2 g, 66%) as a colorless glass.

Example 2

Synthesis of Compound 24

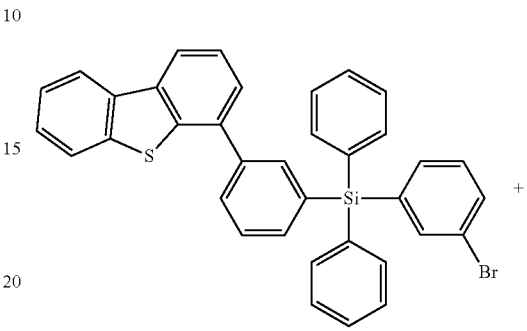

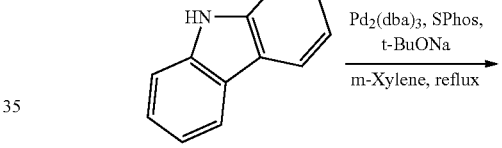

Compound 24

A mixture solution of (3-bromophenyl)(3-(dibenzo[b,d]thiophen-4-yl)phenyl)diphenylsilane (3 g, 5.02 mmol), 9-(3-(4,4,5,5-tetramethyl-1,3,2-dioxaborolan-2-yl)phenyl)-9H-carbazole (2.039 g, 5.52 mmol), tris(dibenzylideneacetone)dipalladium(0) (Pd$_2$(dba)$_3$) (0.092 g, 0.100 mmol), dicyclohexyl(2',6'-dimethoxy-[1,1'-biphenyl]-3-yl)phosphine (SPhos) (0.082 g, 0.201 mmol), and potassium phosphate tribasic (K$_3$PO$_4$) (1.066 g, 5.02 mmol) in toluene (40 mL) and water (4 mL) was heated at 100° C. under nitrogen overnight. The reaction mixture was quenched with water, extracted with DCM, washed with brine and water, and dried over Na$_2$SO$_4$. Upon evaporation of the solvent, the residue was purified by column chromatography with hexane:DCM (9.25:0.75, v/v) as eluent. The crude product was dissolved in A suspension of (3-bromophenyl)(3-(dibenzo[b,d]thiophen-4-yl)phenyl)diphenylsilane (3.5 g, 5.86 mmol), 9H-carbazole (0.979 g, 5.86 mmol), Pd$_2$(dba)$_3$ (0.107 g, 0.117 mmol), SPhos (0.096 g, 0.234 mmol), and sodium tert-butoxide (0.563 g, 5.86 mmol) in m-xylene (50 mL) was refluxed under nitrogen overnight. After cooling to room temperature, the reaction mixture was filtered through a short plug of Celite, and washed with toluene. The combined organic solution was washed with water and dried over Na$_2$SO$_4$. Upon evaporation of the solvent, the crude product was purified by column chromatography on silica gel with hexane:DCM (9.25:0.75, v/v) as eluent. The crude product

Example 3

Synthesis of Compound 25

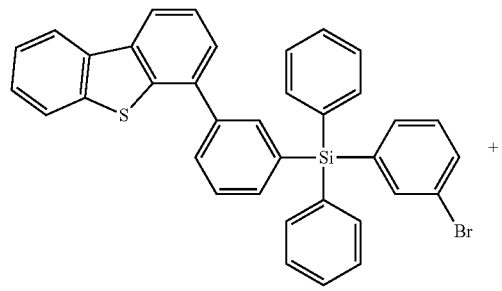

+

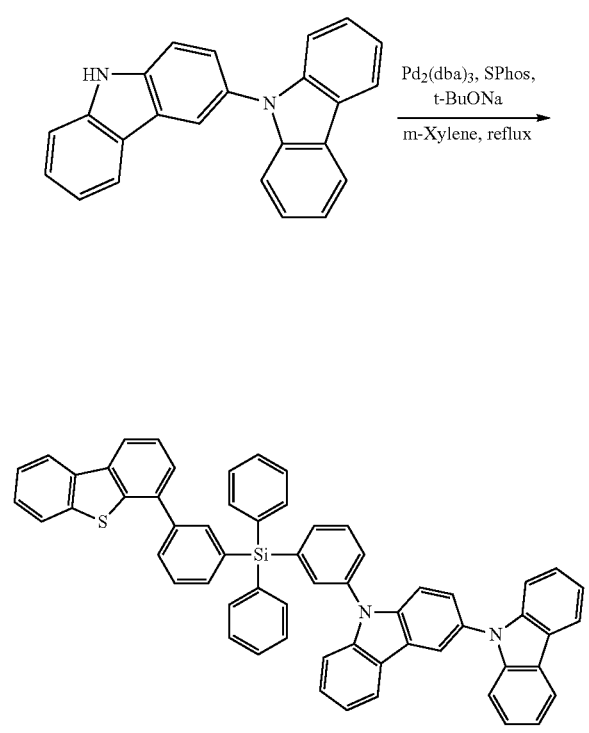

Compound 25

A suspension of (3-bromophenyl)(3-(dibenzo[b,d]thiophen-4-yl)phenyl)diphenylsilane (3.5 g, 5.86 mmol), 9H-3,9'-bicarbazole (1.947 g, 5.86 mmol), $Pd_2(dba)_3$ (0.107 g, 0.117 mmol), SPhos (0.096 g, 0.234 mmol), and sodium tert-butoxide (0.563 g, 5.86 mmol) was added to m-xylene (100 mL) and refluxed under nitrogen overnight. After cooling to room temperature, the reaction mixture was filtered through a short plug of Celite and washed with toluene. The combined organic solution was washed with water, dried over $Na_2SO_4$. Upon evaporation of the solvent, the residue was purified by column chromatography on silica gel with hexane:DCM (8.5:1.5, v/v) as eluent. The crude product was dissolved in DCM, precipitated with methanol, and filtered to yield Compound 24 (2.5 g, 62%) as a colorless glass.

Example 4

Synthesis of Compound 26

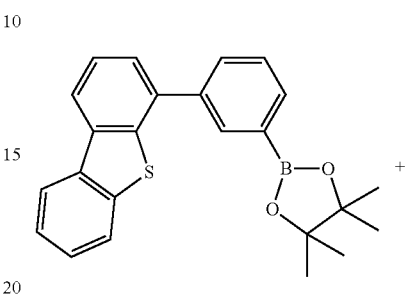

+

A mixture solution of 2-(3-(dibenzo[b,d]thiophen-4-yl)phenyl)-4,4,5,5-tetramethyl-1,3,2-dioxaborolane (6.0 g, 15.53 mmol), bis(3-bromophenyl)diphenylsilane (19.19 g, 38.8 mmol), $Pd_2(dba)_3$ (0.28 g, 0.31 mmol), SPhos (0.26 g, 0.62 mmol) and $K_3PO_4$ (3.30 g, 15.53 mmol) in xylene (150 mL) and water (15 mL) was refluxed under nitrogen at 120° C. overnight. After cooling to room temperature, the reaction mixture was quenched with water, extracted with DCM, washed with brine and water, and dried over $Na_2SO_4$. Upon evaporation of the solvent, the residue was purified by column chromatography on silica gel with hexane:DCM (9.5:0.5 to 9:1, v/v) as eluent. The crude product was dissolved in DCM, precipitated with methanol, and filtered to yield (3-bromophenyl)(3'-(dibenzo[b,d]thiophen-4-yl)-[1,1'-biphenyl]-3-yl)diphenylsilane (3.2 g, 30.6%) as a white powder.

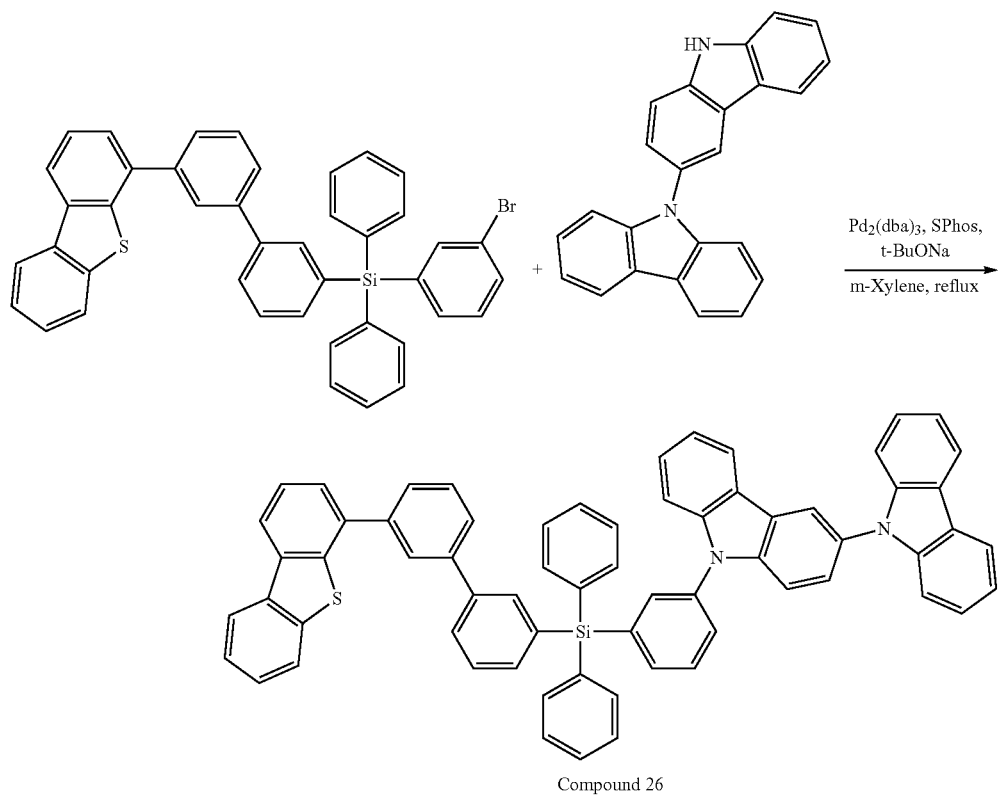

Compound 26

A suspension of (3-bromophenyl)(3'-(dibenzo[b,d]thiophen-4-yl)-[1,1'-biphenyl]-3-yl)diphenylsilane (4.5 g, 6.68 mmol), 9H-3,9'-bicarbazole (2.66 g, 8.02 mmol), Pd$_2$(dba)$_3$ (0.122 g, 0.134 mmol), SPhos (0.110 g, 0.267 mmol), and sodium tert-butoxide (1.284 g, 13.36 mmol) in m-xylene (100 mL) was refluxed at 140° C. under nitrogen overnight. After cooling to room temperature, the reaction mixture was filtered through a short plug of Celite and washed with toluene. The combined organic solution was washed with water, dried over Na$_2$SO$_4$. Upon evaporation of the solvent, the residue was purified by column chromatography on silica gel with hexane:DCM (8:2, v/v) as eluent. The crude product was dissolved in DCM, precipitated with ethanol, and filtered to yield Compound 26 (3.8 g, 62%) as a white powder.

Example 5

Synthesis of Compound 27

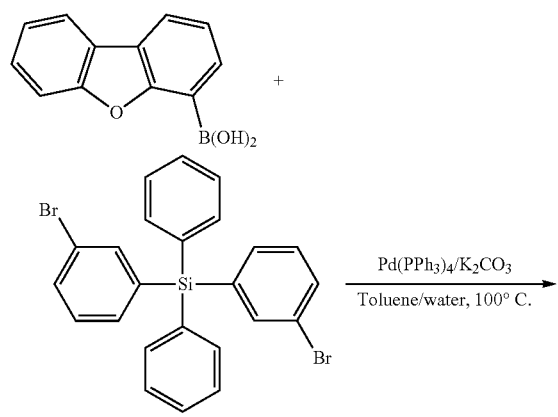

-continued

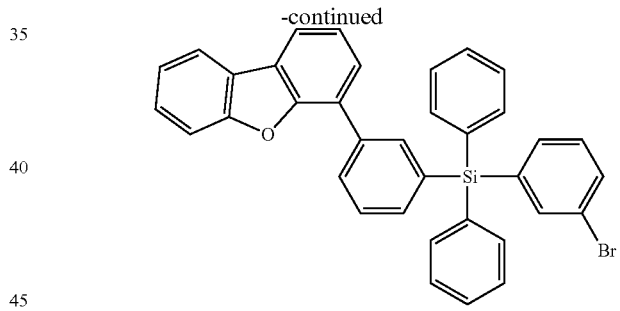

A mixture solution of dibenzo[b,d]furan-4-yl boronic acid (2.5 g, 11.79 mmol), bis(3-bromo-phenyl)diphenylsilane (14.57 g, 29.5 mmol), Pd(PPh$_3$)$_4$ (0.136 g, 0.118 mmol) and K$_2$CO$_3$ (3.26 g, 23.58 mmol) in 150 mL of toluene and 50 mL water was refluxed under nitrogen overnight. After cooling to room temperature, the organic phase was separated and evaporated to dryness. The residue was purified by column chromatography on silica gel with hexane:DCM (9.5:0.5, v/v) as eluent to yield (3-bromophenyl)(3-(dibenzo[b,d]furan-4-yl)phenyl)diphenylsilane (4.4 g, 64%) as a white solid.

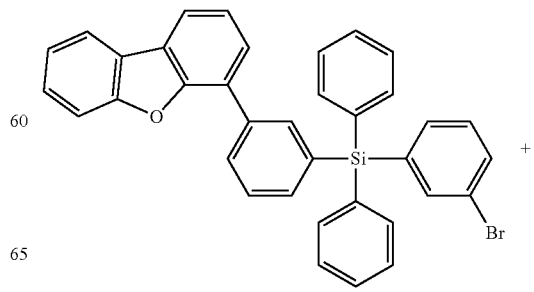

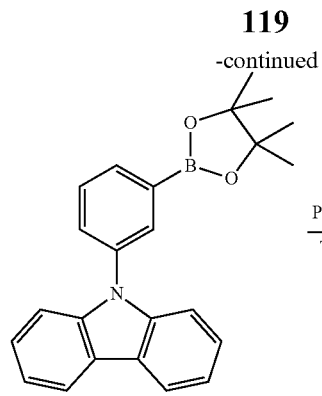

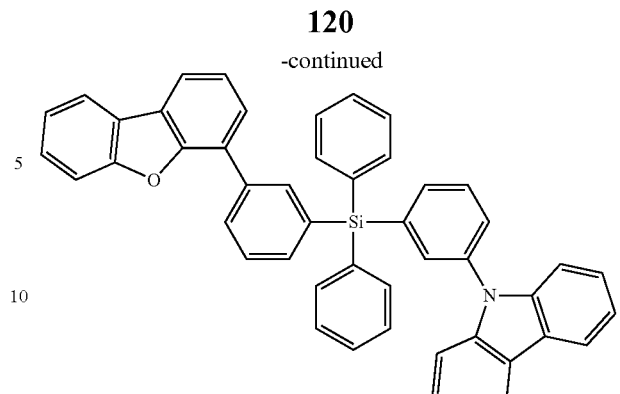

Compound 28

A mixture solution of (3-bromophenyl)(3-(dibenzo[b,d]furan-4-yl)phenyl)diphenylsilane (4.42 g, 7.60 mmol), 9-(3-(4,4,5,5-tetramethyl-1,3-dioxolan-2-yl)phenyl)-9H-carbazole (2.82 g, 7.60 mmol), K$_3$PO$_4$ (3.50 g, 15.20 mmol), Pd$_2$(dba)$_3$ (0.070 g, 0.076 mmol), SPhos (0.062 g, 0.152 mmol) in toluene (200 ml) and water (5 mL) was refluxed under nitrogen overnight. After cooling to room temperature, the organic phase was isolated and evaporated to dryness. The residue was purified by column chromatography on silica gel with hexanes/DCM (75:25, v/v) and sublimation under vacuum (<10$^{-5}$ torr) to yield Compound 27 (1.9 g) as a colorless glass.

Example 6

Synthesis of Compound 28

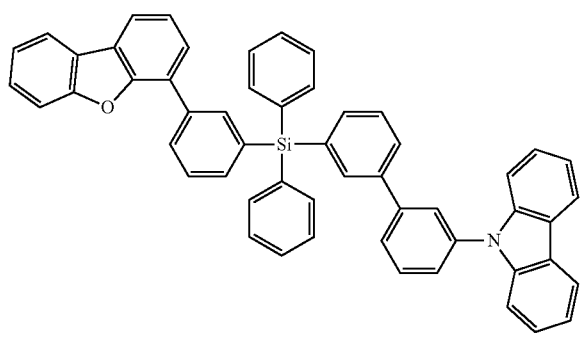

Compound 27

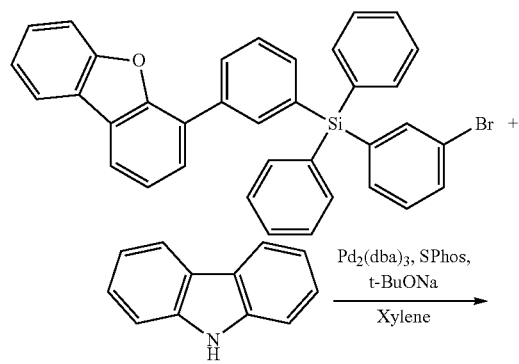

A suspension of 9H-carbazole (1.107 g, 6.62 mmol), (3-bromophenyl)(3-(dibenzo[b,d]furan-4-yl)phenyl)diphenylsilane (3.50 g, 6.02 mmol), Pd$_2$(dba)$_3$ (0.055 g, 0.060 mmol), SPhos (0.049 g, 0.120 mmol) and sodium tert-butoxide (1.157 g, 12.04 mmol) in anhydrous xylene (200 mL) was refluxed under nitrogen overnight. After cooling to room temperature, the reaction mixture was diluted with DCM and filtered through a short plug of silica gel. Upon evaporation of the solvent, the residue was purified by column chromatography on silica gel with hexane:DCM (4/1, v/v) as eluent to yield Compound 28 (3.3 g, 82% yield) as a white solid.

Example 7

Synthesis of Compound 29

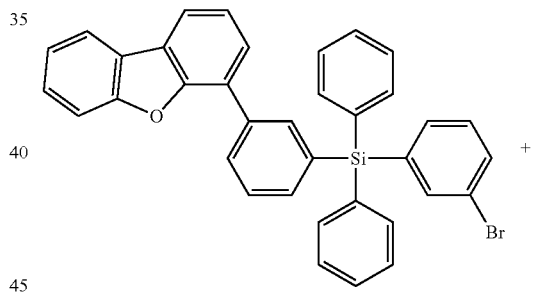

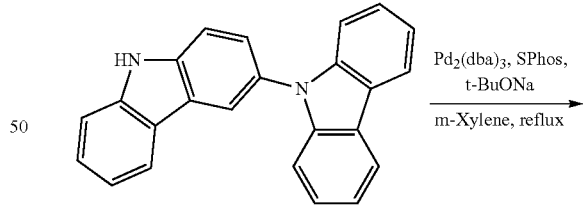

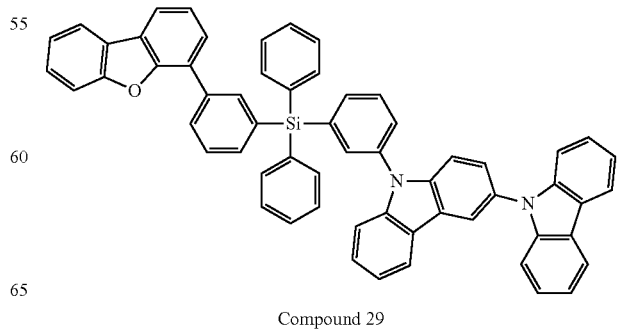

Compound 29

A suspension of (3-bromophenyl)(3-(dibenzo[b,d]furan-4-yl)phenyl)diphenylsilane (2.5 g, 4.30 mmol), 9H-3,9'-bicarbazole (1.715 g, 5.16 mmol), Pd$_2$(dba)$_3$ (0.079 g, 0.086 mmol), SPhos (0.071 g, 0.172 mmol), and sodium tert-butoxide (0.826 g, 8.60 mmol) in xylene (50 mL) was refluxed at 140° C. under nitrogen overnight. After cooling to room temperature, the reaction was quenched with water and extracted with toluene. The organic phase was isolated, washed with water, and dried over MgSO$_4$. Upon evaporation of the solvent, the residue was purified by column chromatography on silica gel with hexane:DCM (8:2, v/v) as eluent, precipitation from DCM to ethanol to yield Compound 29 (2.86 g, 80%) as a white solid.

Example 8

Synthesis of Compound 30

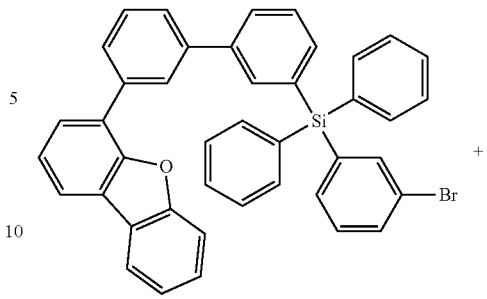

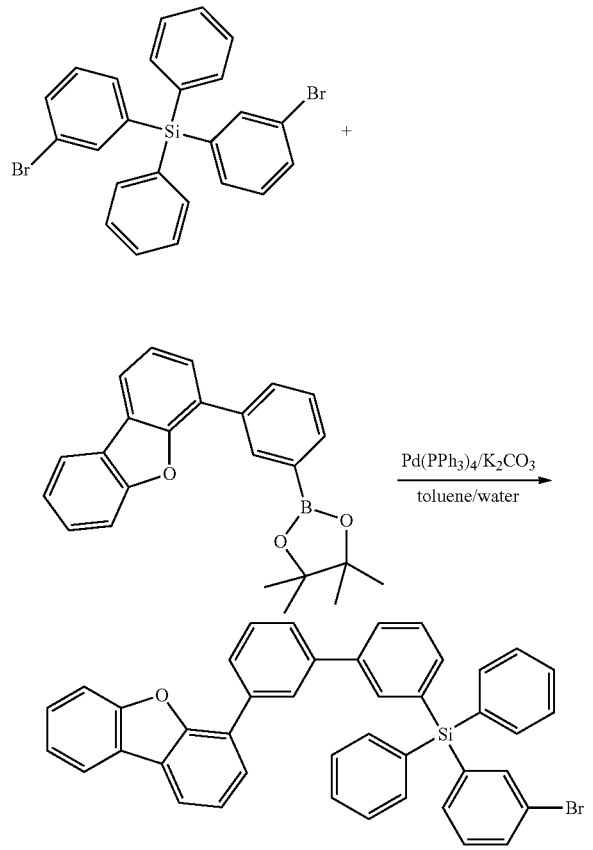

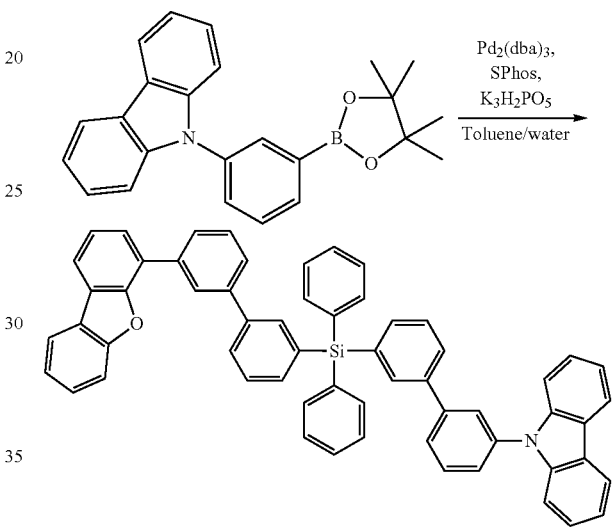

Compound 30

A mixture solution of bis(3-bromophenyl)diphenylsilane (8.01 g, 16.21 mmol), 2-(3-(dibenzo[b,c]furan-4-yl)phenyl)-4,4,5,5-tetramethyl-1,3,2-dioxaborolane (3.00 g, 8.10 mmol), K$_2$CO$_3$ (2.240 g, 16.21 mmol), Pd(PPh$_3$)$_4$ (0.15 g, 0.162 mmol) in toluene (200 mL) and water (50 mL) was refluxed under nitrogen overnight. After cooling to room temperature, the organic phase was isolated and evaporated to dryness. The residue was purified by column chromatography on silica gel with hexane:DCM (9/1 to 3/1, v/v) as eluent to yield (3-bromophenyl)(3'-(dibenzo [b,d]furan-4-yl)-[1,1'-biphenyl]-3-yl)diphenylsilane (3.2 g, 60%) as a white solid.

A mixture solution of (3-bromophenyl)(3'-(dibenzo[b,d]furan-4-yl)-[1,1'-biphenyl]-3-yl)diphenylsilane (2.82 g, 4.29 mmol), 9-(3-(4,4,5,5-tetramethyl-1,3,2-dioxaborolan-2-yl)phenyl)-9H-carbazole (1.583 g, 4.29 mmol), Pd$_2$(dba)$_3$ (0.039 g, 0.043 mmol), SPhos (0.035 g, 0.086 mmol), K$_3$H$_2$PO$_5$ (2.96 g, 12.86 mmol) in toluene (150 mL) and water (5 mL) was heated at 100° C. under nitrogen overnight. After cooling to room temperature, the organic phase was isolated and evaporated to dryness. The residue was purified by column chromatography on silica gel with hexane:DCM (4/1, v/v) as eluent to yield Compound 30 (3.1 g, 88%) as a white solid.

Example 9

Synthesis of Compound 31

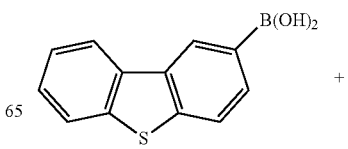

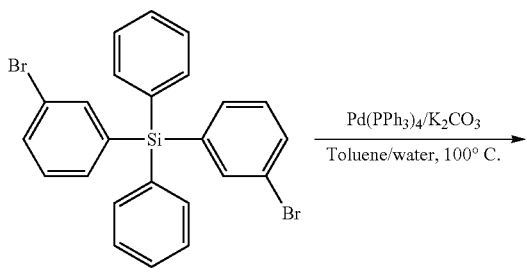

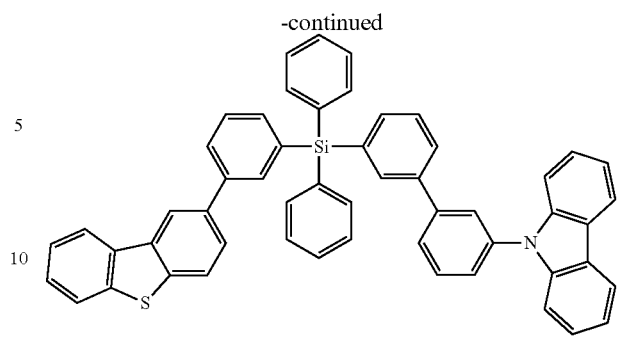

Compound 31

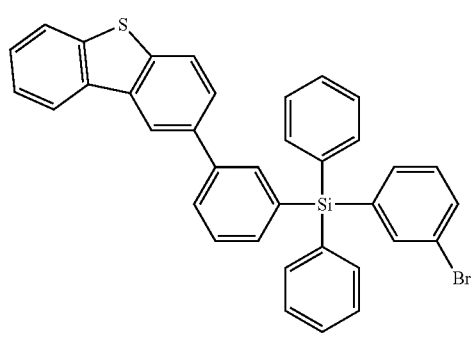

A mixture solution of bis(3-bromophenyl)diphenylsilane (10.84 g, 21.92 mmol), dibenzo[b,d]thiophen-2-yl boronic acid (2.000 g, 8.77 mmol), Pd(PPh$_3$)$_4$ (0.101 g, 0.088 mmol) and K$_2$CO$_3$ (2.424 g, 17.54 mmol) in toluene (200 mL) and water (50 mL) was refluxed under nitrogen overnight. After cooling to room temperature, the organic phase was isolated and evaporated to dryness. The residue was purified by column chromatography on silica gel with hexane:DCM (9:1, v/v) as eluent to yield (3-bromophenyl)(3-(dibenzo[b,d]thiophen-2-yl)phenyl)diphenylsilane (3.16 g, 60% yield) as a white solid.

A suspension of (3-bromophenyl)(3-(dibenzo[b,d]thiophen-2-yl)phenyl)diphenylsilane (3.16 g, 5.29 mmol), 9-(3-(4,4,5,5-tetramethyl-1,3,2-dioxaborolan-2-yl)phenyl)-9H-carbazole (1.952 g, 5.29 mmol), Pd$_2$(dba)$_3$ (0.048 g, 0.053 mmol), SPhos (0.043 g, 0.106 mmol) and K$_3$PO$_4$ (2.435 g, 10.57 mmol) in toluene (200 mL) and water (5 mL) was heated at 60° C. under nitrogen overnight. After cooling to room temperature, the organic phase was isolated and evaporated to dryness. The residue was purified by column chromatography on silica gel with hexane:DCM (9:1 to 7:3, v/v) as eluent to yield Compound 31 (3.2 g, 80%) as a white solid.

Example 10

Synthesis of Compound 32

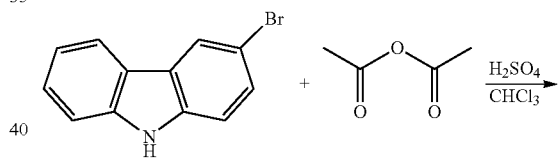

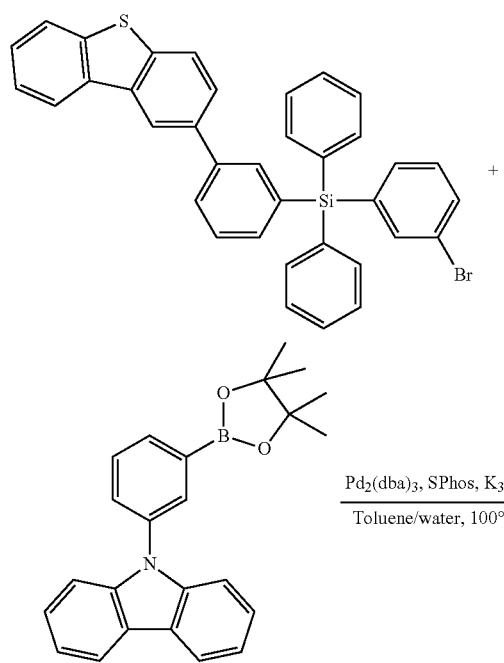

A solution of 3-bromo-9H-carbazole (10.00 g, 40.6 mmol), acetic anhydride (8.30 g, 81 mmol) together with 2 drops of H$_2$SO$_4$ in chloroform (150 mL) was refluxed overnight. After cooling to room temperature, the solution was washed with water. Upon evaporation of the solvent, the crude product was purified by crystallization from hexane/DCM and hexane/EtOAc to yield 1-(3-bromo-9H-carbazol-9-yl)ethanone (6.1 g, 51% yield) as a light yellow solid.

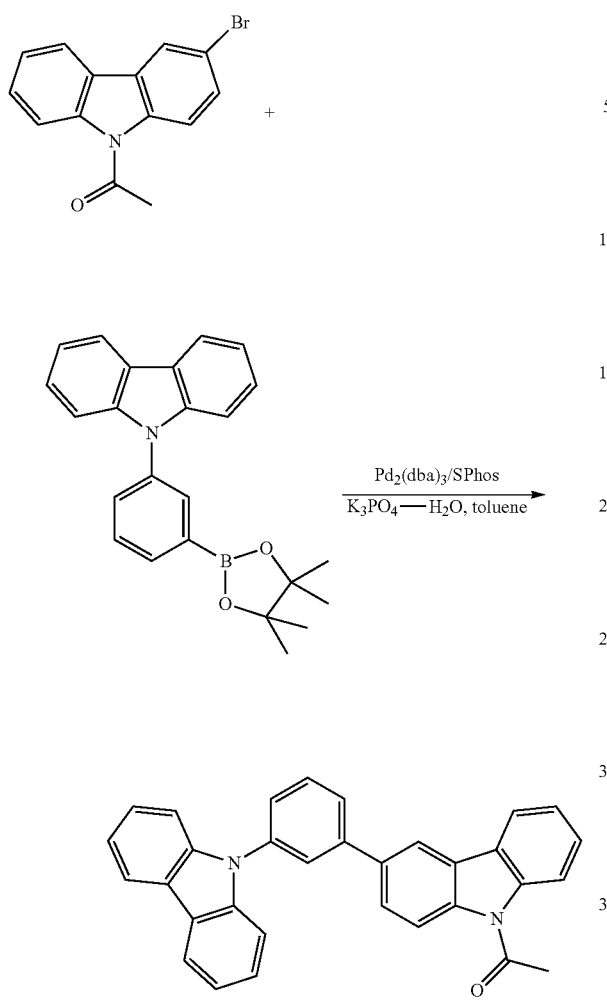

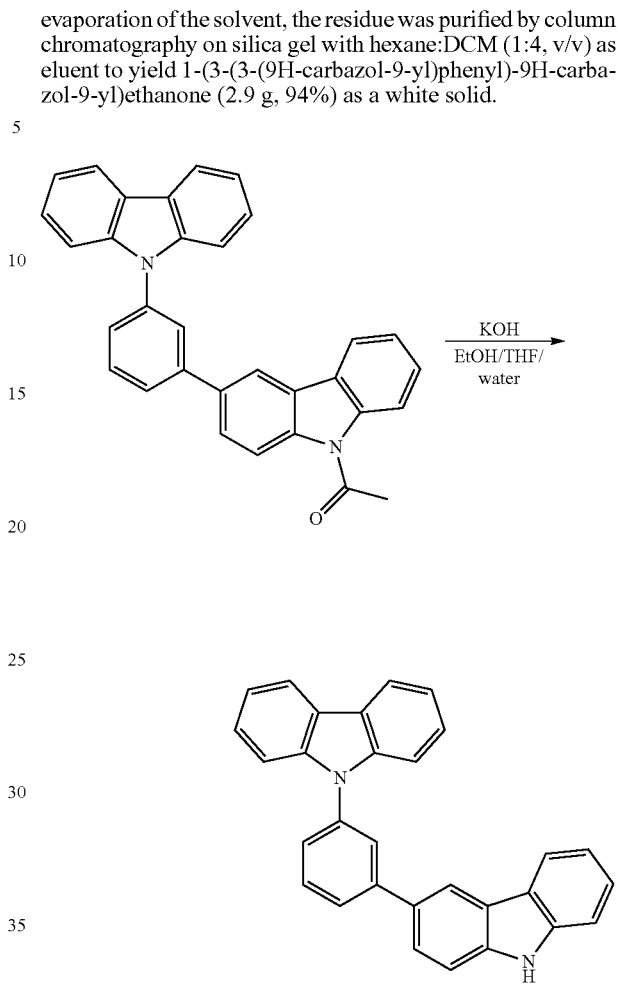

evaporation of the solvent, the residue was purified by column chromatography on silica gel with hexane:DCM (1:4, v/v) as eluent to yield 1-(3-(3-(9H-carbazol-9-yl)phenyl)-9H-carbazol-9-yl)ethanone (2.9 g, 94%) as a white solid.

A solution of 1-(3-bromo-9H-carbazol-9-yl)ethanone (2.000 g, 6.94 mmol), 9-(3-(4,4,5,5-tetramethyl-1,3,2-dioxaborolan-2-yl)phenyl)-9H-carbazole (2.56 g, 6.94 mmol), Pd$_2$(dba)$_3$ (0.064 g, 0.069 mmol), SPhos (0.057 g, 0.139 mmol) and potassium phosphate tribasic hydrate (4.80 g, 20.82 mmol) in toluene (100 mL) and water (10 mL) was stirred at 70° C. under nitrogen overnight. After cooling to room temperature, the organic phase was isolated. Upon A mixture of 1-(3-(3-(9H-carbazol-9-yl)phenyl)-9H-carbazol-9-yl)ethanone (3.50 g, 7.77 mmol) and potassium hydroxide (1.308 g, 23.31 mmol) in EtOH (250 mL), THF (100 mL), and water (25 mL) was refluxed for 3 h. The organic solvent was evaporated, and the aqueous phase was extracted with EtOAc. The extracts were combined and passed through a short plug of silica gel and concentrated. Upon addition of hexane, the product 3-(3-(9H-carbazol-9-yl)phenyl)-9H-carbazole (3.0 g, 95%) precipitated as white shining crystals.

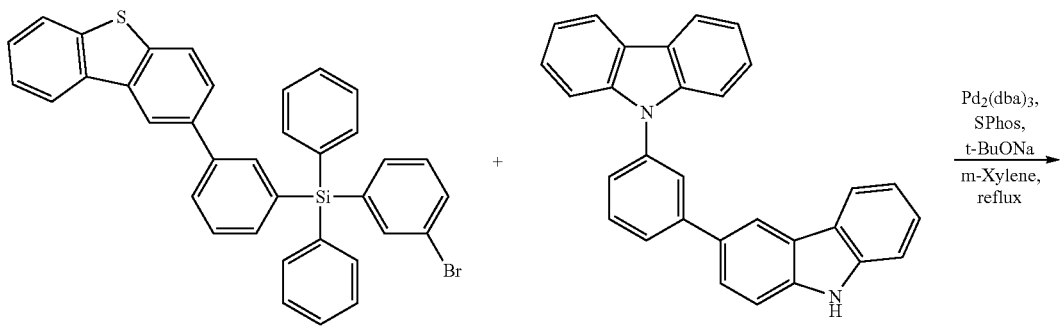

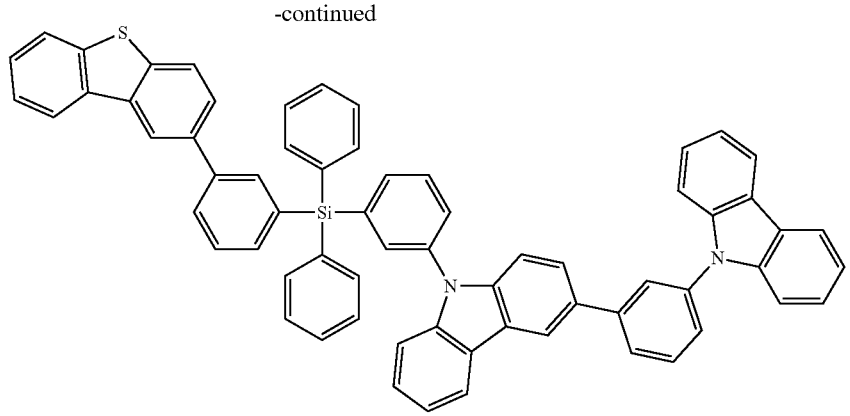

Compound 32

A suspension of 3-(3-(9H-Carbazol-9-yl)phenyl)-9H-carbazole (2.000 g, 4.90 mmol), (3-bromophenyl)(3-(dibenzo[b,d]thiophen-2-yl)phenyl)diphenylsilane (2.93 g, 4.90 mmol), sodium tert-butoxide (0.941 g, 9.79 mmol), Pd$_2$(dba)$_3$ (0.090 g, 0.098 mmol) and SPhos (0.040 g, 0.098 mmol) in xylene (200 mL) was refluxed under nitrogen for 18 h. After cooling to room temperature, the solvent was evaporated and the crude product was purified by column chromatography on silica gel with hexane:DCM (3/1, v/v) as eluent to yield Compound 32 (3.0 g, 66%) as a white solid.

Example 11

Synthesis of Compound 33

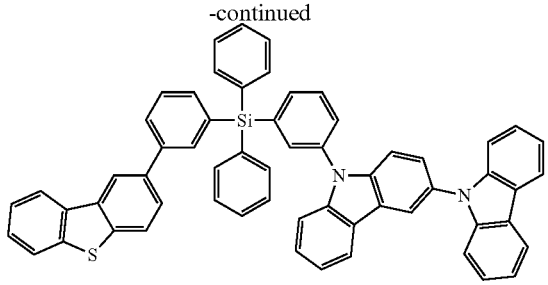

Compound 33

A suspension of (3-bromophenyl)(3-(dibenzo[b,d]thiophen-2-yl)phenyl)diphenylsilane (3 g, 5.02 mmol), 9H-3,9'-bicarbazole (1.835 g, 5.52 mmol), Pd$_2$(dba)$_3$ (0.092 g, 0.100 mmol), SPhos (0.082 g, 0.201 mmol), and sodium tert-butoxide (0.965 g, 10.04 mmol) in m-xylene (50 mL) was refluxed at 140° C. under nitrogen. After cooling to room temperature the reaction was quenched with water, extracted with toluene, and dried over MgSO$_4$. Upon evaporation of the solvent, the crudue product was purified by column chromatography with hexane:DCM (8:2, v/v) as eluent to yield Compound 33 as a white powder (3.4 g, 80%).

Example 12

Synthesis of Compound 34

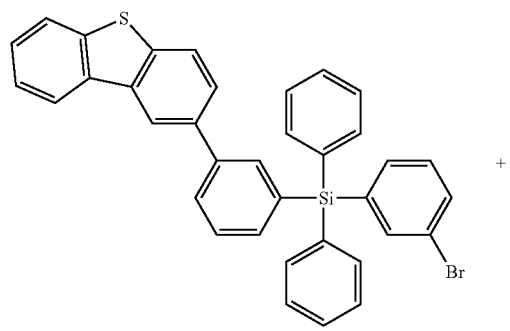

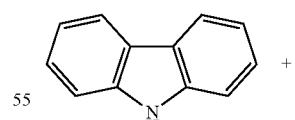

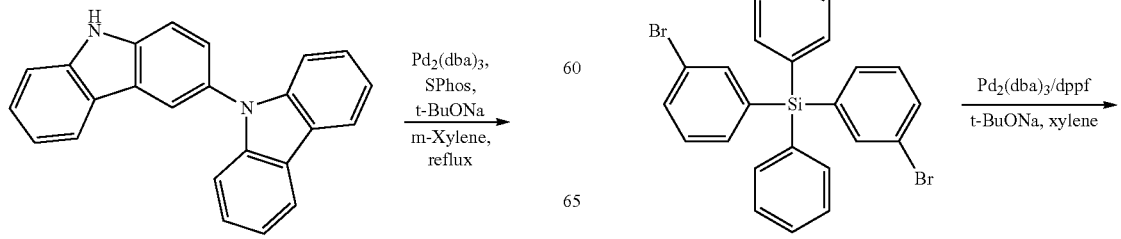

-continued

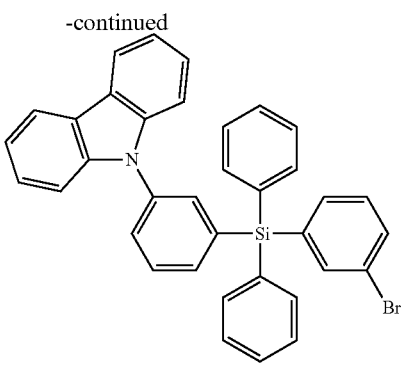

A suspension of 9H-carbazole (3.60 g, 21.53 mmol), bis(3-bromophenyl)diphenylsilane (21.28 g, 43.1 mmol), Pd₂(dba)₃ (0.394 g, 0.431 mmol), 1,1'-Bis(diphenylphosphino)ferrocene (dppf, 0.394 g, 0.431 mmol) and sodium tert-butoxide (4.14 g, 43.1 mmol) in xylene (150 mL) was refluxed under nitrogen overnight. After cooling to room temperature, the organic solution was isolated by filtration. Upon evaporation of the solvent, the crude product was purified by column chromatography on silica gel with hexane:EtOAc (9:1, v/v) as eluent to yield 9-(3-((3-bromophenyl)diphenylsilyl)phenyl)-9H-carbazole (6.1 g, 49%) as white solid

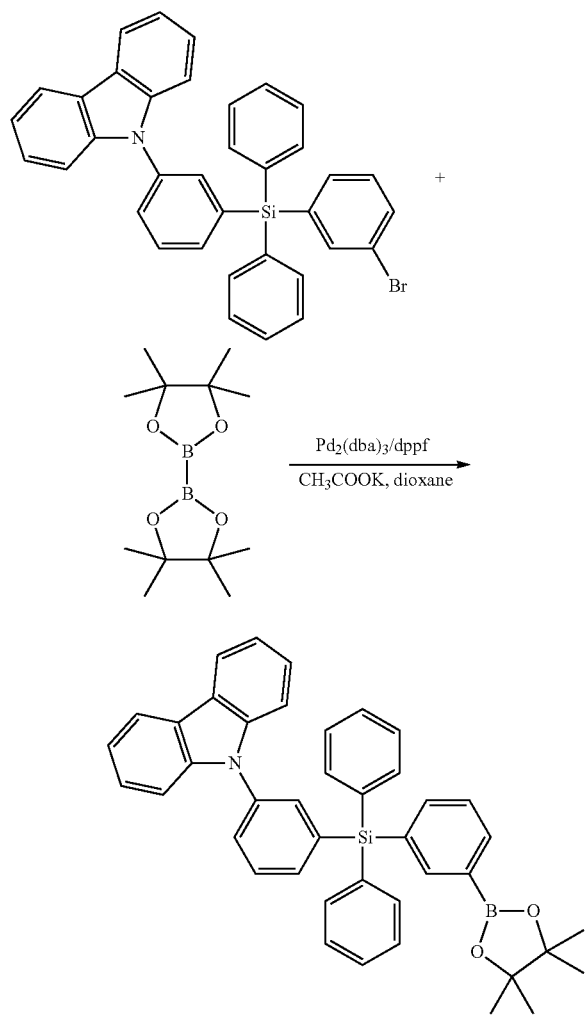

A solution of 9-(3-((3-bromophenyl)diphenylsilyl)phenyl)-9H-carbazole (6.00 g, 10.33 mmol), 4,4,4',4',5,5,5',5'-octamethyl-2,2'-bi(1,3,2-dioxaborolane) (3.15 g, 12.40 mmol), potassium acetate (1.014 g, 10.33 mmol), Pd₂(dba)₃ (9.46 g, 10.33 mmol) and dppf (6.31 g, 10.33 mmol) in dioxane (200 mL) was refluxed under nitrogen overnight. After cooling to room temperature, the black reaction mixture was diluted with water, extracted with EtOAc and dried over Na₂SO₄. Upon evaporation of the solvent, the crude product was purified by column chromatography on silica gel with hexane:EtOAc (9:1, v/v) as eluent to yield 9-(3-(diphenyl(3-(4,4,5,5-tetramethyl-1,3,2-dioxaborolan-2-yl)phenyl)silyl)phenyl)-9H-carbazole (3.26 g, 50%) as a white solid.

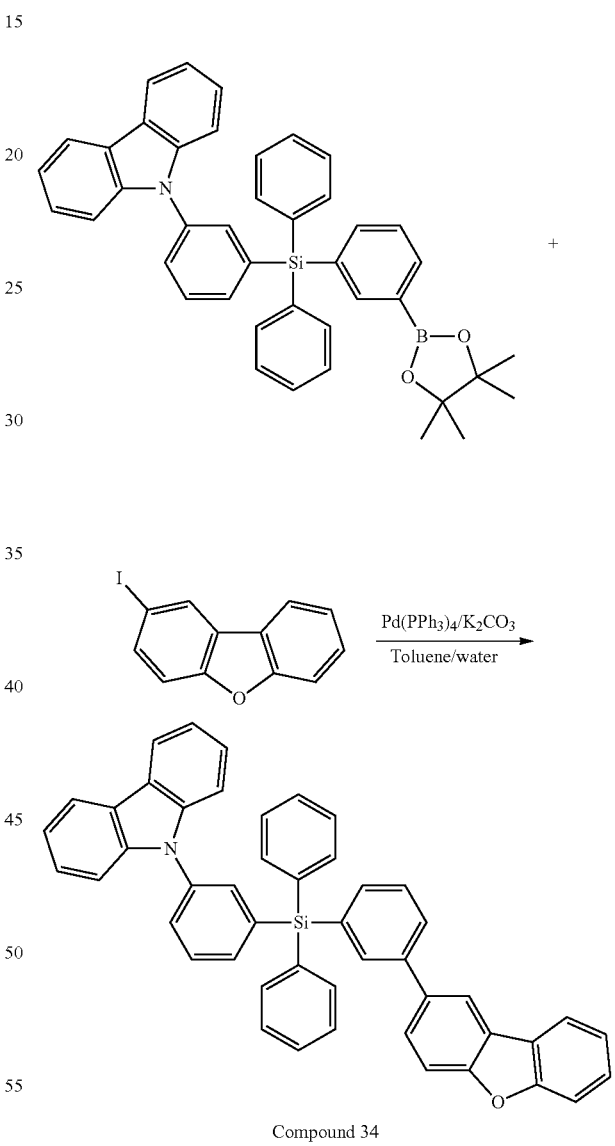

Compound 34

A solution of 9-(3-(diphenyl(3-(4,4,5,5-tetramethyl-1,3,2-dioxaborolan-2-yl)phenyl)silyl)phenyl)-9H-carbazole (3.25 g, 5.18 mmol), 2-iododibenzo[b,d]furan (1.523 g, 5.18 mmol), K₂CO₃ (1.431 g, 10.36 mmol) and Pd(PPh₃)₄ (0.096 g, 0.083 mmol) in toluene (100 mL) and water (5 mL) was refluxed under nitrogen overnight. After cooling to room temperature, the organic phase was isolated. Upon evaporation of the solvent, the residue was purified by column chromatography on silica with hexane:DCM (7:3, v/v) as eluent to yield Compound 34 (2.55 g, 74%) as a white solid.

Example 13

Synthesis of Compound 35

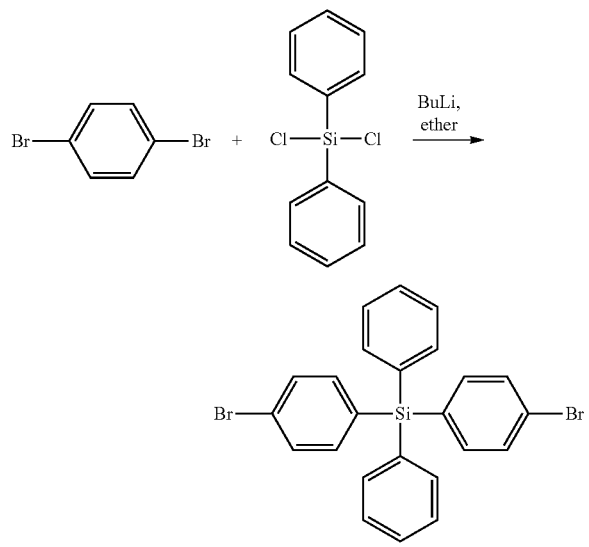

Into a solution of 1,4-dibromobenzene (34 g, 144 mmol) in diethyl ether (600 mL) was added 2.5M butyllithium solution in hexane (60.3 mL, 151 mmol) dropwise at −78° C. The solution was stirred at −78° C. for 3.5 hours before dichlorodiphenylsilane (13.49 mL, 65.5 mmol) dissolved in 20 ml of diethyl ether was added dropwise. The reaction mixture was allowed to warm up to room temperature overnight and was quenched with water. The organic phase was isolated, filtered to remove solids, and dried over $Na_2SO_4$. After evaporation of the solvent, the residue was purified by column chromatography on silica gel with hexane:toluene as eluent and precipitation from toluene to methanol to yield bis(4-bromophenyl)diphenylsilane (12 g, 37%) as a white powder.

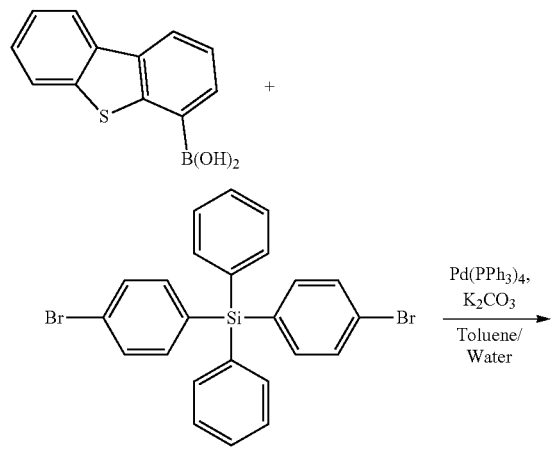

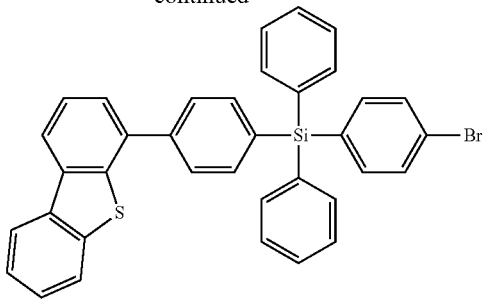

A mixture solution of dibenzo[b,d]thiophen-4-ylboronic acid (2.5 g, 10.96 mmol), bis(4-bromophenyl)diphenylsilane (11.92 g, 24.11 mmol), $Pd(PPh_3)_4$ (0.253 g, 0.219 mmol), and $K_2CO_3$ (9.09 g, 65.8 mmol) in toluene (90 mL) and water (30 mL) was stirred at 90° C. under nitrogen overnight. After cooling to room temperature, the organic phase was isolated, and the aqueous phase was extracted with toluene. The combined organic solution was dried over $Na_2SO_4$. Upon evaporation of the solvent, the residue was purified by column chromatography on silica gel with hexane:DCM(9/1, v/v) as eluent to yield (4-bromophenyl)(4-(dibenzo[b,d]thiophen-4-yl)phenyl)diphenylsilane (5.2 g, 79%) as a white powder.

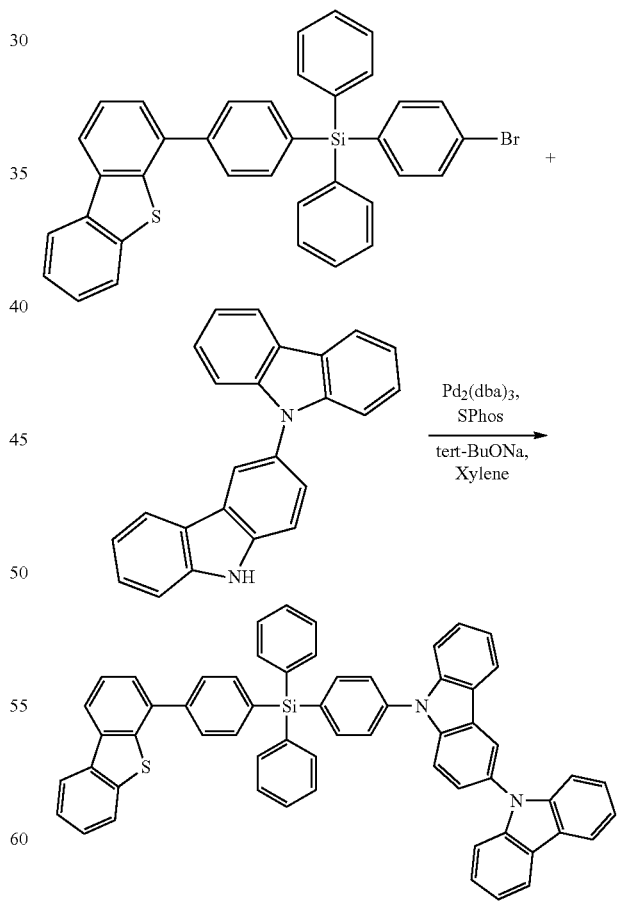

Compound 35

A suspension of (4-bromophenyl)(4-(dibenzo[b,d]thiophen-4-yl)phenyl)diphenylsilane (2.83 g, 4.74 mmol), 9H-3,9'-bicarbazole (1.731 g, 5.21 mmol), Pd$_2$(dba)$_3$ (0.087 g, 0.095 mmol), SPhos (0.078 g, 0.189 mmol), and sodium tert-butoxide (0.910 g, 9.47 mmol) in xylene (50 mL) was refluxed at 140° C. overnight. After cooling to room temperature, it was passed through a short plug of Celite, washed with toluene and DCM. The combined solution was evaporated, and the residue was purified by column chromatography on silica gel with hexane:DCM(7.5:2.5, v/v) as eluent to yield Compound 35 (3.76 g, 94%) as a white powder.

Example 14

Synthesis of Compound 36

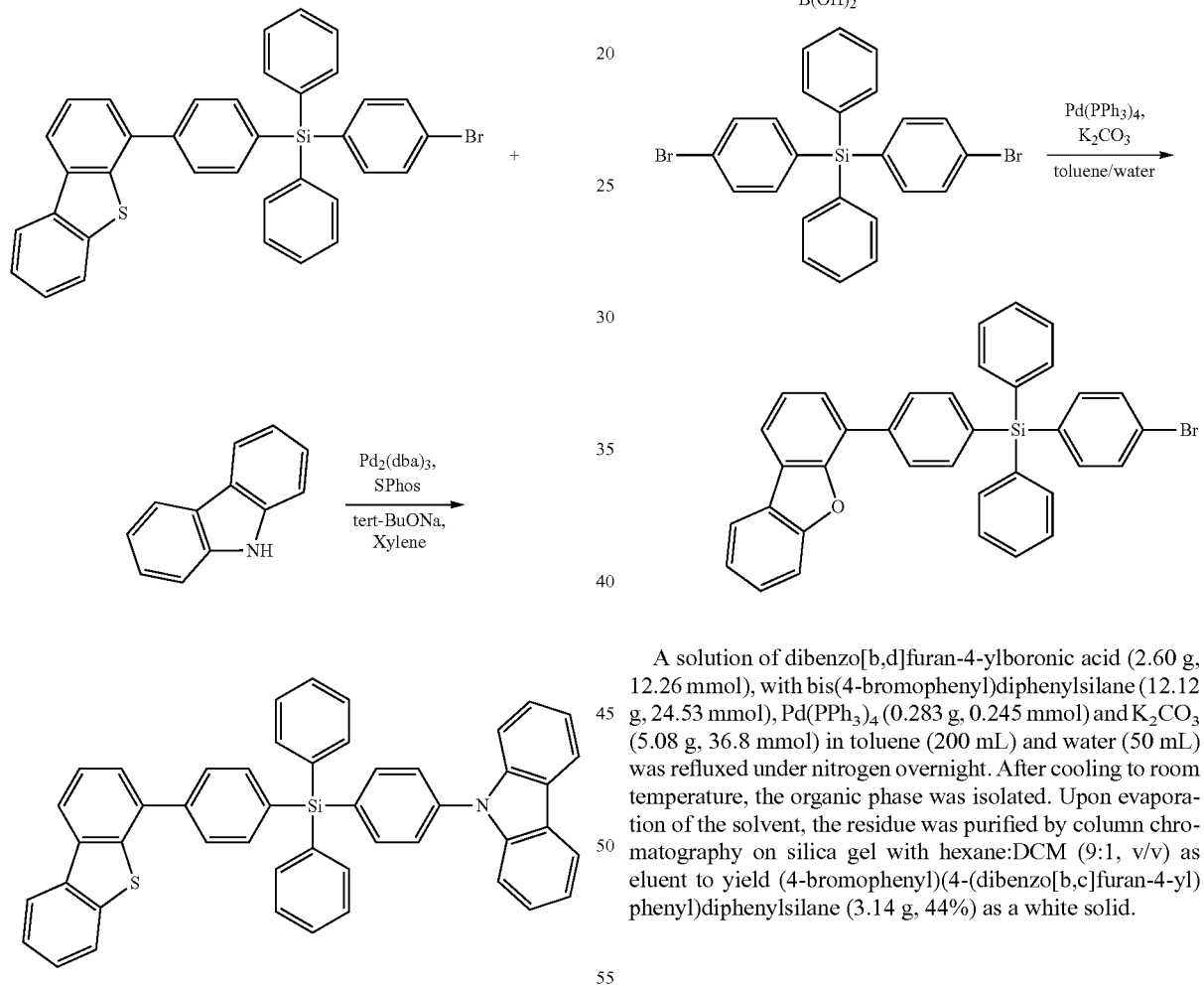

Compound 36

A suspension of (4-bromophenyl)(4-(dibenzo[b,d]thiophen-4-yl)phenyl)diphenylsilane (2.83 g, 4.74 mmol), 9H-carbazole (0.808 g, 4.83 mmol), Pd$_2$(dba)$_3$ (0.087 g, 0.095 mmol), SPhos (0.078 g, 0.189 mmol), and sodium tert-butoxide (0.910 g, 9.47 mmol) in m-xylene (50 mL) was heated at 140° C. for 5 h. After cooling to room temperature, the solution was washed with aqueous ammonium chloride and water, dried over Na$_2$SO$_4$, and passed through a short plug of Celite. Upon evaporation of the solvent, the residue was purified by column chromatography on silica gel with hexane:DCM (8:2, v/v) as eluent to yield Compound 36 (1.50 g, 46.3%) as a white powder.

Example 15

Synthesis of Compound 37

A solution of dibenzo[b,d]furan-4-ylboronic acid (2.60 g, 12.26 mmol), with bis(4-bromophenyl)diphenylsilane (12.12 g, 24.53 mmol), Pd(PPh$_3$)$_4$ (0.283 g, 0.245 mmol) and K$_2$CO$_3$ (5.08 g, 36.8 mmol) in toluene (200 mL) and water (50 mL) was refluxed under nitrogen overnight. After cooling to room temperature, the organic phase was isolated. Upon evaporation of the solvent, the residue was purified by column chromatography on silica gel with hexane:DCM (9:1, v/v) as eluent to yield (4-bromophenyl)(4-(dibenzo[b,c]furan-4-yl)phenyl)diphenylsilane (3.14 g, 44%) as a white solid.

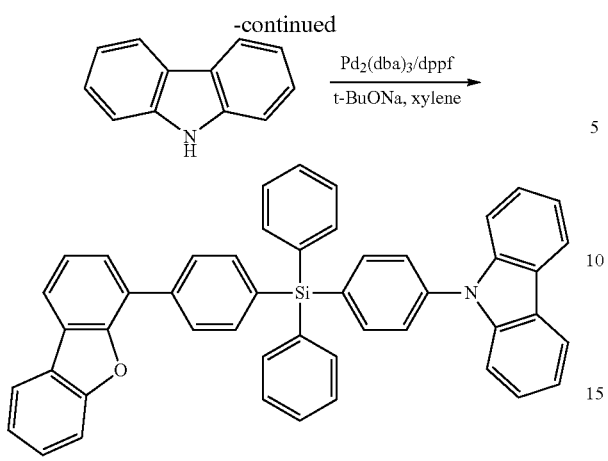

Compound 37

A suspension of (4-bromophenyl)(4-(dibenzo[b,d]furan-4-yl)phenyl)diphenylsilane (3.15 g, 5.42 mmol), 9H-carbazole (0.996 g, 5.96 mmol), sodium tert-butoxide (1.041 g, 10.83 mmol) Pd$_2$(dba)$_3$ (0.099 g, 0.108 mmol) and dppf (0.066 g, 0.108 mmol) in xylene (150 mL) was refluxed under nitrogen for 24 h. After cooling to room temperature, the reaction mixture was filtered. Upon evaporation of the solvent, the residue was purified by column chromatography on silica with hexane:EtOAc (4:1, v/v) as eluent to yield Compound 37 (3.4 g, 94%) as a white solid.

Example 16

Synthesis of Compound 38

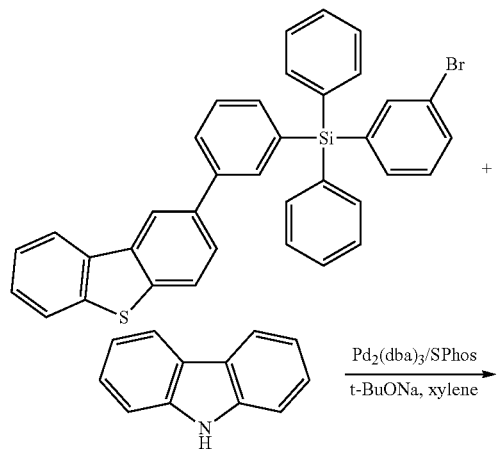

Compound 38

A suspension of (3-bromophenyl)(3-(dibenzo[b,d]thiophen-2-yl)phenyl)diphenylsilane (3.81 g, 6.38 mmol), 9H-carbazole (1.173 g, 7.01 mmol), Pd$_2$(dba)$_3$ (0.117 g, 0.128 mmol), SPhos (0.105 g, 0.255 mmol), and sodium tert-butoxide (1.225 g, 12.75 mmol in xylene (200 mL) was refluxed under nitrogen overnight. After cooling to room temperature, the organic solution was isolated by filtration. Upon evaporation of the solvent, the residue was purified by column chromatography on silica gel with hexane:DCM (4:1 to 1:1, v/v) as eluent to yield Compound 38 (2.2 g, 50%) as a white solid.

Comparative Examples

Comparative Examples 1

Synthesis of Comparative Compound CC-1

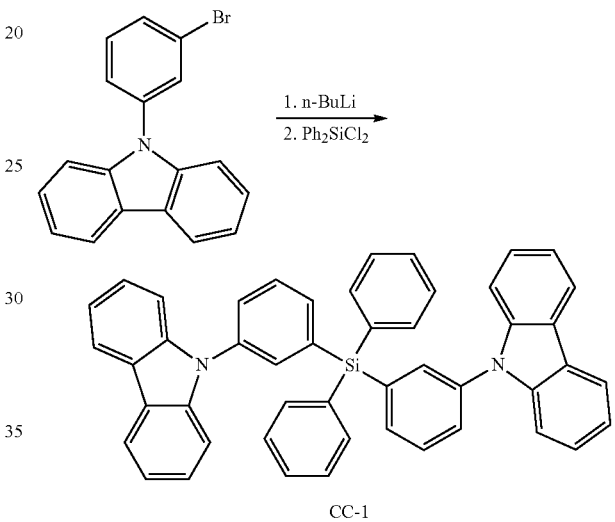

CC-1

Into a solution of 9-(3-bromophenyl)-9H-carbazole (5 g, 15.52 mmol) in THF (50 mL) was added n-butyllithium (9.7 mL, 15.5 mmol, 1.6 M in hexane) dropwise at −78° C., and the mixture was stirred for 2 h at −78° C. In a separate flask, dichlorodiphenylsilane (1.5 mL, 7.1 mmol) was dissolved in 10 mL of THF and added dropwise to reaction mixture, which was then allowed to warm to room temperature overnight. Ethyl acetate (50 mL) and water (50 mL) were added and the layers separated. The aqueous layer was washed twice more with EtOAc and combined organics were washed with water and brine. Upon evaporation of the solvent, the residue was purified by column chromatography on silica gel with hexane:DCM (7/3, v/v) as eluent, recrystallization from hexane, and sublimation twice under vacuum (<10$^{-5}$ Torr) to yield CC-1 (1.7 g) as white crystals.

Comparative Examples 2

Synthesis of Comparative Compound CC-2

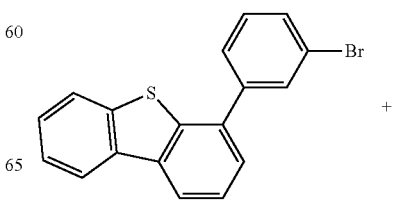

-continued

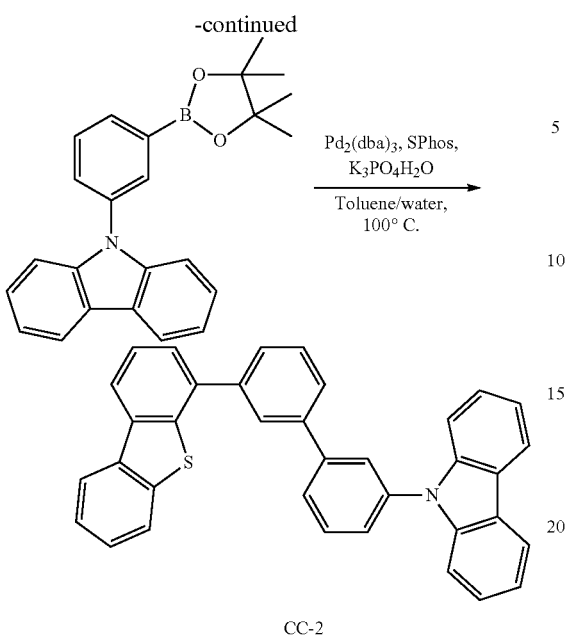

CC-2

A solution of 4-(3-bromophenyl)dibenzo[b,d]thiophene (7.15 g, 21.08 mmol), 9-(3-(4,4,5,5-tetramethyl-1,3,2-dioxaborolan-2-yl)phenyl)-9H-carbazole (7.78 g, 21.08 mmol), SPhos (0.173 g, 0.422 mmol), $Pd_2(dba)_3$ (0.192 g, 0.211 mmol) and potassium phosphate monohydrate (9.71 g, 42.2 mmol) in toluene (200 mL) and water (10 mL) was refluxed under nitrogen overnight. After cooling to room temperature, the organic phase was isolated and evaporated to dryness. The residue was purified by column chromatography on silica gel with hexane:DCM (9:1 to 1:1, v/v) as eluent, recrystallization from heptane, and sublimation under vacuum to yield CC-2 (6.4g, 61%) as white crystals.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The invention claimed is:

1. A compound of Formula I comprising:

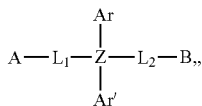

Formula I wherein Ar and Ar' are independently selected from the group consisting of phenyl, biphenyl, napthyl, dibenzothiolyl, and dibenzofuranyl, which are optionally further substituted;
wherein Z is selected from Si and Ge;
wherein $L_1$ comprises aryl or heteroaryl groups, wherein any heteroatoms in the heteroaryl groups are nitrogen;
wherein $L_2$ comprises aryl or heteroaryl groups, wherein any heteroatoms in the heteroaryl groups are nitrogen;
wherein $L_1$ and $L_2$ are optionally further substituted;
wherein A contains a group selected from the group consisting of dibenzofuran, dibenzothiophene, azadibenzofuran, azadibenzothiophene, dibenzoselenophene and azadibenzoselenophene, which are optionally further substituted, and wherein the substitution is optionally fused to at least one benzo ring; and
wherein B contains a group selected from the group consisting of carbazole and azacarbazole, which are optionally further substituted, and wherein the substitution is optionally fused to the carbazole or azacarbazole group.

2. The compound of claim 1, wherein A is selected from the group consisting of:

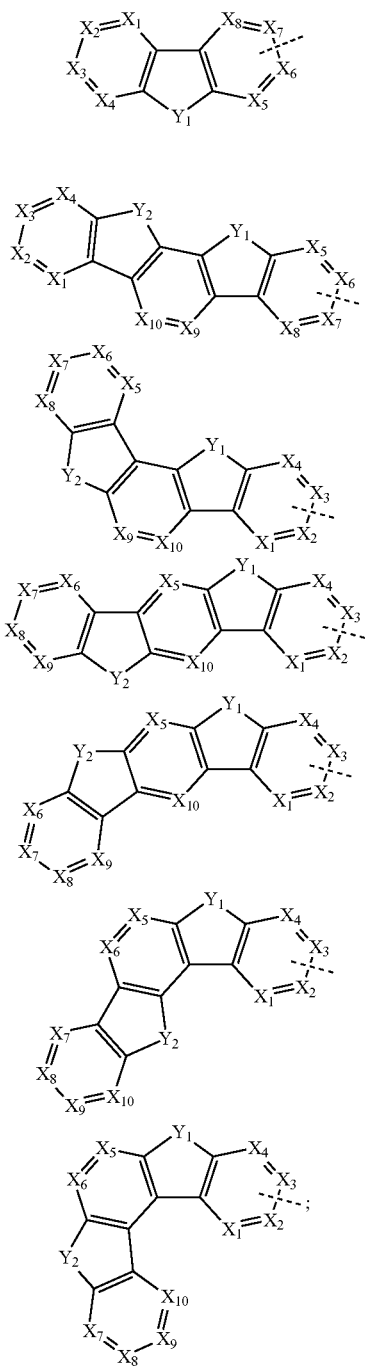

wherein B is selected from the group consisting of:
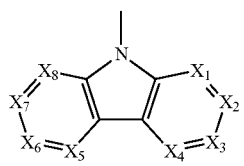
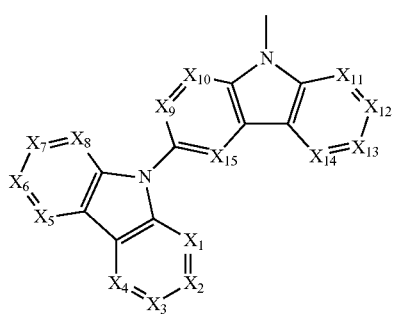
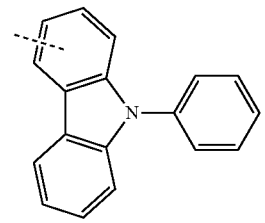
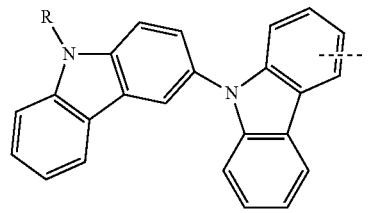
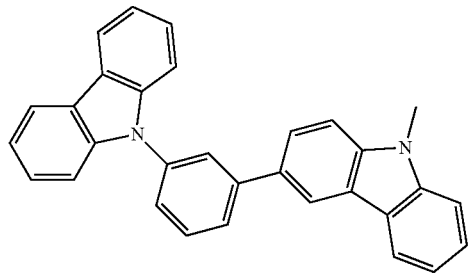
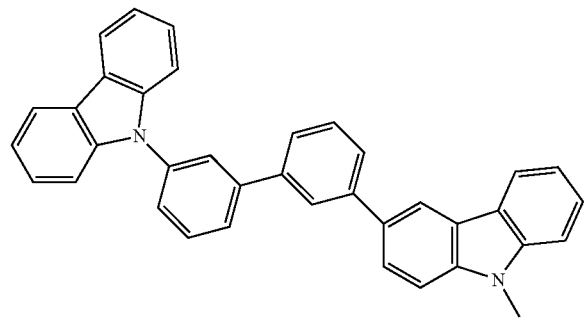
-continued
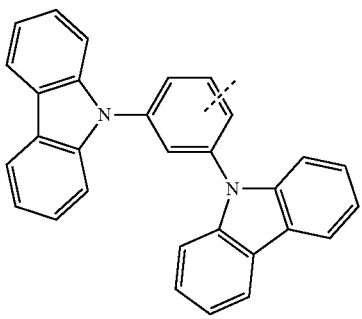
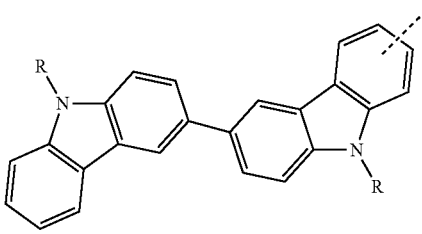
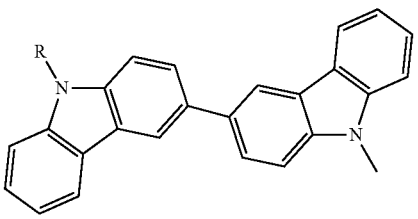
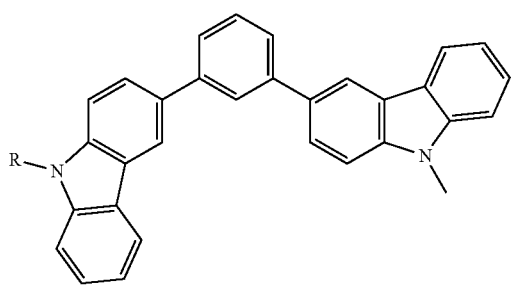
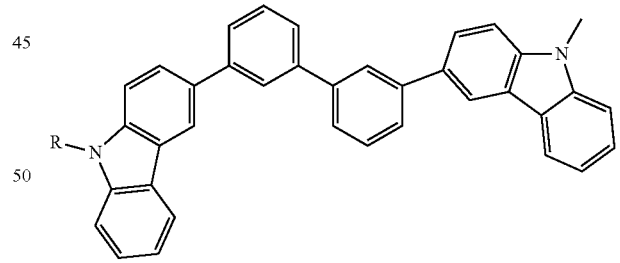
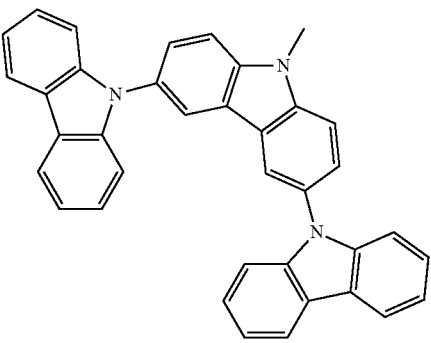

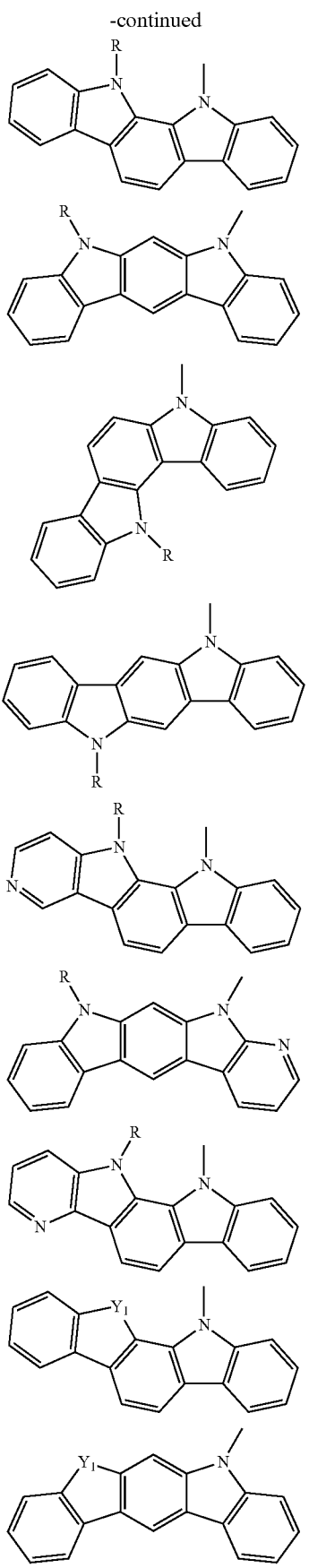

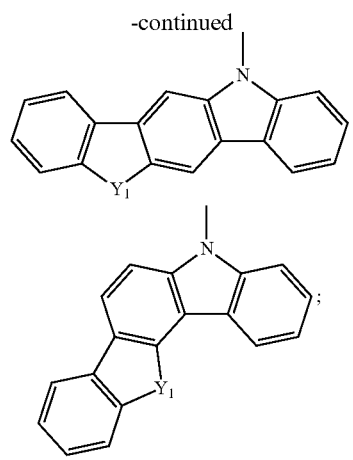

wherein $Y_1$ and $Y_2$ are independently selected from the group consisting of O, S, and Se;

wherein $X_1$ to $X_{10}$ are independently selected from the group consisting of CR and N, and wherein each benzo ring contains at most one N;

wherein R is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

3. The compound of claim 1, wherein $L_1$ and $L_2$ are independently selected from the group consisting of:

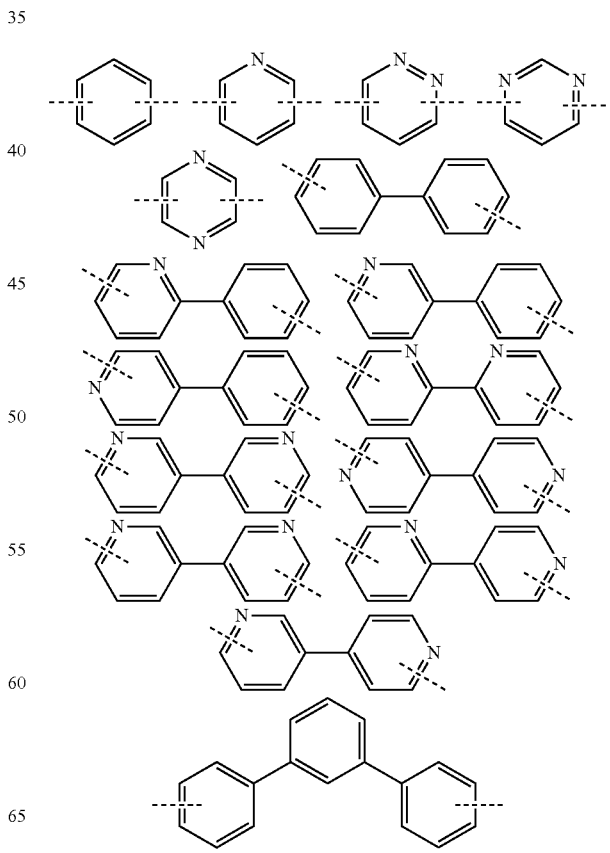

143
-continued

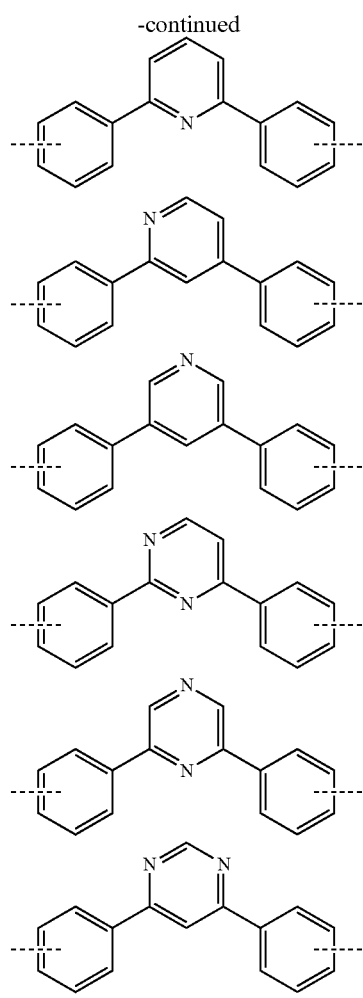

144
-continued

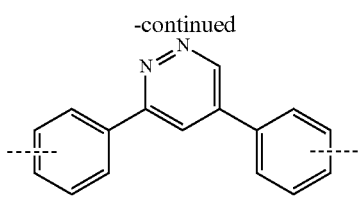

4. The compound of claim 1, wherein $L_1$ and $L_2$ contain at least one phenyl bonded directly to Z.

5. The compound of claim 1, wherein Ar and Ar' are phenyl.

6. The compound of claim 1, wherein Ar, Ar', A and B are independently substituted with at least one group selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

7. The compound of claim 6, wherein aryl comprises phenyl, biphenyl, triphenyl, terphenyl, naphthalene, phenalene, phenanthrene, fluorene or chiysene; and wherein heteroaryl comprises dibenzothiophene, dibenzofuran, benzofuran, benzothiophene, pyrazole, imidazole, triazole, oxazole, thiazole, oxadiazole, oxatriazole, dioxazole, thiadiazole, pyridine, pyridazine, pyrimidine, pyrazine, triazine, indole, azaindole, benzimidazole, indazole, benzoxazole, benzisoxazole, benzothiazole, quinoline, isoquinoline, cinnoline, quinazoline, quinoxaline, naphthyridine, phthalazine, pteridine, xanthene, phenothiazine, phenoxazine, benzofuropyridine, furodipyridine, benzothienopyridine and thienodipyridine.

8. The compound of claim 1, wherein the compound is selected from the group consisting of Compound 1

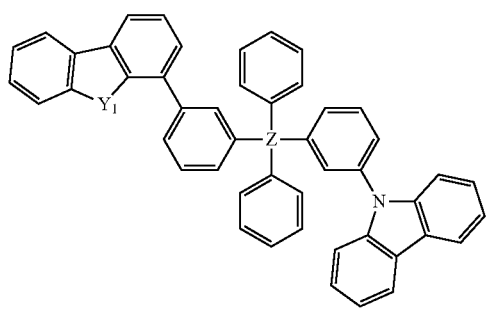

Compound 2

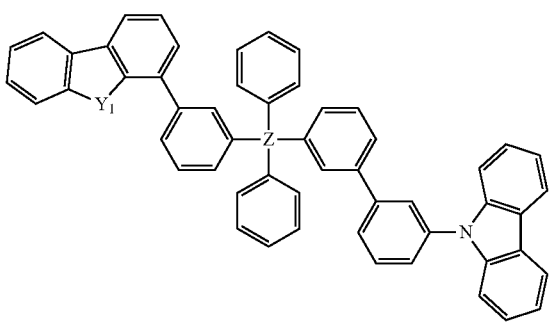

Compound 3

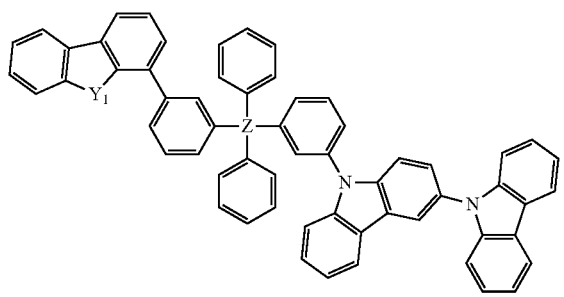

Compound 4

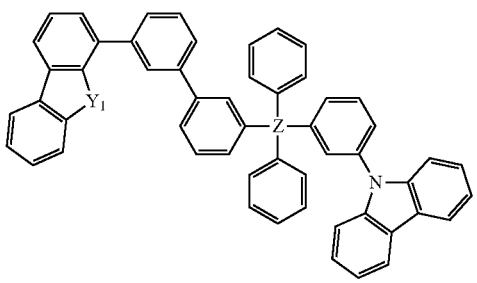

Compound 5
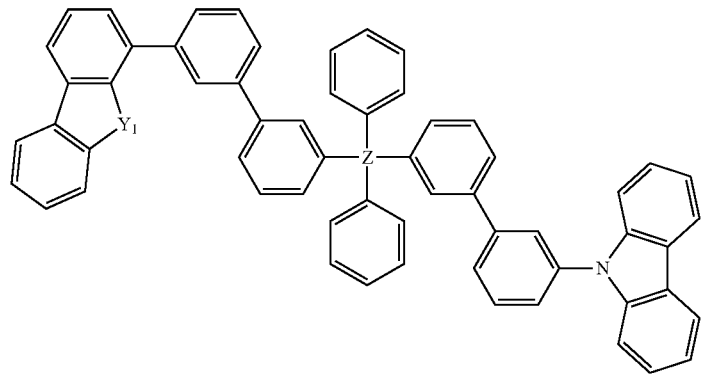
Compound 6
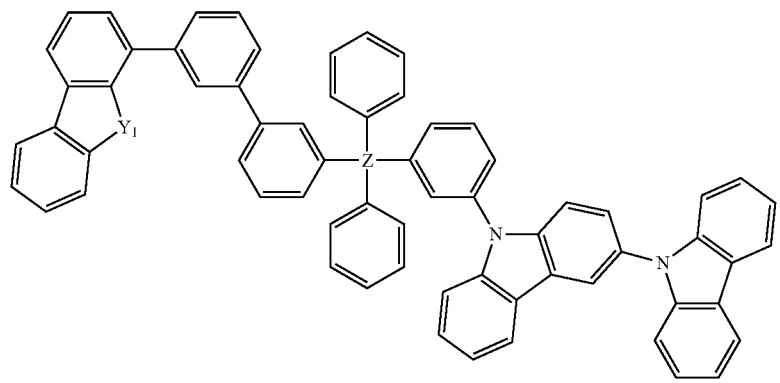
Compound 7
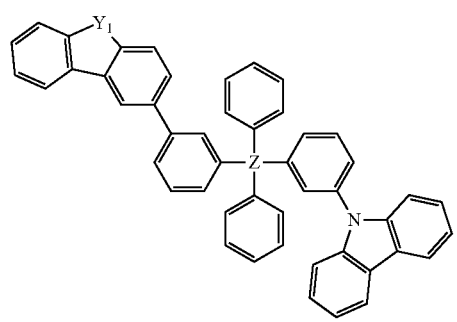
Compound 8
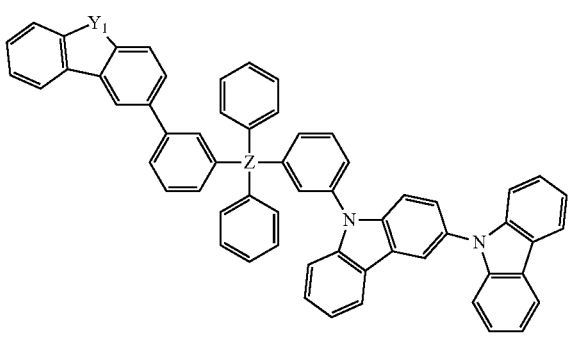
Compound 9
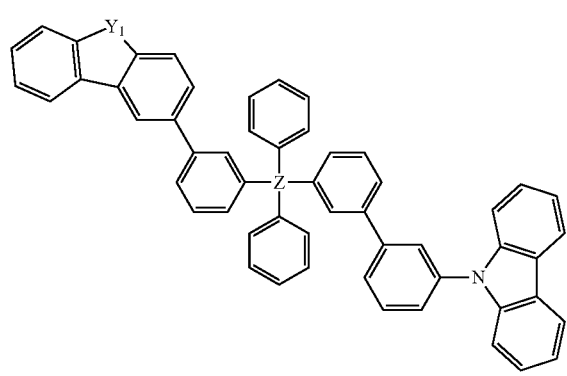
Compound 10
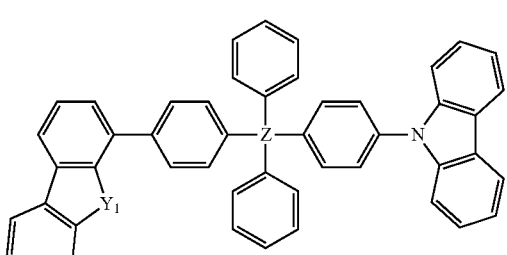

-continued
Compound 11
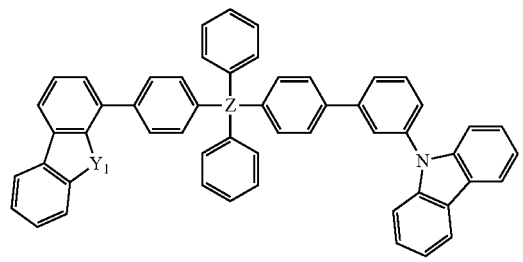
Compound 12
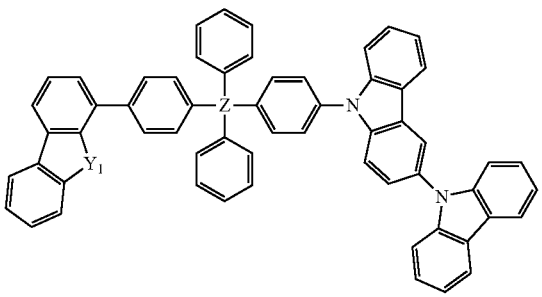
Compound 13
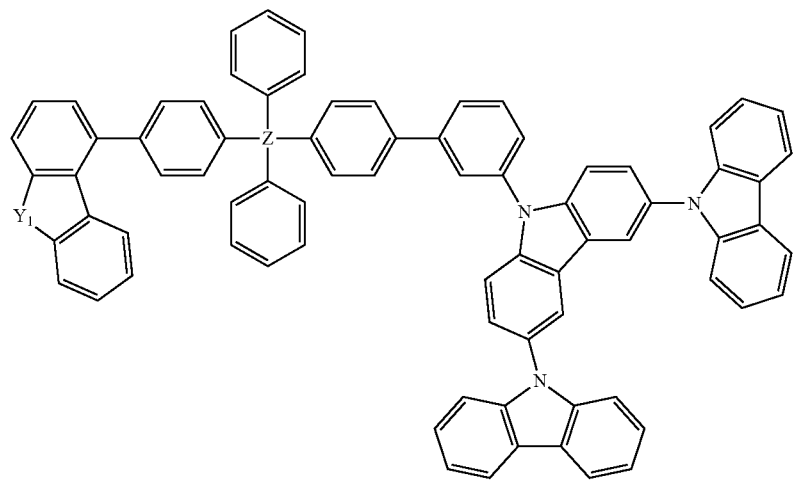
Compound 14
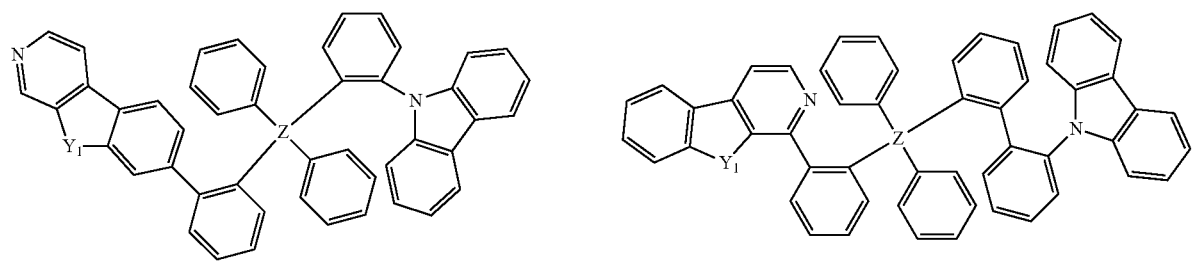
Compound 15
Compound 16
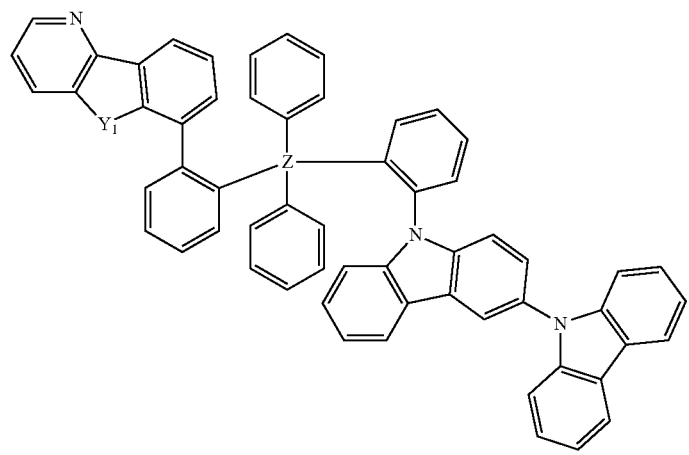

Compound 17
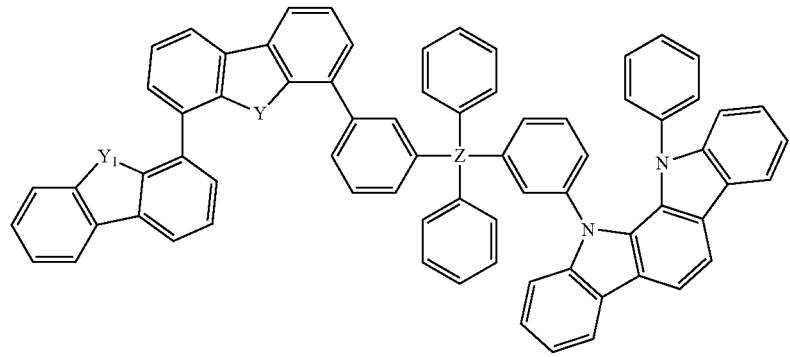
Compound 18
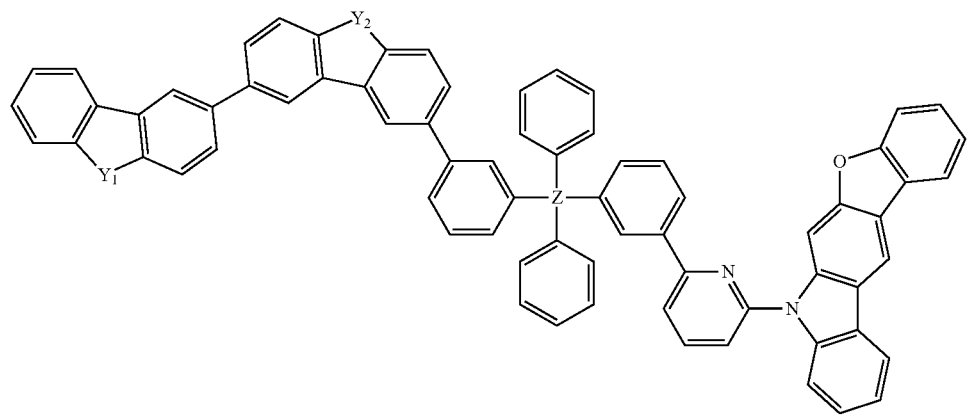
Compound 19
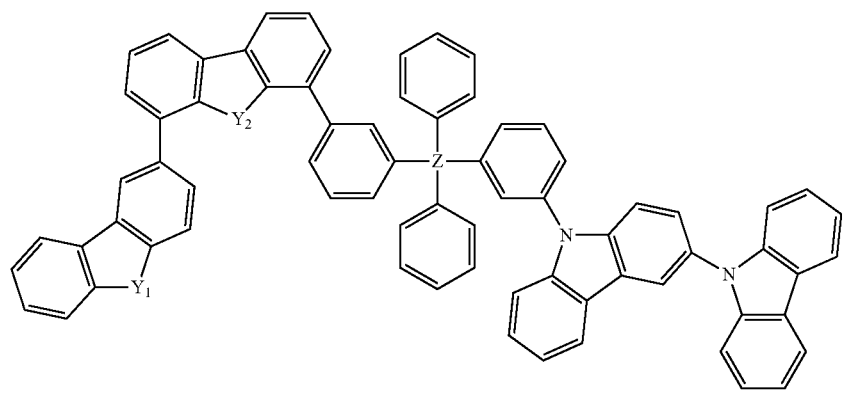
Compound 20
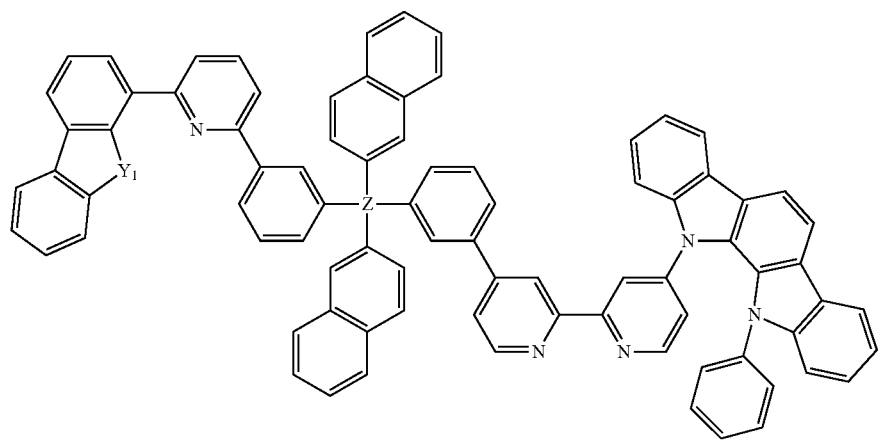

-continued
Compound 21
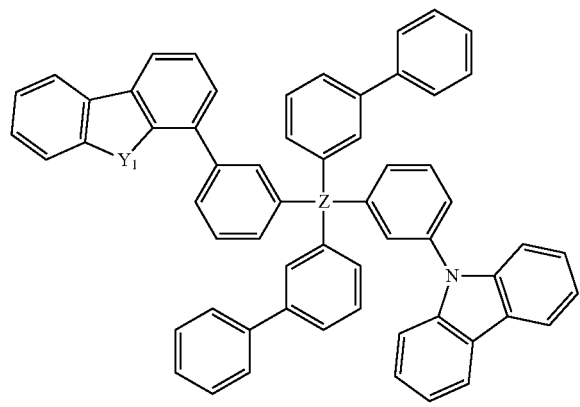
Compound 22
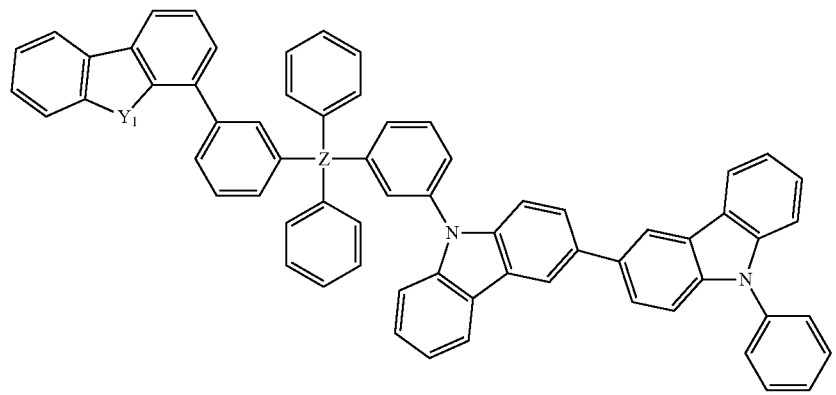
wherein $Y_1$ and $Y_2$ are independently selected from the group consisting of O, S and Se; and wherein Z is selected from the group consisting of Si and Ge.
9. The compound of claim 1, wherein the compound is selected from the group consisting of
Compound 23
Compound 24
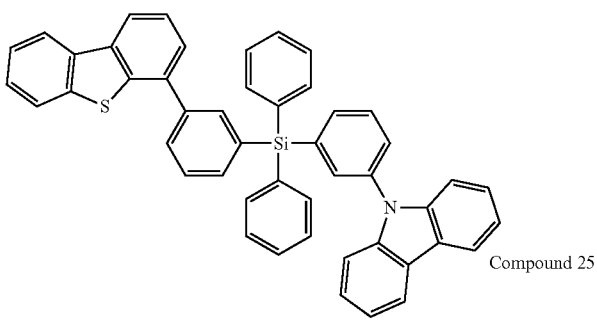
Compound 25
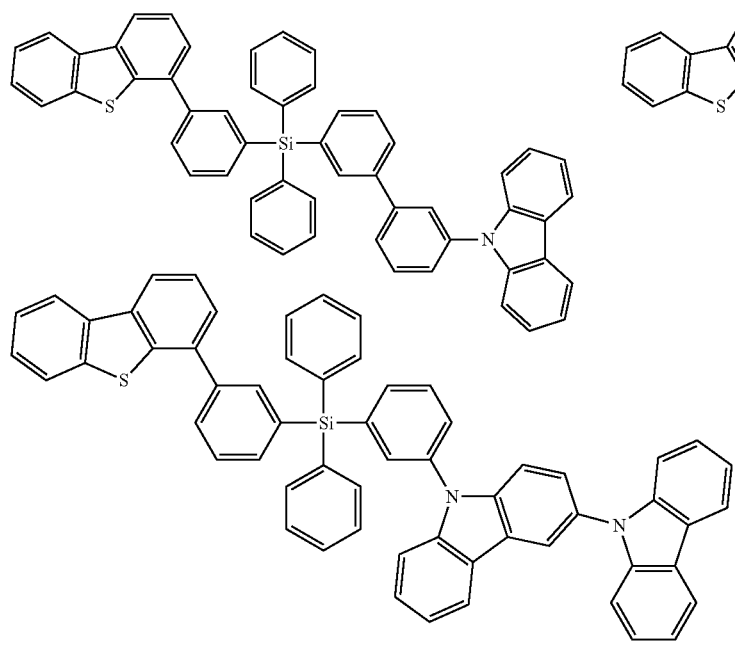

-continued
Compound 26
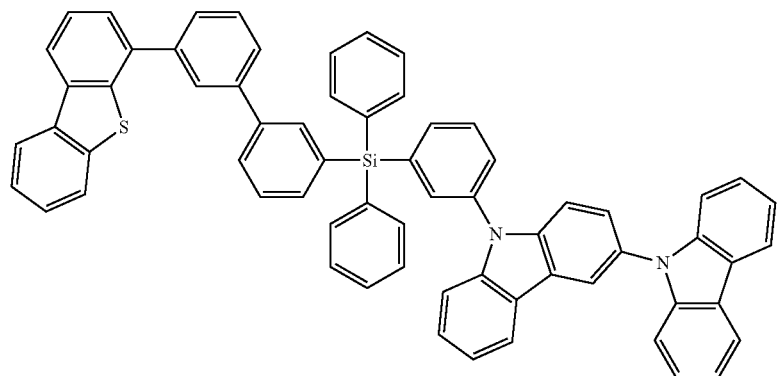
Compound 27
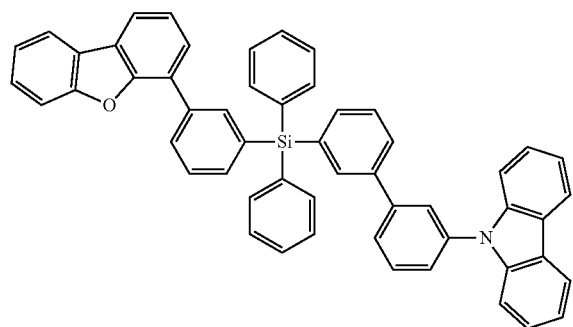
Compound 28
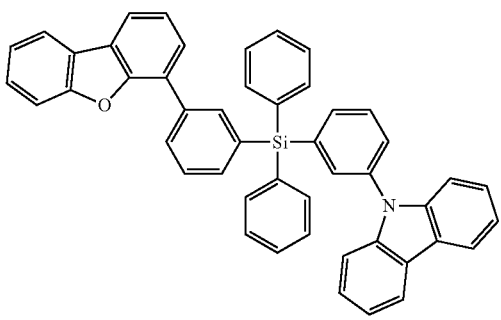
Compound 29
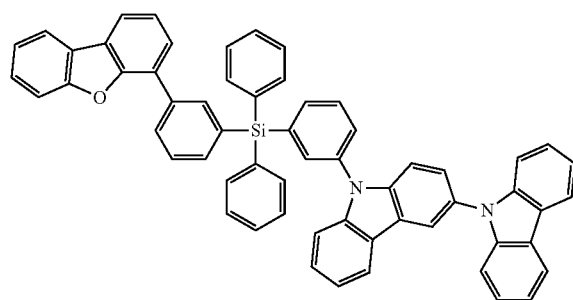
Compound 30
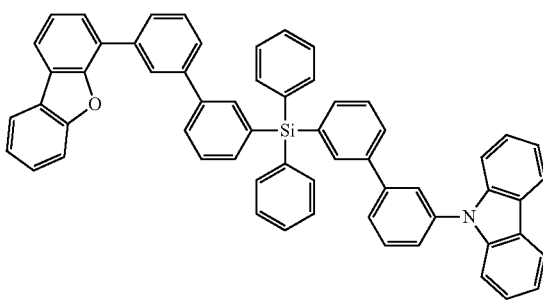
Compound 31
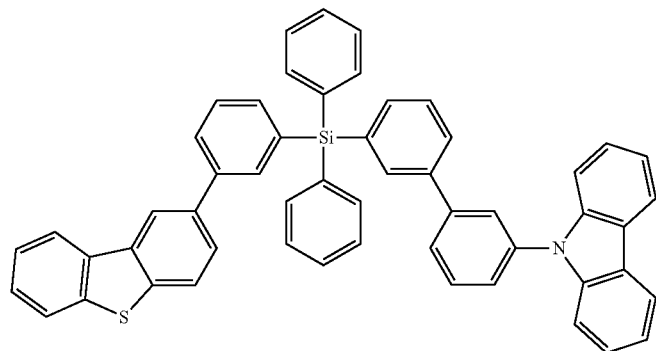

Compound 32
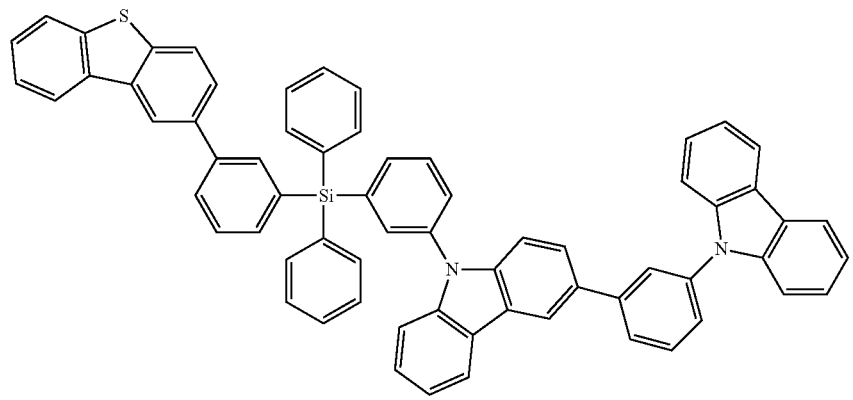
Compound 33
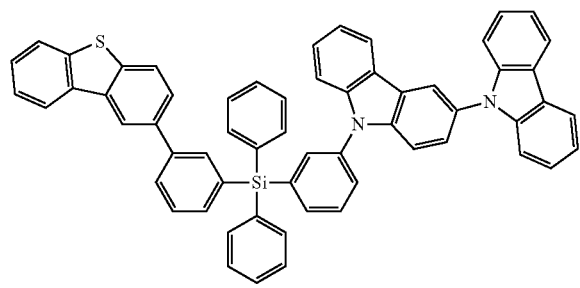
Compound 34
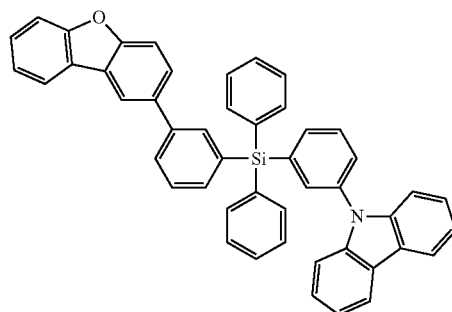
Compound 35
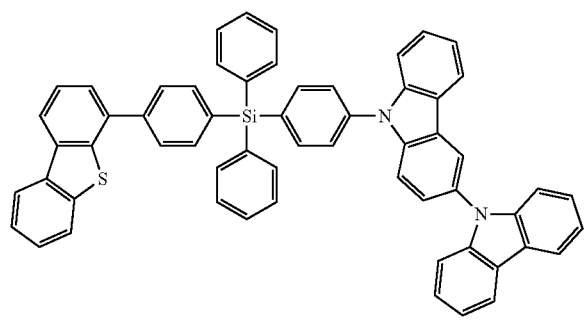
Compound 36
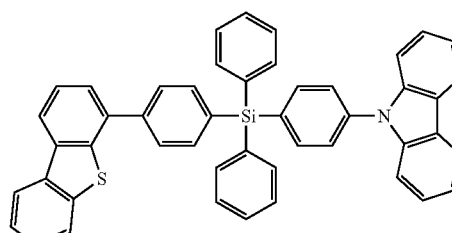
Compound 37
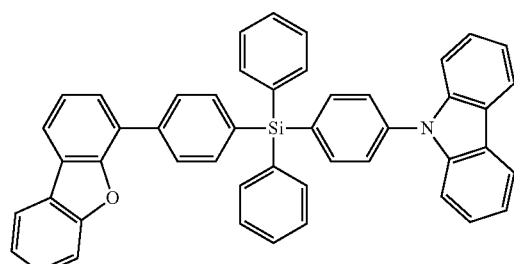
Compound 38
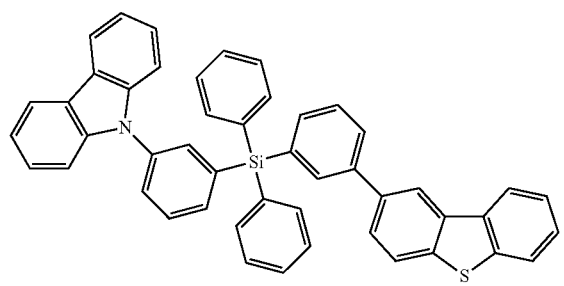

10. A first device comprising an organic light emitting device, further comprising:
an anode;
a cathode; and
an organic layer, disposed between the anode and the cathode, comprising a compound having the Formula I:

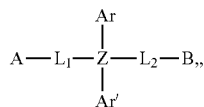

Formula I wherein Ar and Ar' are independently selected from the group consisting of phenyl, biphenyl, napthyl, dibenzothiolyl, and dibenzofuranyl, which are optionally further substituted;
wherein Z is selected from Si and Ge;
wherein $L_1$ comprises aryl or heteroaryl groups, wherein any heteroatoms in the heteroaryl groups are nitrogen;
wherein $L_2$ comprises aryl or heteroaryl groups, wherein any heteroatoms in the heteroaryl groups are nitrogen;
wherein $L_1$ and $L_2$ are optionally further substituted;
wherein A contains a group selected from the group consisting of dibenzofuran, dibenzothiophene, azadibenzofuran, azadibenzothiophene, dibenzoselenophene and azadibenzoselenophene, which are optionally further substituted, and wherein the substitution is optionally fused to at least one benzo ring; and
wherein B contains a group selected from the group consisting of carbazole and azacarbazole, which are optionally further substituted, and wherein the substitution is optionally fused to the carbazole or azacarbazole group.

11. The first device of claim 10, wherein the organic layer is an emissive layer and the compound of Formula I is a host.

12. The first device of claim 10, wherein the organic layer further comprises an emissive dopant.

13. The first device of claim 12, wherein the emissive dopant is a transition metal complex having at least one ligand selected from the group consisting of:

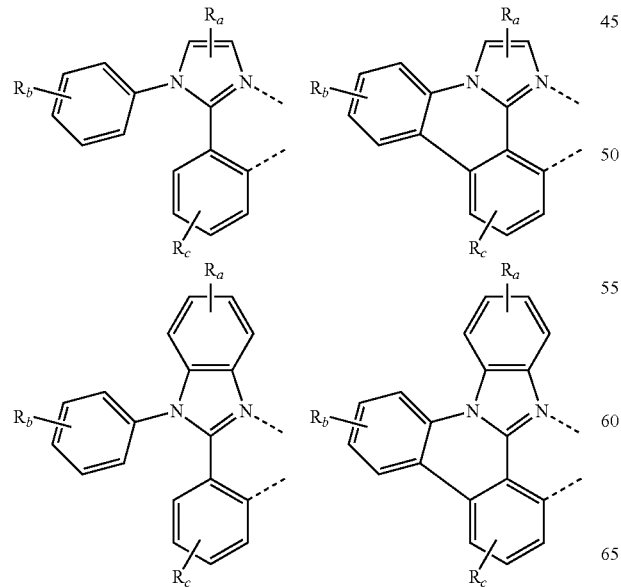

-continued

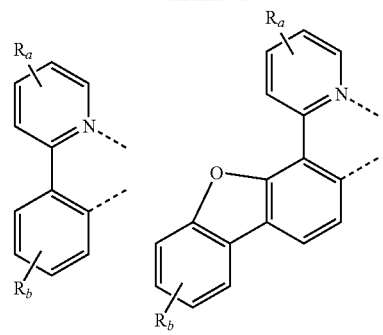

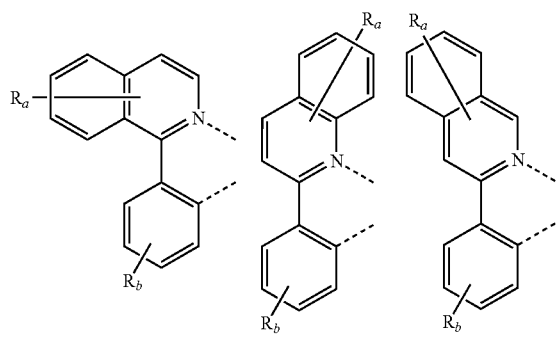

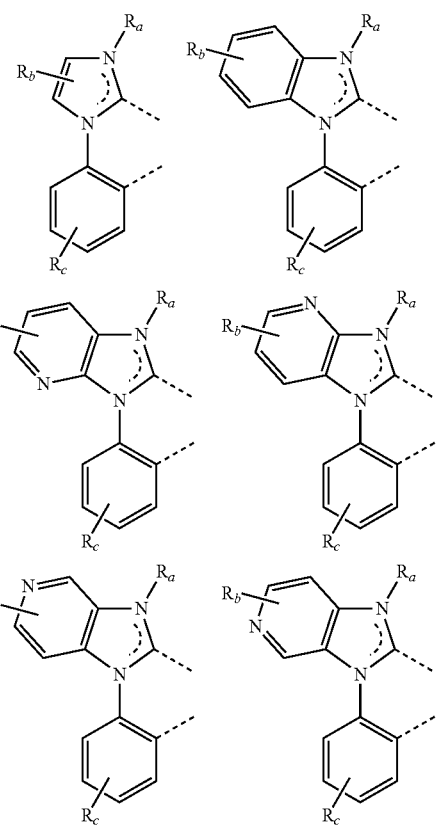

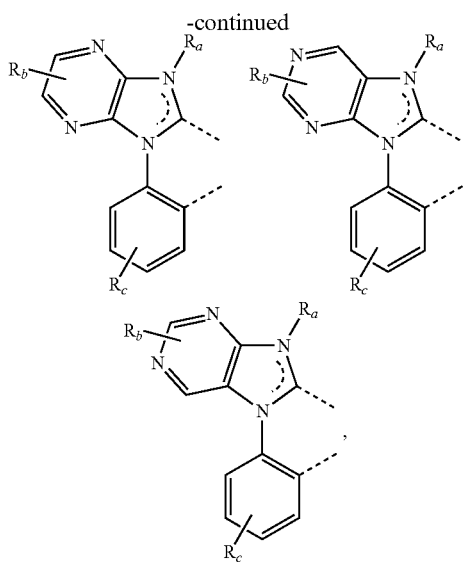

wherein $R_a$, $R_b$, and $R_c$ may represent mono, di, tri or tetra substitutions;

wherein $R_a$, $R_b$, and $R_c$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of $R_a$, $R_b$, and $R_c$ are optionally joined to form a fused ring.

14. The first device of claim 10, wherein the device further comprises a second organic layer that is a non-emissive layer and the compound having Formula I is a material in the second organic layer.

15. The first device of claim 10, wherein the organic layer is deposited using a solution process.

16. A first device comprising an organic light emitting device, further comprising:
an anode;
a cathode; and
an organic layer, disposed between the anode and the cathode, comprising a compound having the Formula I:

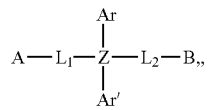

Formula I wherein Ar and Ar' are independently selected from the group consisting of phenyl, biphenyl, napthyl, dibenzothiolyl, and dibenzofuranyl, which are optionally further substituted;

wherein Z is selected from Si and Ge;

wherein $L_1$ comprises aryl or heteroaryl groups, wherein any heteroatoms in the heteroaryl groups are nitrogen;

wherein $L_2$ is a single bond or comprises aryl or heteroaryl groups, wherein any heteroatoms in the heteroaryl groups are nitrogen;

wherein $L_1$ and $L_2$ are optionally further substituted;

wherein A contains a group selected from the group consisting of dibenzofuran, dibenzothiophene, azadibenzofuran, azadibenzothiophene, dibenzoselenophene and azadibenzoselenophene, which are optionally further substituted, and wherein the substitution is optionally fused to at least one benzo ring;

wherein B contains a group selected from the group consisting of carbazole and azacarbazole, which are optionally further substituted, and wherein the substitution is optionally fused to the carbazole or azacarbazole group;

wherein the device further comprises a second organic layer that is a non-emissive layer and the compound having Formula I is a material in the second organic layer; and wherein the second organic layer is a blocking layer and the compound having Formula I is a blocking material in the second organic layer.

17. The first device of claim 10, wherein the first device is a consumer product.

18. The first device of claim 10, wherein the first device is an organic light-emitting device.

19. The first device of claim 14, wherein the second organic layer is a blocking layer and the compound having Formula I is a blocking material in the second organic layer.

* * * * *

UNITED STATES PATENT AND TRADEMARK OFFICE
CERTIFICATE OF CORRECTION

PATENT NO. : 8,748,012 B2  Page 1 of 1
APPLICATION NO. : 13/067345
DATED : June 10, 2014
INVENTOR(S) : Lichang Zeng, Alexey B. Dyatkin and Gregg Kottas It is certified that error appears in the above-identified patent and that said Letters Patent is hereby corrected as shown below:

In the Claims:

In column 144, line 25, of claim 7, "chiysene" should be -- chrysene --

Signed and Sealed this
Twelfth Day of August, 2014

Michelle K. Lee
*Deputy Director of the United States Patent and Trademark Office*